United States Patent
McGuigan et al.

(10) Patent No.: US 9,351,989 B2
(45) Date of Patent: May 31, 2016

(54) SUBSTITUTED PURINE NUCLEOSIDES, PHOSPHOROAMIDATE AND PHOSPHORODIAMIDATE DERIVATIVES FOR TREATMENT OF VIRAL INFECTIONS

(75) Inventors: Chris McGuigan, Cardiff (GB); Karolina Madela, Cardiff (GB); Claire Bourdin, Cardiff (GB); John Vernachio, Canton, GA (US); Stanley Chamberlain, Chapel Hill, NC (US)

(73) Assignees: INHIBITEX, INC., Alpharetta, GA (US); UNIVERSITY COLLEGE CARDIFF CONSULTANTS LIMITED, Cardiff (GB)

( * ) Notice: Subject to any disclaimer, the term of this patent is extended or adjusted under 35 U.S.C. 154(b) by 257 days.

(21) Appl. No.: 13/988,354

(22) PCT Filed: Dec. 29, 2011

(86) PCT No.: PCT/US2011/067862
§ 371 (c)(1),
(2), (4) Date: Jan. 24, 2014

(87) PCT Pub. No.: WO2012/092484
PCT Pub. Date: Jul. 5, 2012

(65) Prior Publication Data
US 2014/0140955 A1    May 22, 2014

Related U.S. Application Data

(60) Provisional application No. 61/427,848, filed on Dec. 29, 2010.

(51) Int. Cl.

| | |
|---|---|
| A61K 38/21 | (2006.01) |
| A01N 43/04 | (2006.01) |
| A61K 31/70 | (2006.01) |
| C07H 19/20 | (2006.01) |
| C07H 19/052 | (2006.01) |
| A61K 31/7076 | (2006.01) |
| C07D 473/16 | (2006.01) |
| C07D 473/18 | (2006.01) |
| C07D 473/24 | (2006.01) |
| A61K 31/708 | (2006.01) |
| C07H 19/067 | (2006.01) |
| A61K 45/06 | (2006.01) |
| C07H 17/02 | (2006.01) |
| A61K 31/7056 | (2006.01) |

(52) U.S. Cl.
CPC .......... *A61K 31/7076* (2013.01); *A61K 31/708* (2013.01); *A61K 31/7056* (2013.01); *A61K 38/21* (2013.01); *A61K 45/06* (2013.01); *C07D 473/16* (2013.01); *C07D 473/18* (2013.01); *C07D 473/24* (2013.01); *C07H 17/02* (2013.01); *C07H 19/067* (2013.01)

(58) Field of Classification Search
CPC ... A61K 45/06; A61K 38/21; A61K 31/7056; A61K 31/708; A61K 31/7076; A61K 2300/00; C07H 19/067; C07H 17/02; C07D 473/21; C07D 473/18; C07D 437/16
See application file for complete search history.

(56) References Cited

U.S. PATENT DOCUMENTS

| | | | |
|---|---|---|---|
| 4,107,288 | A | 8/1978 | Oppenhem et al. |
| 5,145,684 | A | 9/1992 | Liversidge et al. |
| 5,492,897 | A | 2/1996 | Krenitsky et al. |
| 5,597,691 | A | 1/1997 | Houghton et al. |
| 5,607,915 | A | 3/1997 | Patton |
| 5,739,002 | A | 4/1998 | De Francesco et al. |
| 5,747,472 | A | 5/1998 | Krenitsky et al. |
| 5,759,795 | A | 6/1998 | Jubin |
| 5,821,236 | A | 10/1998 | Krenitsky et al. |
| 5,861,267 | A | 1/1999 | Su |
| 5,981,247 | A | 11/1999 | Hagedorn et al. |

(Continued)

OTHER PUBLICATIONS

European Search Report dated Jun. 4, 2014 in corresponding European Application No. 11852610.2.

(Continued)

*Primary Examiner* — Lawrence E Crane
(74) *Attorney, Agent, or Firm* — B. Aaron Schulman, Esq.; Stites & Harbison, PLLC.

(57) ABSTRACT

This invention is directed to phosphoroamidate and phosphorodiamidate derivatives including the compounds of formula (I) having the structure

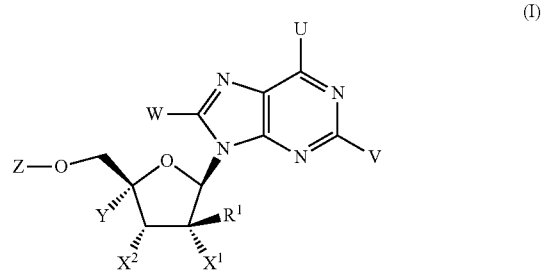

wherein U, V, W, Z, $R^1$, $X^1$, $X^2$, and Y are defined herein. These compounds and pharmaceutical compositions containing these compounds are useful in the treatment of viral infections in mammals infected by a virus in the Flaviviridae family of viruses, in particular hepatitis C virus (HCV). The compounds of this invention may be prepared by various methods known in the art of organic chemistry in general and nucleoside and nucleotide analog synthesis in particular.

7 Claims, No Drawings

(56) References Cited

U.S. PATENT DOCUMENTS

| | | | |
|---|---|---|---|
| 6,030,785 A | 2/2000 | Katze et al. | |
| 6,228,576 B1 | 5/2001 | DelVecchio | |
| 6,448,281 B1 | 9/2002 | Beaulieu et al. | |
| 6,770,666 B2 | 8/2004 | Hashimoto et al. | |
| 6,812,219 B2 * | 11/2004 | LaColla et al. | 514/49 |
| 6,841,566 B2 | 1/2005 | Beaulieu et al. | |
| 6,914,054 B2 * | 7/2005 | Sommadossi et al. | 514/49 |
| 7,101,861 B2 * | 9/2006 | Sommadossi et al. | 514/49 |
| 7,105,493 B2 * | 9/2006 | Sommadossi et al. | 514/42 |
| 7,141,574 B2 | 11/2006 | Beaulieu et al. | |
| 7,148,206 B2 * | 12/2006 | Sommadossi et al. | 514/45 |
| 7,157,441 B2 * | 1/2007 | Sommadossi et al. | 514/47 |
| 7,163,929 B2 * | 1/2007 | Sommadossi et al. | 514/49 |
| 7,169,766 B2 * | 1/2007 | Sommadossi et al. | 514/49 |
| 7,183,302 B2 | 2/2007 | Romine et al. | |
| 7,608,597 B2 * | 10/2009 | Sommadossi et al. | 514/42 |
| 7,662,809 B2 | 2/2010 | Ercolani et al. | |
| 7,795,250 B2 | 9/2010 | Colarusso et al. | |
| 7,951,789 B2 * | 5/2011 | Sommadossi et al. | 514/50 |
| 7,977,331 B1 | 7/2011 | Oka et al. | |
| 8,263,575 B2 | 9/2012 | McGuigan et al. | |
| 8,299,038 B2 * | 10/2012 | Sommadossi et al. | 514/42 |
| 8,343,937 B2 * | 1/2013 | Sommadossi et al. | 514/43 |
| 8,759,318 B2 * | 6/2014 | Chamberlain et al. | 514/48 |
| 2003/0060400 A1 | 3/2003 | LaColla et al. | |
| 2004/0063658 A1 | 4/2004 | Roberts et al. | |
| 2008/0286230 A1 | 11/2008 | Sommadossi et al. | |
| 2010/0286083 A1 | 11/2010 | Bao et al. | |
| 2012/0052046 A1 | 3/2012 | Chamberlain et al. | |

OTHER PUBLICATIONS

International Search Report for PCT/US2011/067862; Aug. 30, 2012.

* cited by examiner

US 9,351,989 B2

SUBSTITUTED PURINE NUCLEOSIDES, PHOSPHOROAMIDATE AND PHOSPHORODIAMIDATE DERIVATIVES FOR TREATMENT OF VIRAL INFECTIONS

CROSS REFERENCE TO RELATED APPLICATIONS

The present application is a 371 application of International Application PCT/US2011/067862 filed Dec. 29, 2011, and claims the benefit of U.S. Provisional Application Ser. No. 61/427,848, filed Dec. 29, 2010, the entire disclosure of which is incorporated herein by reference.

FIELD OF THE INVENTION

This application relates to novel nucleosides and phosphoroamidates and phosphordiamidates of novel nucleosides and their use as agents for treating viral diseases. Such compounds are inhibitors of RNA-dependant RNA viral replication and specifically, inhibitors of HCV NS5B polymerase. As inhibitors of HCV replication, such compounds are useful for treatment of hepatitis C infection in mammals.

BACKGROUND OF THE INVENTION

HCV is a member of the Flaviviridae family of RNA viruses that affect animals and humans. The genome is a single 9.6-kilobase strand of RNA, and consists of one open reading frame that encodes for a polyprotein of approximately 3000 amino acids flanked by untranslated regions at both 5' and 3' ends (5'- and 3'-UTR). The polyprotein serves as the precursor to at least 10 separate viral proteins critical for replication and assembly of progeny viral particles.

Hepatitis C Virus (HCV) infection is a major health problem that leads to chronic liver disease, such as cirrhosis and hepatocellular carcinoma, in a substantial number of infected individuals, estimated to be 2-15% of the world population. There are an estimated 4.5 million infected people in the United States alone, according to the U.S. Center for Disease control. According to the World Health Organization, there are more than 200 million infected individuals worldwide, with at least 3 to 4 million people being infected each year. Once infected, about 20% of people clear the virus, but the remainder can harbor HCV for the rest of their lives.

Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring At present, the standard treatment for chronic HCV is interferon alpha (IFN-alpha) in combination with ribavirin, which requires at least six (6) months of treatment. However, treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha and ribavirin. By now, standard therapy of chronic hepatitis C has been changed to the combination of pegylated IFN-alpha plus ribavirin. However, a number of patients still have significant side effects, primarily related to ribavirin.

Ribavirin causes significant hemolysis in 10-20% of patients treated at currently recommended doses, and the drug is both teratogenic and embryotoxic. Even with recent improvements, a substantial fraction of patients do not respond with a sustained reduction in viral load and there is a clear need for more effective antiviral therapy of HCV infection.

A number of other approaches are being pursued to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. Among the viral targets, the NS3/4A protease/helicase and the NS5b RNA-dependent RNA polymerase are considered the most promising viral targets for new drugs.

A number of patents disclose and claim inventions relating to HCV NS5B inhibitors. For example, WO 2006/046039, WO 2006/046030 and WO 2006/029912, incorporated by reference herein, relate to tetracyclic indole compounds and pharmaceutically acceptable salts thereof, for the treatment or prevention of infection by hepatitis C virus. WO 2005/080399, incorporated by reference herein, relates to fused heterotetracyclic compounds, pharmaceutically acceptable salts thereof; and their use in aiding to remedy hepatitis C infection as potent (HCV) polymerase inhibitors. WO 2003/007945, incorporated by reference herein, relates to HCV NS5B inhibitors. Further, WO 2003/010140, incorporated by reference herein, relates to specific inhibitors of RNA dependent RNA polymerases, particularly viral polymerases within the Flaviviridae family, more particularly to HCV polymerase. WO 2002/04425, incorporated by reference herein, relates to specific inhibitors of RNA dependent RNA polymerases, particularly viral polymerases within the Flaviviridae family, and more particularly the NS5B polymerase of HCV. WO 200147883, incorporated by reference herein, relates to specific fused-ring compounds or the like or pharmaceutically acceptable salts thereof. Such compounds and salts exhibit an anti-HCV (hepatitis C virus) activity by virtue of their inhibitory activity against HCV polymerase, thus being useful as therapeutic or preventive agents for hepatitis C.

However, in view of the worldwide epidemic level of HCV and other members of the Flaviviridae family of viruses, and further in view of the limited treatment options, there is a strong need for new effective drugs for treating infections cause by these viruses.

SUMMARY OF THE INVENTION

This invention is directed to novel compounds that are useful in the treatment of viral infections in mammals mediated, at least in part, by a virus in the Flaviviridae family of viruses. According to some embodiments, the present invention provides for novel compounds of formula (I) having the structure:

(I)

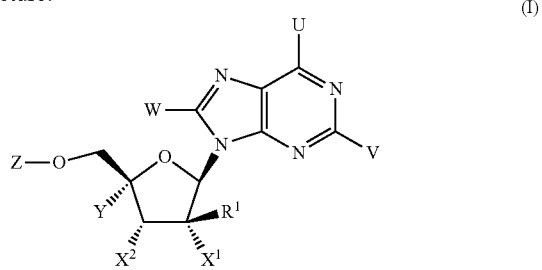

wherein
U and V are each independently selected from the group consisting of
  Hydrogen
  OH
  Cl
  Br
  I
  $OR^1$
  $NH_2$
  $NHR^2$
  $NR^2R^2$
  SH
  and
  $SR^3$
  wherein
    $R^1$, $R^2$ and $R^3$ are independently $C_1$-$C_6$ alkyl or alkyl($C_1$-$C_3$)aryl;
W is independently selected from the group consisting of
  I
  OH
  $NH_2$
  SH
  $SR^4$
  $OR^5$
  $NHR^6$
  and
  $NR^6R^6$
  wherein
    $R^4$, $R^5$ and $R^6$ are independently $C_1$-$C_6$ alkyl or aryl($C_1C_3$)alkyl;
$X^1$ is OH or F;
$X^2$ is OH;
Y is hydrogen or $N_3$ (azido);
Z is selected from the group consisting of
  H
  —P(O)(OAr)$NHR^7$
  —P(O)$(NHR^7)_2$
  —P(O)($O^-$)$NHR^7$
  —P(O)$O^-_2$ (monophosphate)
  and
  —$PO_2$—O—$PO_2$—O—$PO_3$ (triphosphate)
  wherein
    $R^7$ is
      —C($R^8$)($R^9$)C(O)$OR^{10}$
      wherein
        $R^8$ and $R^9$ are independently
          hydrogen
          alkyl
          aryl($C_1$-$C_6$)alkyl
          or
          phenyl,
        $R^{10}$ is $C_1$-$C_6$ alkyl
          aryl($C_1$-$C_6$)alkyl

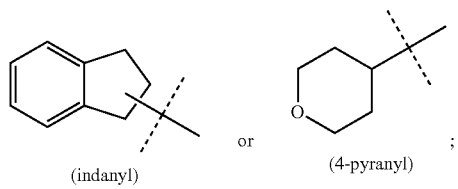

(indanyl)   or   (4-pyranyl)   ;

and

Ar is independently selected from the group consisting of
  phenyl
  1-naphthyl
  2-naphthyl

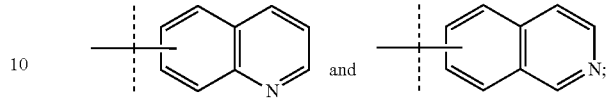

and the pharmaceutically acceptable salts thereof.

According to other embodiments, the present invention extends to a pharmaceutical composition comprising one or more compounds of formula I and a pharmaceutically acceptable carrier, excipient or diluent. The pharmaceutically acceptable carrier, excipient or diluent may be pure sterile water, phosphate buffered saline or an aqueous glucose solution.

Also provided are methods for treating a viral infection in a mammal mediated at least in part by a virus in the Flaviviridae family wherein an instant method comprises administering to a mammal that has been diagnosed with said viral infection a pharmaceutical composition comprising compounds of formula I.

Also provided are methods for treating a viral infection in a human or animal patient that is mediated at least in part by a virus in the Flaviviridae family wherein an instant method comprises administering to a human or animal patient in need thereof an effective amount of a pharmaceutical composition comprising compounds of formula I.

In one embodiment, the virus is hepatitis C virus (or HCV). The present invention thus further extends to combinations of the above compounds with one or more agents active against hepatitis C virus and to methods of combination treatment comprising administration of a therapeutically effective amount of one or more agents active against hepatitis C virus. Such active agents against hepatitis C virus may include interferon-alpha or pegylated interferon-alpha alone or in combination with ribavirin or levovirin.

DETAILED DESCRIPTION OF THE INVENTION

The present invention relates to chemical compounds, their preparation and their use in the treatment of viral infections, particularly those viruses in a mammal which are mediated at least in part by a virus in the Flaviviridae family of viruses. Particularly, although not exclusively, the present invention relates to chemical compounds useful as anti-hepatitis C virus (HCV) agents.

Specifically, the present invention describes certain nucleoside diphosphoroamidates, their synthesis, and their use as precursors to inhibitors of RNA-dependent RNA viral polymerase, particularly their use as precursors to inhibitors of hepatitis C virus (HCV) NS5-B polymerase, as precursors to inhibitors of HCV replication, and for the treatment of hepatitis C infection.

It is an object of the present invention to provide novel chemical compounds useful for treatment of viral infections in mammals, particularly infections caused by viruses of the Flaviviridae family of viruses, and specifically for treatment of hepatitis C infection in mammals.

The present invention relates to novel compounds of formula (I) having the structure:

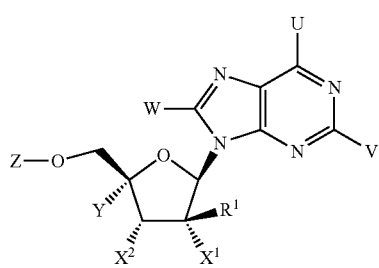

(I)

wherein
U and V are each independently selected from the group consisting of
  Hydrogen
  OH
  Cl
  Br
  I
  $OR^1$
  $NH_2$
  $NHR^2$
  $NR^2R^2$
  SH
  and
  $SR^3$
  wherein
    $R^1$, $R^2$, and $R^3$ are independently $C_1$-$C_6$ alkyl or alkyl($C_1$-$C_3$)aryl;
W is independently selected from the group consisting of
  I
  OH
  $NH_2$
  SH
  $SR^4$
  $OR^5$
  $NHR^6$
  and
  $NR^6R^6$,
  wherein
    $R^4$, $R^5$ and $R^6$ are independently $C_1$-$C_6$ alkyl or alkyl($C_1$-$C_3$)aryl;
$X^1$ is OH or F;
$X^2$ is OH;
Y is hydrogen or $N_3$ (azido);
Z is selected from the group consisting of
  H
  —P(O)(OAr)$NHR^7$
  —P(O)($NHR^7$)$_2$
  —P(O)($O^-$)$NHR^7$
  —P(O)$O^-_2$ (monophosphate)
  and
  —$PO_2$—O—$PO_2$—O—$PO_3$ (triphosphate)
  wherein
    $R^7$ is
      —C($R^8$)($R^9$)C(O)$OR^{10}$
      wherein
        $R^8$ and $R^9$ are independently
          hydrogen
          alkyl
          aryl($C_1$-$C_6$)alkyl
          or
          phenyl,
        $R^{10}$ is $C_1$-$C_6$ alkyl
          aryl($C_1$-$C_6$)alkyl

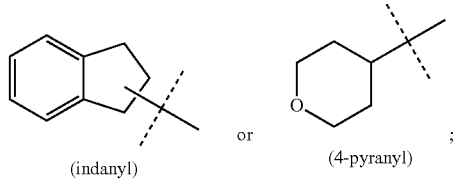

(indanyl) or (4-pyranyl);

and
Ar is independently selected from the group consisting of
  phenyl
  1-naphthyl
  2-naphthyl

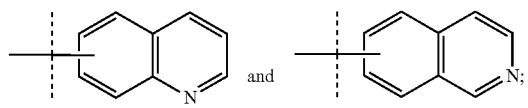

and and the pharmaceutically acceptable salts thereof.

In each case, the above compounds are provided along with their phosphorus diastereomers.

In accordance with the present invention there are provided the following specific embodiments of the above compounds:

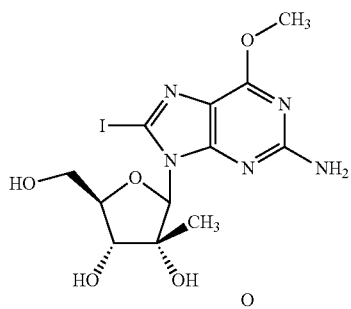

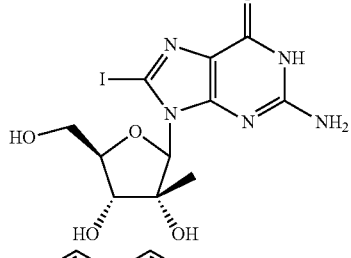

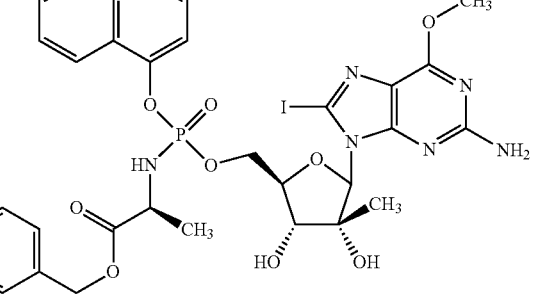

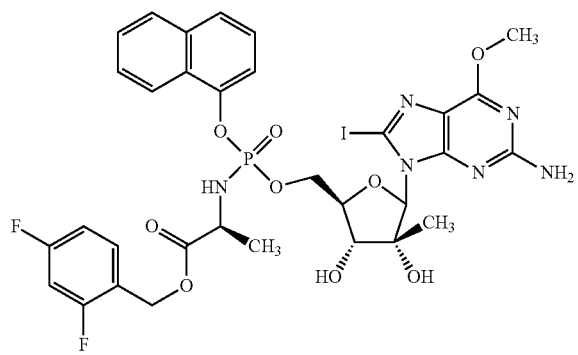
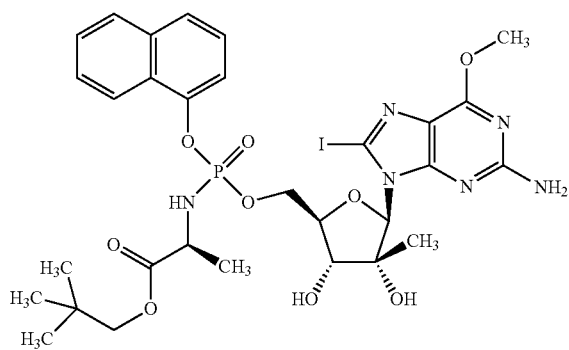
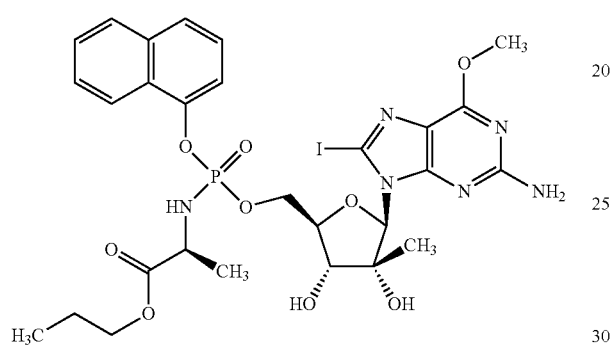
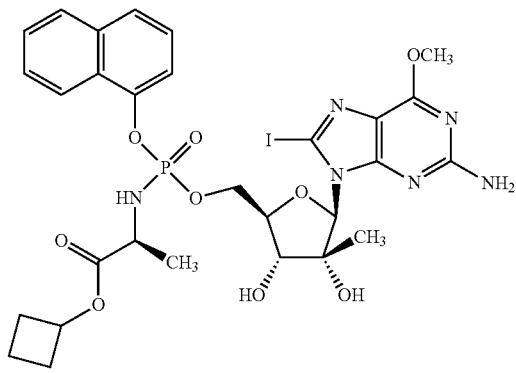
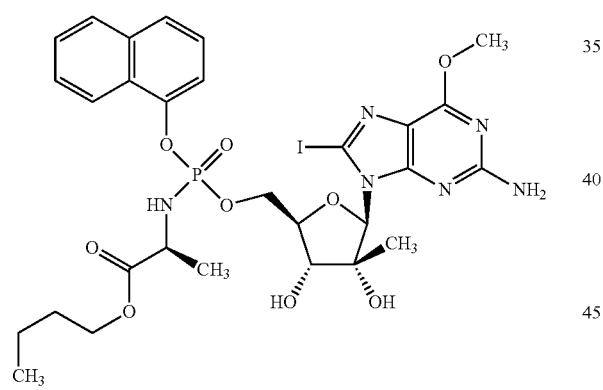
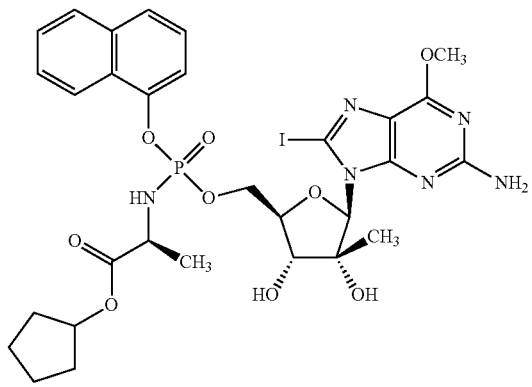
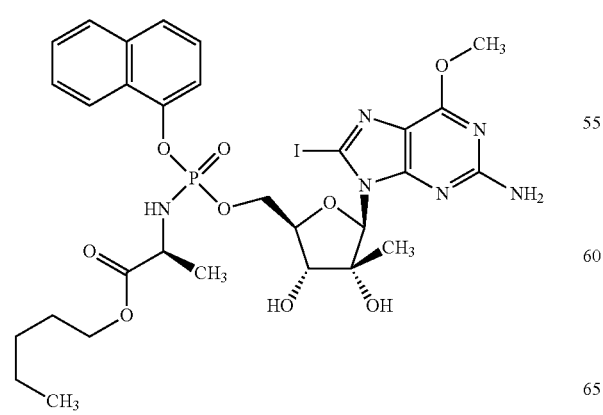
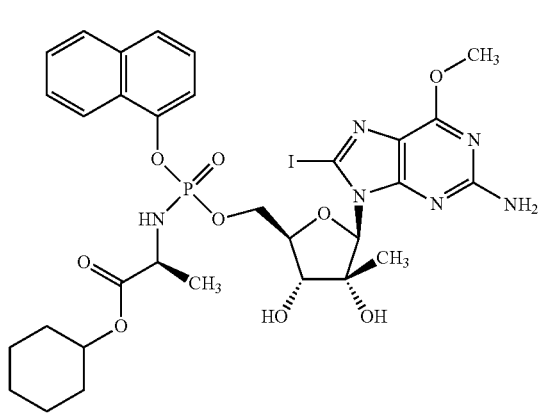

-continued
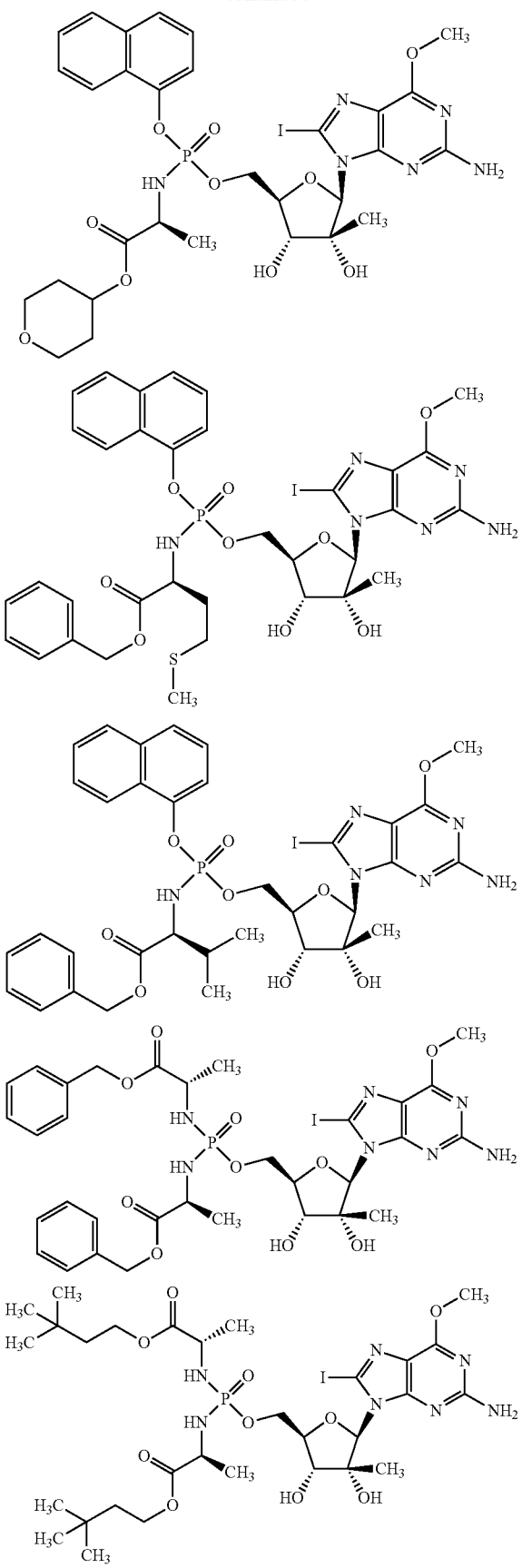
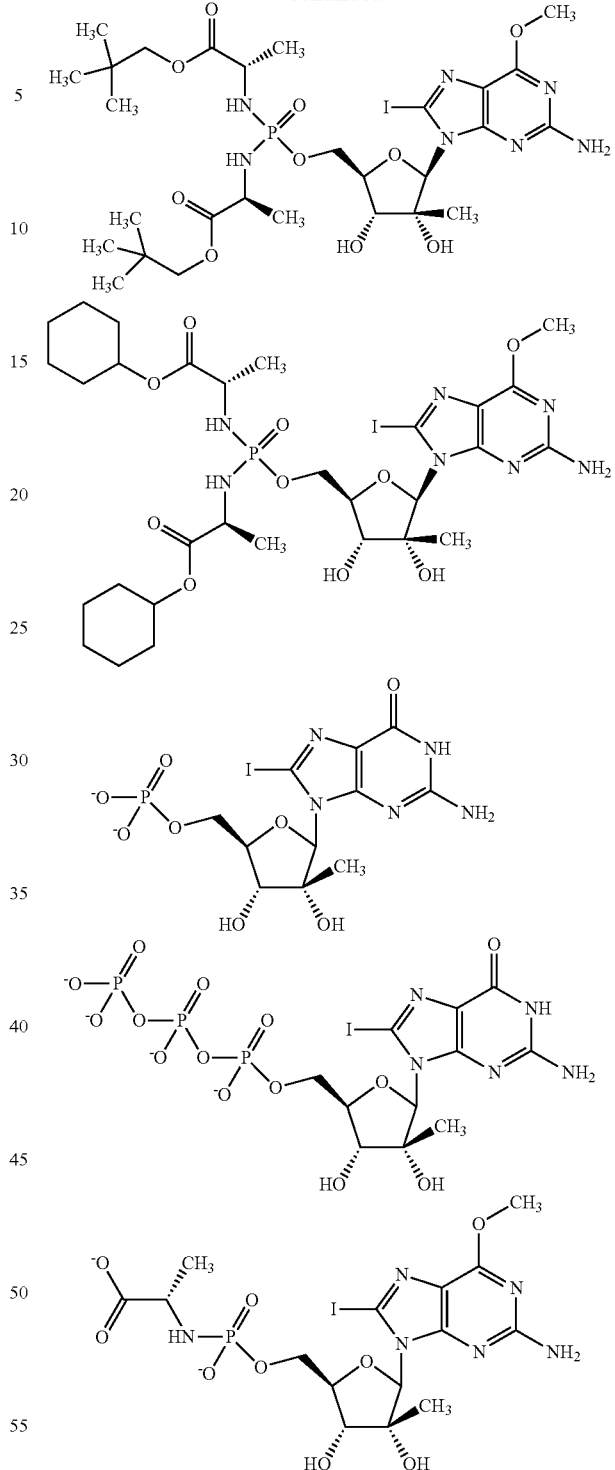
and the pharmaceutically acceptable salts thereof.
In accordance with the present invention, there are provided the following specific embodiments of the above compounds:
(2R,3R,4R,5R)-2-(2-amino-8-iodo-6-methoxy-9H-purin-9-yl)-5-(hydroxymethyl)-3-methyltetrahydrofuran-3,4-diol
2-amino-9-((2R,3R,4R,5R)-3,4-dihydroxy-5-(hydroxymethyl)-3-methyltetrahydrofuran-2-yl)-8-iodo-1H-purin-6 (9H)-one benzyl 2(S)-(((((2R,3R,4R,5R)-5-(2-amino-8-iodo-6-methoxy-9H-purin-9-yl)-3,4-dihydroxy-4-methyltetrahydrofuran-2-yl)methoxy(naphthalene-1-yloxy)phosphorylamino)propanoate;

(2S)-2,4-difluorobenzyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;

(2S)-propyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;

(2S)-butyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate (2S)-pentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate (2S)-neopentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate (2S)-cyclobutyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate (2S)-cyclopentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate (2S)-cyclohexyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;

(2S)-tetrahydro-2H-pyran-4-yl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;

(2S)-benzyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-4-(methylthio)butanoate (2S)-benzyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate (2S,2'S)-benzyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-bis(3,3-dimethylbutyl) 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-neopentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-dicyclohexyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate ((2R,3R,4R,5R)-5-(2-amino-8-iodo-6-oxo-1H-purin-9(6H)-yl)-3,4-dihydroxy-4-methyltetrahydrofuran-2-yl)methyl phosphate ((2R,3R,4R,5R)-5-(2-amino-8-iodo-6-oxo-1H-purin-9(6H)-yl)-3,4-dihydroxy-4-methyltetrahydrofuran-2-yl)methyl triphosphate (S)-2-((((2R,3R,4R,5R)-5-(2-amino-8-iodo-6-methoxy-9H-purin-9-yl)-3,4-dihydroxy-4-methyltetrahydrofuran-2-yl)methoxy)oxidophosphorylamino)propanoate 1(S)-phenylethyl 2(S)-((((2R,3R,4R,5R)-5-(2-amino-8-iodo-6-methoxy-9H-purin-9-yl)-3,4-dihydroxy-4-methyltetrahydrofuran-2-yl)methoxy(naphthalene-1-yloxy)phosphorylamino)propanoate;

(2S)-2,3-dihydro-1H-inden-2-yl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;

(2S)-3,3-dimethylbutyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;

(2S)-isobutyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;

(S)—P 2,2-dimethylpropyl 2(S)-((((2R,3R,4R,5R)-5-(2-amino-8-iodo-6-methoxy-9H-purin-9-yl)-3,4-dihydroxy-4-methyltetrahydrofuran-2-yl)methoxy(naphthalene-1-yloxy)phosphorylamino)propanoate;

(R)—P 2,2-dimethylpropyl 2(S)-((((2R,3R,4R,5R)-5-(2-amino-8-iodo-6-methoxy-9H-purin-9-yl)-3,4-dihydroxy-4-methyltetrahydrofuran-2-yl)methoxy(naphthalene-1-yloxy)phosphorylamino)propanoate;

(2S)-isopropyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;

(2S)-2,4-difluorobenzyl 2-((((2R,3R,4R,5R)-5-(2-amino-8-iodo-6-methoxy-9H-purin-9-yl)-3,4-dihydroxy-4-methyltetrahydrofuran-2-yl)methoxy)(quinolin-5-yloxy)phosphorylamino)propanoate;

(2S)-neopentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(quinolin-5-yloxy)phosphorylamino)propanoate (2S)-tetrahydro-2H-pyran-4-yl 2-((((2R,3R,4R,5R)-5-(2-amino-8-iodo-6-methoxy-9H-purin-9-yl)-3,4-dihydroxy-4-methyltetrahydrofuran-2-yl)methoxy)(quinolin-5-yloxy)phosphorylamino)propanoate (2S)-neopentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(quinolin-6-yloxy)phosphorylamino)propanoate (2S)-tetrahydro-2H-pyran-4-yl 2-((((2R,3R,4R,5R)-5-(2-amino-8-iodo-6-methoxy-9H-purin-9-yl)-3,4-dihydroxy-4-methyltetrahydrofuran-2-yl)methoxy)(quinolin-6-yloxy)phosphorylamino)propanoate (2S)-neopentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(phenoxy)phosphorylamino)propanoate;

(2S)-2,4-difluorobenzyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate (2S)-methyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate (2S)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate (2S)-cyclopropylmethyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate (2S)-cyclobutyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate (2S)-cyclopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate (2S)-cyclohexyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate (2S)-tetrahydro-2H-pyran-4-yl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate (2S)-2,4-difluorobenzyl 2-(((((2R,3R,4R)-5-(2-amino-8-iodo-6-methoxy-9H-purin-9-yl)-3,4-dihydroxy-4-methyltetrahydrofuran-2-yl)methoxy)(quinolin-5-yloxy)phosphorylamino)-3-methylbutanoate;

(2S)-neopentyl 2-(((((2R,3R,4R)-5-(2-amino-8-iodo-6-methoxy-9H-purin-9-yl)-3,4-dihydroxy-4-methyltetrahydrofuran-2-yl)methoxy)(quinolin-6-yloxy)phosphorylamino)-3-methylbutanoate;

(2R)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate (2S)—((S)-1-phenylethyl) 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-4-(methylthio)butanoate (2S)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-4-(methylthio)butanoate;

(2S)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-4-methylpentanoate (2S,3R)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylpentanoate (2S)-benzyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-propyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate (2S)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-cyclohexyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2R)-benzyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2R)-propyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate (2R)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2R)-cyclohexyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(3R,4R,5R)-2-(2-amino-6-ethoxy-8-iodo-9H-purin-9-yl)-5-(hydroxymethyl)-3-methyltetrahydrofuran-3,4-diol benzyl 2(S)-(((((2R,3R,4R,5R)-5-(2-amino-6-ethoxy-8-iodo-9H-purin-9-yl)-3,4-dihydroxy-4-methyltetrahydrofuran-2-yl)methoxy(naphthalene-1-yloxy)phosphorylamino)-3-methylbutanoate;

(2S)-neopentyl 2-(((((2R,3R,4R)-5-(2-amino-6-ethoxy-8-iodo-9H-purin-9-yl)-3,4-dihydroxy-4-methyltetrahydrofuran-2-yl)methoxy)(naphthalen-1-yloxy)phosphorylamino)propanoate (2S)-isopropyl 2-(((((2R,3R,4R)-5-(2-amino-6-ethoxy-8-iodo-9H-purin-9-yl)-3,4-dihydroxy-4-methyltetrahydrofuran-2-yl)methoxy)(naphthalen-1-yloxy)phosphorylamino)propanoate (2S)-neopentyl 2-(((((2R,3R,4R)-5-(2-amino-6-ethoxy-8-iodo-9H-purin-9-yl)-3,4-dihydroxy-4-methyltetrahydrofuran-2-yl)methoxy)(naphthalen-1-yloxy)phosphorylamino)-3-methylbutanoate (2R,3R,4R,5R)-2-(2-amino-8-iodo-6-(methylamino)-9H-purin-9-yl)-5-(hydroxymethyl)-3-methyltetrahydrofuran-3,4-diol (2S)-neopentyl 2-(((((2R,3R,4R,5R)-5-(2-amino-8-iodo-6-(methylamino)-9H-purin-9-yl)-3,4-dihydroxy-4-methyltetrahydrofuran-2-yl)methoxy)(naphthalen-1-yloxy)phosphorylamino)propanoate (2S)-benzyl 2-(((((2R,3R,4R,5R)-5-(2-Amino-8-iodo-6-(methylamino)-9H-purin-9-yl)-3,4-dihydroxy-4-methyltetrahydrofuran-2-yl)methoxy)(naphthalen-1-yloxy)phosphorylamino)propanoate (2R,3R,4R,5R)-2-(2-amino-6-(benzylamino)-8-iodo-9H-purin-9-yl)-5-(hydroxymethyl)-3-methyltetrahydrofuran-3,4-diol (2S)-neopentyl 2-(((((2R,3R,4R,5R)-5-(2-amino-6-(benzylamino)-8-iodo-9H-purin-9-yl)-3,4-dihydroxy-4-methyltetrahydrofuran-2-yl)methoxy)(naphthalen-1-yloxy)phosphorylamino)propanoate (2R,3R,4R,5R)-2-(2-amino-8-iodo-6-(phenethylamino)-9H-purin-9-yl)-5-(hydroxymethyl)-3-methyltetrahydrofuran-3,4-diol (2S)-neopentyl 2-(((((2R,3R,4R,5R)-5-(2-amino-8-iodo-6-(phenethylamino)-9H-purin-9-yl)-3,4-dihydroxy-4-methyltetrahydrofuran-2-yl)methoxy)(naphthalen-1-yloxy)phosphorylamino)propanoate (2R,3R,4R,5R)-2-(2-amino-8-iodo-6-(methylthio)-9H-purin-9-yl)-5-(hydroxymethyl)-3-methyltetrahydrofuran-3,4-diol (2S)-benzyl 2-((((2R,3R,4R,5R)-5-(2-amino-8-iodo-6-(methylthio)-9H-purin-9-yl)-3,4-dihydroxy-4-methyltetrahydrofuran-2-yl)methoxy)(naphthalen-1-yloxy)phosphorylamino)propanoate (2S)-neopentyl 2-((((2R,3R,4R,5R)-5-(2-amino-8-iodo-6-(methylthio)-9H-purin-9-yl)-3,4-dihydroxy-4-methyltetrahydrofuran-2-yl)methoxy)(naphthalen-1-yloxy)phosphorylamino)propanoate (2R,3R,4R,5R)-2-(2-(4-fluorobenzylamino)-8-iodo-6-methoxy-9H-purin-9-yl)-5-(hydroxymethyl)-3-methyltetrahydrofuran-3,4-diol (2S)-neopentyl 2-((((2R,3R,4R,5R)-5-(2-(4-fluorobenzylamino)-8-iodo-6-methoxy-9H-purin-9-yl)-3,4-dihydroxy-4-methyltetrahydrofuran-2-yl)methoxy)(naphthalen-1-yloxy)phosphorylamino)propanoate (2S,2'S)-dimethyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-diethyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-dipropyl-((((2R,3S,4R,5R)-5-(2-amino-8-iodo-6-methoxy-9H-purin-9-yl)-3,4-dihydroxy-4-methyltetrahydrofuran-2-yl)methoxy)phosphoryl)-(2,2')-bis-amino-dipropanoate (2S,2'S)-dibutyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-dipentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-diisobutyl-((((2R,3S,4R,5R)-5-(2-amino-8-iodo-6-methoxy-9H-purin-9-yl)-3,4-dihydroxy-4-methyltetrahydrofuran-2-yl)methoxy)phosphoryl)(2,2')-bis-amino-dipropanoate (2S,2'S)-bis(cyclopropylmethyl) 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-diisopropyl-((((2R,3S,4R,5R)-5-(2-amino-8-iodo-6-methoxy-9H-purin-9-yl)-3,4-dihydroxy-4-methyltetrahydrofuran-2-yl)methoxy)phosphoryl)-(2,2')-bis-amino-dipropanoate (2S,2'S)-sec-butyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-dicyclobutyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-dicyclopentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-bis(tetrahydro-2H-pyran-4-yl) 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)—(S)-phenylethyl-((((2R,3S,4R,5R)-5-(2-amino-8-iodo-6-methoxy-9H-purin-9-yl)-3,4-dihydroxy-4-methyltetrahydrofuran-2-yl)methoxy)phosphoryl)-(2,2')-bis-amino-dipropanoate (2S,2'S)-bis(2,3-dihydro-1H-inden-2-yl) 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S)-benzyl 2-((((2R,3R,4R,5R)-5-(2-amino-8-iodo-6-methoxy-9H-purin-9-yl)-3,4-dihydroxy-4-methyltetrahydrofuran-2-yl)methoxy)((S)-1-(neopentyloxy)-1-oxopropan-2-ylamino)phosphorylamino)propanoate (2S)-cyclohexyl 2-((((2R,3R,4R,5R)-5-(2-amino-8-iodo-6-methoxy-9H-purin-9-yl)-3,4-dihydroxy-4-methyltetrahydrofuran-2-yl)methoxy)((S)-1-(neopentyloxy)-1-oxopropan-2-ylamino)phosphorylamino)propanoate (2S)-neopentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(benzylamino)phosphorylamino)propanoate (2S)-neopentyl 2-((((2R,3R,4R)-5-(2-amino-8-iodo-6-methoxy-9H-purin-9-yl)-3,4-dihydroxy-4-methyltetrahydrofuran-2-yl)methoxy)(naphthalen-1-ylamino)phosphorylamino)propanoate benzyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)diacetate neopentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)diacetate (2R,2'R)-neopentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-benzyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)bis(4-methylpentanoate)

(2R,2'R)-neopentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)bis(4-methylthiobutanoate)

(2S,2'S)-benzyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)bis(3-methyl butanoate)

(2S,2'S)-dicyclohexyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)bis(3-methylbutanoate)

(2S,2'S)-neopentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)bis(2-phenylacetate)

(2S,2'S)-dicyclohexyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)bis(2-phenylacetate)

In each case with regard to the foregoing specific compounds, it is contemplated that the invention will include the pharmaceutically acceptable salts thereof and phosphorus diastereomers thereof.

Compounds according to the present invention have surprisingly been found to have excellent anti-viral activity. In particular, compounds according to the present invention have been found to have excellent potency with respect to hepatitis C virus.

DEFINITIONS

As used herein, the term "alkyl" refers to a straight or branched saturated monovalent cyclic or acyclic hydrocarbon radical, having the number of carbon atoms as indicated (or where not indicated, an acyclic alkyl group preferably has 1-20, more preferably 1-6, more preferably 1-4 carbon atoms and a cyclic alkyl group preferably has 3-20, preferably 3-10, more preferably 3-7 carbon atoms), optionally substituted with one, two, three or more substituents independently selected from the group set out above. By way of non-limiting examples, suitable alkyl groups include methyl, ethyl, propyl, butyl, pentyl, hexyl, octyl, nonyl, isopropyl, 2-butyl, cyclopropyl, cyclohexyl, cyclopentyl and dodecyl. The term "$C_3$-$C_8$cycloalkyl" refers to cyclic alkyl group comprising from about 3 to about 8 C atoms. The term "$C_3$-$C_8$cycloalkylalkyl" refers to an acyclic alkyl group substituted by a cyclic alkyl group comprising from about 3 to about 8 C atoms.

As use herein, the term "alkoxy" or the term "alkyloxy" refers to the group alkyl-O—, where alkyl is as defined above and where the alkyl moiety may optionally be substituted by one, two, three or more substituents as set out above for alkyl. By way of non-limiting examples, suitable alkoxy groups include methoxy, ethoxy, n-propoxy, iso-propoxy, n-butoxy, tert-butoxy, sec-butoxy, n-pentoxy, n-hexoxy and 1,2-dimethylbutoxy. The term "cycloalkyloxy" refers to the group cyclicalkyl-O—, where cyclicalkyl is as defined above and where the cyclicalkyl moiety may be optionally substituted by one, two, three or more substituents as set out above for alkyl.

As used herein, the term "cycloalkylaryl" refers to an aryl group having a cyclic alkyl substituent. Binding is through the aryl group. The cycloalkyl moiety and the aryl moiety are as defined herein with respect to the definitions of cycloalkyl and aryl, respectively.

As used herein, the terms "aryl($C_1$-$C_3$)alkyl" and "aryl($C_1$-$C_6$)alkyl" refer to a $C_1$-$C_3$ alkyl group or a $C_1$-$C_6$ alkyl group, respectively, substituted at any carbon by an aryl group. Binding to the rest of the molecule is through the alkyl group. The aryl moiety and the alkyl moiety are as defined herein with respect to the definitions of aryl and alkyl. The aryl group may be substituted. By way of non-limiting examples, suitable aryl($C_1$-$C_3$)alkyl groups include benzyl, 1-phenylethyl, 3-phenylpropyl, 4-chlorobenzyl, 4-fluorobenzyl, 2,4-difluorobenzyl, and the like. By way of non-limiting examples, suitable aryl($C_1$-$C_6$)alkyl groups include the aryl($C_1$-$C_3$) alkyl groups described above as well as 1-phenylbutyl, 3-phenylpentyl, 6-(4-chlorophenyl)hexyl, 4(4-fluorophenyl)pentyl, 5-(2,4-difluorophenyl)hexyl, and the like.

A cycloalkyl moiety and the aryl moiety may each be optionally substituted by one, two, three or more substituents as set out herein with regard to the definitions of alkyl and aryl, respectively.

As used herein the term "aryl" refers to a monovalent unsaturated aromatic carbocyclic radical having one, two, three, four, five or six rings, preferably one, two or three rings, which may be fused or bicyclic. An aryl group may optionally be substituted by one, two, three or more substituents as set out above with respect to optional substituents that may be present on the group Ar. Preferred aryl groups are: an aromatic monocyclic ring containing 6 carbon atoms; an aromatic bicyclic or fused ring system containing 7, 8, 9 or 10 carbon atoms; or an aromatic tricyclic ring system containing 10, 11, 12, 13 or 14 carbon atoms. Non-limiting examples of aryl include phenyl and naphthyl. These compounds may include substituent groups, preferably those substituent groups independently selected from hydroxy (—OH), acyl (R'—C(=O)), acyloxy (R'—C(O)—O—), nitro (—$NO_2$), amino (—$NH_2$), carboxyl (—COOH), cyano (—CN), $C_1$-$C_6$monoalkylamino, $C_1$-$C_6$dialkylamino, thiol, chloro, bromo, fluoro, iodo, $SO_3H$, —SH, —SW, wherein R' is independently selected from halo, $C_1$-$C_6$alkoxy, and $C_1$-$C_6$alkyl.

When a radical is drawn as a structure, e.g.,

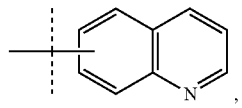

the linking bond between the radical and the rest of the molecule is depicted in the drawing by the fragment

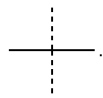

The point of attachment on the radical is at any available position of the ring into which the linking bond is drawn.

As used herein, the term "indanyl" refers to the fused bicyclic radical of structure,

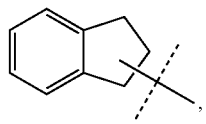

wherein the point of attachment of the radical to the rest of the molecule is on any available non-aromatic carbon atom.

Available carbon atoms and/or heteroatoms of the "heterocycloalkyl" ring systems described above may be substituted on the ring with one or more heteroatoms. Where the ring(s) is substituted with one or more heteroatoms, heteroatom substituents are selected from oxygen, nitrogen, sulphur and halogen (F, Cl, Br and I). Where the ring(s) is substituted with one or more heteroatoms, preferably there are 1, 2, 3 or 4 heteroatom substituents selected from the group consisting of oxygen, nitrogen and/or halogen. Preferred substituent groups are independently selected from hydroxy, acyl, acyloxy, nitro, amino, $SO_3H$, SH, SW, wherein R' is independently selected from the same groups as R; carboxyl, cyano, ($C_1$-$C_6$)alkylamino, ($C_1$-$C_6$)dialkylamino, thiol, chloro, bromo, fluoro and iodo.

Furthermore, the compounds of this invention contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The compounds of this invention may contain one or more asymmetric centers, depending upon the location and nature of the various substituents desired. Asymmetric carbon atoms or phosphorous atoms may be present in the (R) or (S) configuration or (R,S) configuration. In certain instances, asymmetry may also be present due to restricted rotation about a given bond, for example, the central bond adjoining two substituted aromatic rings of the specified compounds. Substituents on a ring may also be present in either cis or trans form, and a substituent on a double bond may be present in either Z or E form. It is intended that all such configurations (including enantiomers and diastereomers) are included within the scope of the present invention. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like, also well-known in the art and exemplified the experimental examples below. Separated, pure or partially purified isomers or racemic mixtures of the compounds of this invention are also included within the scope of the present invention.

Preferred compounds are those with the absolute configuration of the compound of this invention which produces the more desirable biological activity.

The term "pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "pharmaceutically acceptable partial salts" is included in the term "pharmaceutically acceptable salts" and refers to compounds having a substituent capable of having more than one group form a salt but less than the maximum amount of such groups actually form a salt. For example, a diphospho group can form a plurality of salts and, if only partially ionized, the resulting group is sometimes referred to herein as a partial salt. It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl. Similarly, it is understood that the above definitions are not intended to include impermissible substitution patterns (e.g., methyl substituted with 5 fluoro groups or a hydroxyl group pendent to a carbon atom of an ethenylic or acetylenic unsaturation). Such impermissible substitution patterns are well known to the skilled artisan.

When a compound is depicted as a charged species, e.g.,

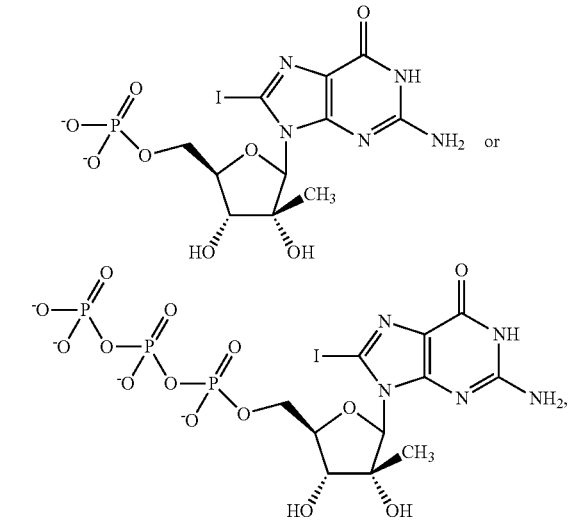

it is to be understood that the compound is in a salt form, and exists together with the appropriate number of pharmaceutically acceptable counter ions, as described above, as required to produce a neutral species.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4th Edition), and Larock's *Comprehensive Organic Transformations* (VCH Publishers Inc., 1989). Specifically, the compounds of this invention may be prepared by various methods known in the art of organic chemistry in general and nucleoside and nucleotide analogue synthesis in particular.

General reviews of the preparation of nucleoside and nucleotide analogues include 1) Michelson A. M., "*The Chemistry of Nucleosides and Nucleotides*," Academic Press, New York, 1963; 2) Goodman L., "*Basic Principles in Nucleic Acid Chemistry*," Academic Press, New York, 1974, vol. 1, Ch. 2; and 3) "*Synthetic Procedures in Nucleic Acid Chemistry*," Eds. Zorbach W. & Tipson R., Wiley, New York, 1973, vol. 1 & 2.

Strategies available for synthesis of compounds of this invention are illustrated in the synthetic schemes below.

Reaction Scheme 1

Step 1:

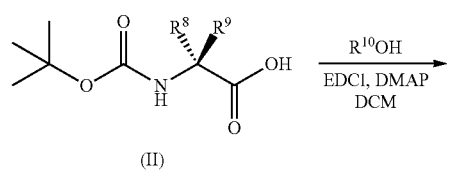

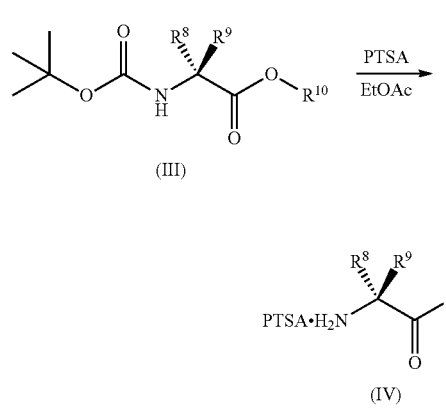

Step 2:

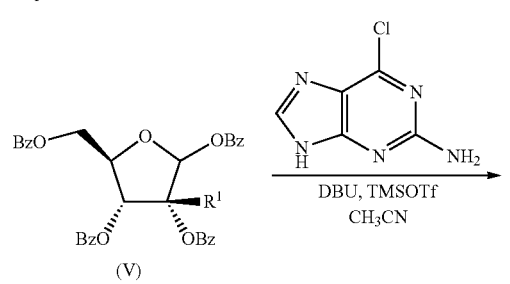

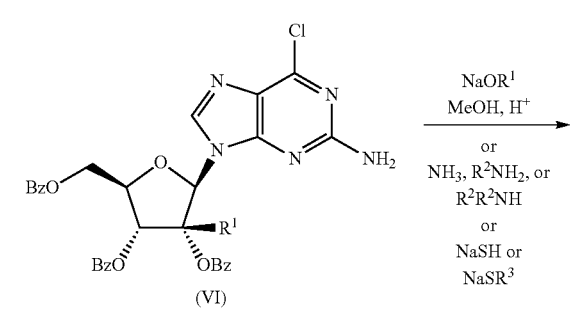

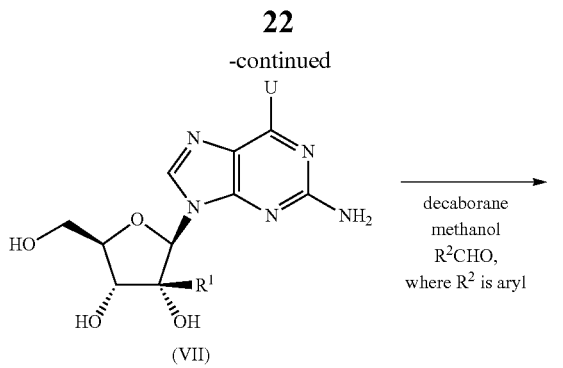

Step 3:

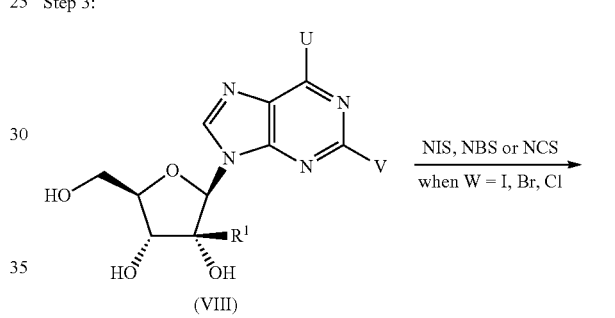

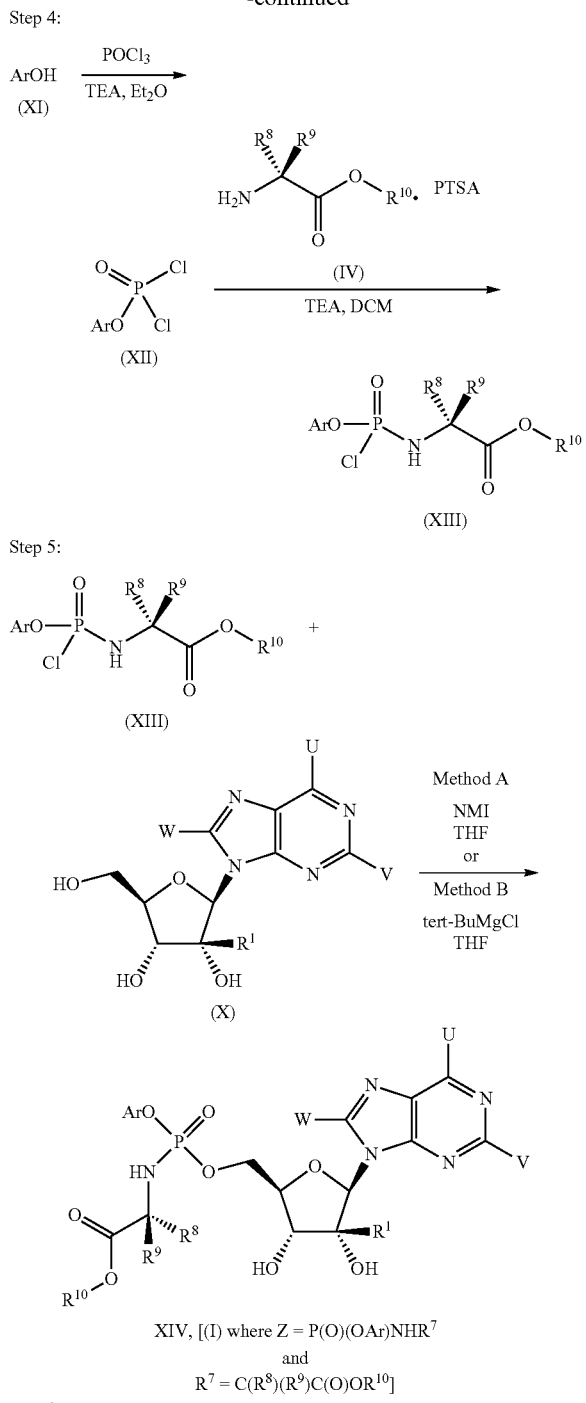

organic acid such as PTSA in a suitable solvent such as ethyl acetate. Alternatively the BOC group can be removed with other acids such as trifluoroacetic acid and hydrochloric acid (HCl) which provide the corresponding TFA or HCl salts.

In Step 2, the protected sugar derivative of formula (V) is allowed to react with the 2-amino-6-chloropurine, using a non-nucleophilic base such as DBU, and a Lewis acid such as TMS triflate in a polar solvent such as acetonitrile, to produce the compound of formula (VI). This reaction can be done at 0° C. to 100° C., but most preferably at 60° C. Alternatively, other nucleoside coupling reagents such as BSA/SnCl$_4$, or HMDS/TMSOTf can be used either with or with prior persilylation. Alternatively other know nucleoside coupling reagents, as described in the Handbook of Nucleoside Synthesis by Helmut Vorbruggen and Carmen Ruh-Pohlenz (John Wiley & Sons, Copyright 2001 by Organic Reactions) can be used. The nucleoside coupling reaction can be carried out in other polar or non-polar aprotic solvents such as, but not limited to, dichloroethane, toluene, o-, m-, or p-xylene or DCM. Displacement of the chlorine attached to the purine portion of the molecule by an oxygen nucleophile is carried out using an alkoxide such as ($R^1$—) using the parent alcohol ($R^1OH$) as solvent, to produce the formula (VII) intermediate where U is $OR^1$. Compounds of formula (VII), where U is $NH_2$, $NHR^2$, or $NR^2R^2$, are similarly prepared by reaction of (VI) with ammonia or a nitrogen nucleophile of formula $R^2NH_2$, or $R^2R^2NH_2$. These reactions can be done with the nitrogen nucleophile as the solvent, or with ammonia or a nitrogen nucleophile. as a reagent in a solvent such as, but not limited to, ethanol, isopropanol, THF, acetonitrile, or DMF. Compounds of formula (VII), where U is SH, or $SR^3$, are similarly prepared by reaction of (VI) with a sulfur nucleophile of formula $R^3SH$. These reactions can be done with the $R^3SH$ as the solvent, or with $R^3SH$ as a reagent in a solvent such as, but not limited to ethanol, isopropanol, THF, acetonitrile, or DMF.

Conversion to the formula (VIII) compound where V=$R^2NH$, is carried out by reductive amination in which an arylaldehyde, optionally substituted by halo on the aryl portion, is allowed to react with the formula (VII) compound in the presence of a selective reducing agent such as decaborane in a protic solvent such as methanol. This reaction can be run at 0° C. to 100° C. and most optimally at −25° C. Alternatively, other reducing agents can be used such as sodium cyanoborohydride or sodium borohydride, or other reductive amination reagents as described in "Comprehensive Organic Synthesis" Eds. B. M. Trost and I. Fleming, Pergamon, Oxford (1991), Vol 8, Part 1.2 p 25. In Step 3 of Reaction Scheme 1, compounds of formula (VIII) are converted to compounds of formula (IX) using halogenation conditions familiar to those skilled in the art. Specifically, N-iodosuccinimide (NIS), N-bromosuccinimide, or N-chlorosuccinimide can be used in polar aprotic solvents such as ether, or preferably THF to synthesize the C-8 iodo, C-8 bromo, or C-8 chloro derivatives. Compounds of the formula (VIII) where U is $NH_2$, $NHR^2$, or $NR^2R^2$, can be converted to compounds of formula (IX) following general procedures described in the literature and familiar to one skilled in the art (for example: Synthesis and properties of 2,6-diamino-8,2′-anhydro-8-mer- In step 1 of Reaction Scheme 1, a protected amino acid of general formula (II) is esterified with an alcohol of formula $R^{10}OH$, facilitated by addition of such reagents as EDCI and DMAP, and carried out in an inert solvent such as dichloromethane, to produce the compound of formula (III). Alternatively, many other commonly used ester forming reagents such as DCC/DMAP, trifluoroacetic anhydride, N,N′-carbonyldiimidazole and PPh$_3$/CCl$_4$ can be used. Removal of the BOC protecting group from compound (IV) and conversion to a salt of formula IV) is carried out by its reaction with an capto-9-β-D-arabinofuranosylpurine, Muraoka, Masako Chemical & Pharmaceutical Bulletin (1981), 29(12), 3449-54).

Further, compounds of formula (IX) can be converted to compounds of formula (X) either by direct displacement reactions using $R^5OH$, $R^4SH$, $R^6NH_2$, or $R^6R^6NH$ as the nucleophile in the optional presence of a base, or by employing transition metal chemistry. (i.e., Buchwald coupling) using $R^6NH_2$, or $R^6R^6NH$, a strong base, and an appropriate catalyst such as $PdCl_2(P(o-tolyl)_3)_2$, and conditions familiar to one skilled in the art. (See John P. Wolfe and Stephen L. Buchwald (2004), "Palladium-Catalyzed Amination Of Aryl Halides And Aryl Triflates", Org. Synth., Coll. Vol. 10: 423)

In Step 4 of Reaction Scheme I, the aryl chloroamidate of formula (XIII) is prepared by reaction of the hydroxylated aryl compound of formula (XI) with phosphorous oxychloride in the presence of a non-nucleophilic base such as triethylamine, to provide the intermediate of formula (XII). This reaction can be run in an aprotic solvent such as DCM, ether or MTBE and at low temperatures, preferably 0° C. to −78° C. and preferably at −25° C. In addition to triethyl amine, many other non-nucleophilic bases can be used such as DIEA or DBU. The product of this reaction can be used directly in the next reaction, or the amine salts generated in the reaction, such as triethyl ammonium hydrochloride, can be filtered off prior to the next step. The reaction should be protected from moisture at all times, as the phosphorodichloridate product, is very moisture sensitive. Subsequent reaction of (XII) with the amino ester salt of formula (IV) is carried out in the presence of a base to produce the compound of formula (XIII). This reaction can be done at 0° C. to −78° C., and preferably at −25° C. A variety of non-polar aprotic solvents may be used such as ether, MTBE, and DCM. The base may be selected from a wide variety on non-nucleophilic organic amines such as, but not limited to, TEA, DIEA, or DBU. This reaction must be protected from moisture at all times. Upon completion of the reaction it is critical to remove the corresponding organic amine salts, such as triethyl ammonium hydrochloride, or triethyl ammonium p-toluene sulfonic acid. This can be accomplished by concentrating the reaction mixture and precipitating the salt with EtOAc and Hexanes and filtering them off, or by passing the crude product through a silica gel plug. Removal of solvents during the work up must be done at temperatures at or below 25° C. to avoid decomposition of the phosphorochloridate.

In Step 5, coupling of the formula (XIII) and formula (VIII) or formula (IX), or formula (X) compounds to provide the compound of formula (XIV) is carried out using an nucleophilic catalyst such as NMI in an inert organic solvent such as THF. Other nucleophilic catalysts such as DMAP, trimethylamine, pyridine, or 4-(pyrrolidin-1-yl)pyridine, can be used as well as other aprotic solvents such as diethyl ether, MTBE chloroform or DCM. These reactions can be carried out between 0° C. and 50° C., and preferably at 25° C. Alternatively a strong non-nucleophilic base, e.g., tert-butyl magnesium chloride can be used in a solvent such as THF, or diethyl ether, or MTBE. Other strong proton selective organic or inorganic bases can be used such as n-butyl lithium, potassium tert-butoxide, 2,4,6-collidine, DBU, or lithium bis(trimethylsilyl)amide. This reaction can be carried out at −78° C. to 40° C. and preferably at 0-25° C.

Reaction Scheme 2 illustrates the synthesis of the guanine derivatives from the corresponding $O^6$-methyl derivatives.

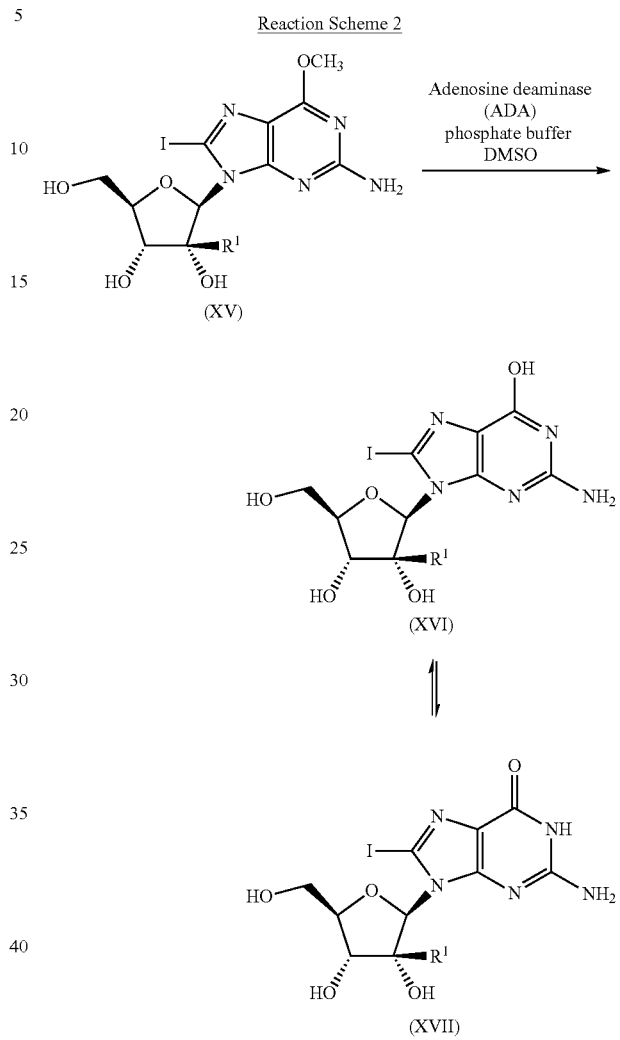

Conversion of the $O^6$ methyl derivatives of formula (XV) to the guanine derivatives of formula (XVI) and its tautomer of formula (XVII) can be effected using chemistry described in the literature such as M. J. Robins, R. Zou, F. Hansske, S. F. Wnuk Can. J. Chem. (1997), vol 75, pgs 762-767. Alternatively, the $O^6$-methyl group of the formula (XV) compound can be removed with TMSI either directly or generated in situ with TMSCl and NaI, in the presence of a base such as DMAP or diethylisopropylamine in an aprotic polar solvent such as acetonitrile.

Reaction Scheme 3 illustrates the synthesis of the monophosphate and triphosphate derivatives starting from the compound of formula (XVII); Treatment of (XVII) with $POCl_3$ provides the compound of formula (XVIII) after aqueous workup, alternatively treatment with pyrophosphate provides the triphosphate of formula (XIX) after aqueous workup. These compounds have additional utility as analytical markers in in vivo studies.

Reaction Scheme 3

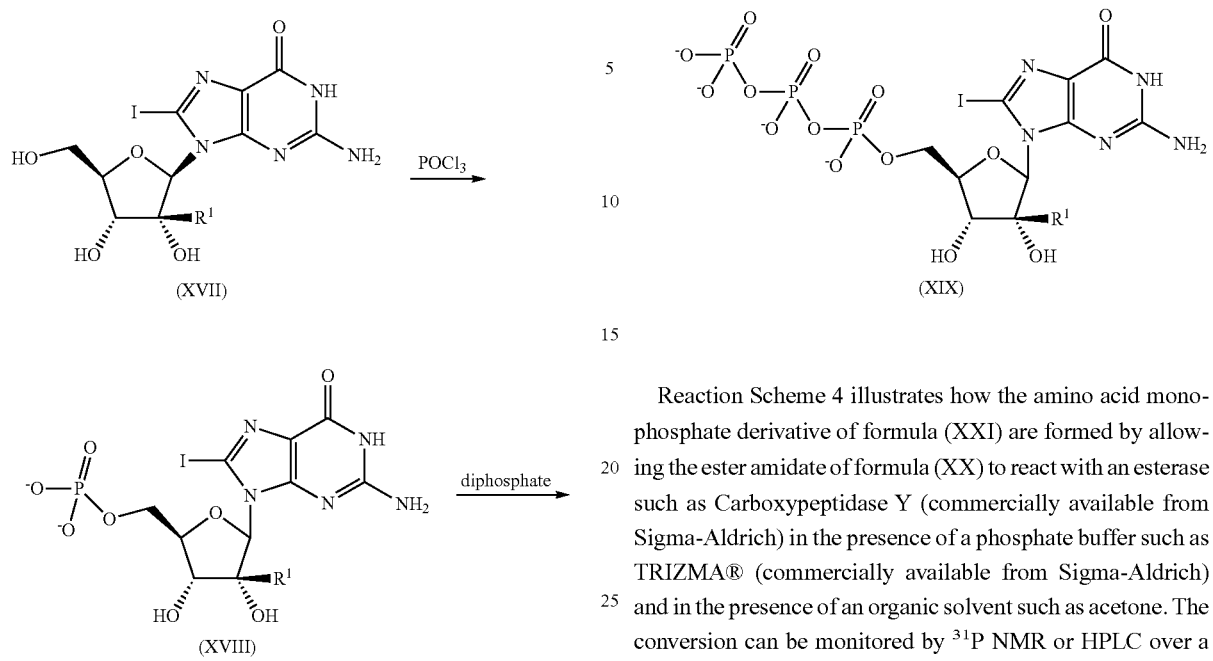

Reaction Scheme 4 illustrates how the amino acid monophosphate derivative of formula (XXI) are formed by allowing the ester amidate of formula (XX) to react with an esterase such as Carboxypeptidase Y (commercially available from Sigma-Aldrich) in the presence of a phosphate buffer such as TRIZMA® (commercially available from Sigma-Aldrich) and in the presence of an organic solvent such as acetone. The conversion can be monitored by $^{31}$P NMR or HPLC over a period of 5-24 hours.

Reaction Scheme 4

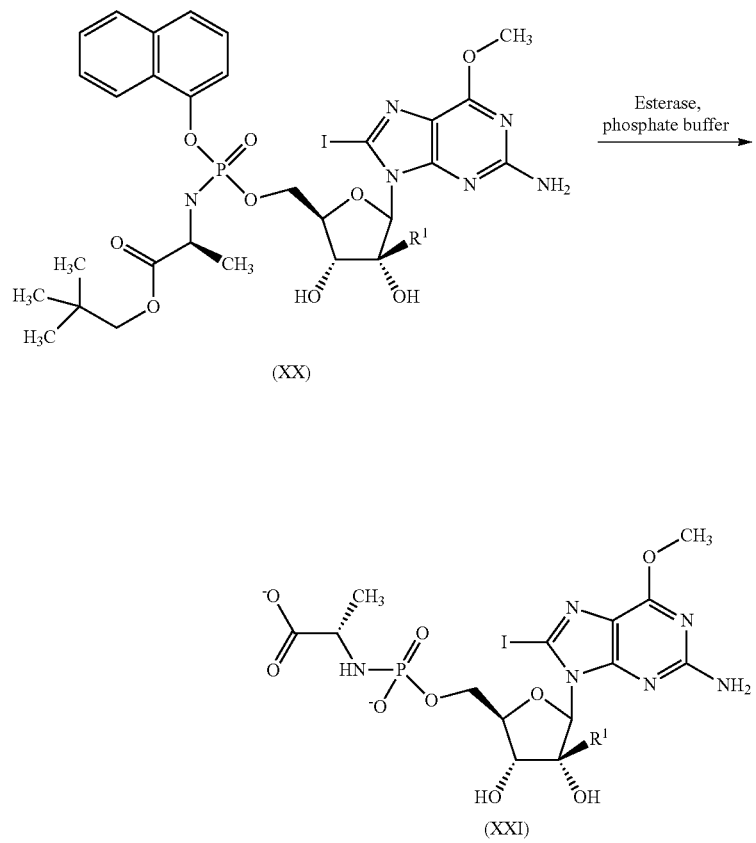

The invention contemplates the compound as set forth above wherein the compound includes a mixture of two phosphorous diastereomers in any proportion from 1:99 to 99:1. A method of separating the phosphorous diastereomers of the present compounds is also contemplated wherein the separation is conducted using a chiral chromatographic step performed on a chiral resin.

Phosphorous diastereomers of formula (I) (e.g., the compound of formula (XIV) as produced in Reaction Scheme 1) can be separated using chiral chromatography as shown in Reaction Scheme 5.

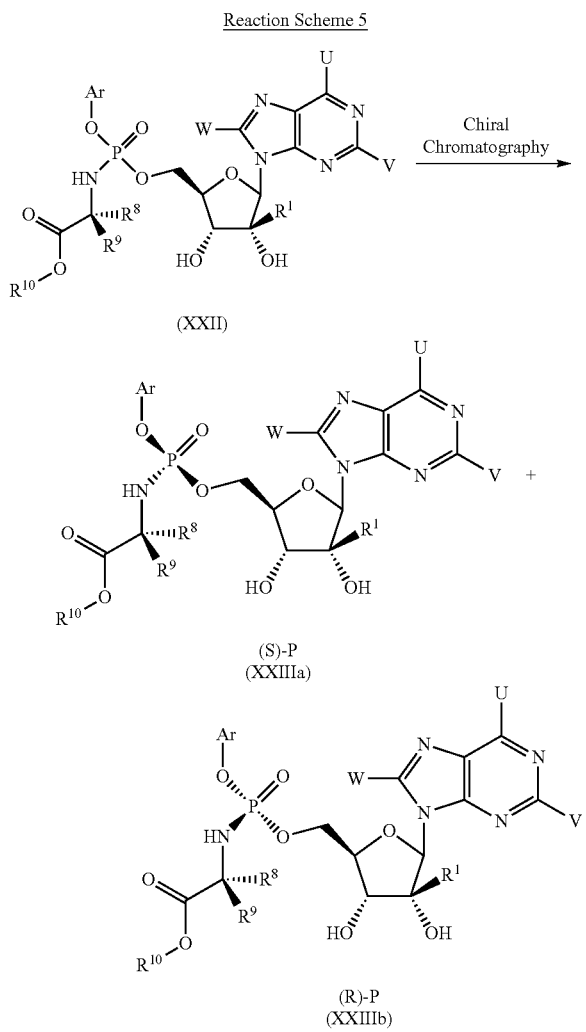

In this Scheme, the chiral chromatography can be performed on a variety of different chiral resins such as CHIRALPAK AD®, CHIRALPAK AS®, CHIRALCEL OD®, CHIRALCEL OJ®, CHIRALCEL OB®, and CHIRALCEL OC® AD-H®, AS-H®, OD-H®, OJ-H®, OB-H® and OC-H®. Alternatively the chiral resin could be selected from the list below:
CHIRALPAK® IAT™
CHIRALPAK® IA-3
CHIRALPAK® AD-H
CHIRALPAK® AD
CHIRALPAK® AD-3
CHIRALPAK® AD-3R
CHIRALPAK® AS-H
CHIRALPAK® AS
CHIRALPAK® AY-H
CHIRALPAK® AY
CHIRALPAK® AZ-H
CHIRALPAK® AZ
CHIRALPAK® IB™
CHIRALCEL® OD-H
CHIRALCEL® OD
CHIRALCEL® OD-3
CHIRALCEL® OD-3R
CHIRALCEL® OD-I
CHIRALPAK® IC™
CHIRALPAK® IC-3
CHIRALCEL® OC-H
CHIRALCEL® OC
CHIRALCEL® OA
CHIRALCEL® OB-H
CHIRALCEL® OB
CHIRALCEL® OG
CHIRALCEL® OJ-H
CHIRALCEL® OJ
CHIRALCEL® OF
CHIRALCEL® OK
CHIRALCEL® OZ-H
CHIRALCEL® OZ Optimally a Chiral Pak AD column can be used with a mixture of 1:1 ethanol:hexanes as the mobile phase. Other solvents such as ethyl acetate, isopropanol, acetonitrile, and methanol can be used as the mobile phase, or other solvents familiar to those skilled in the art.

Reaction Scheme 6 illustrates the synthesis of symmetrical phosphorodiamidates from nucleoside derivatives of formula (XXIV).

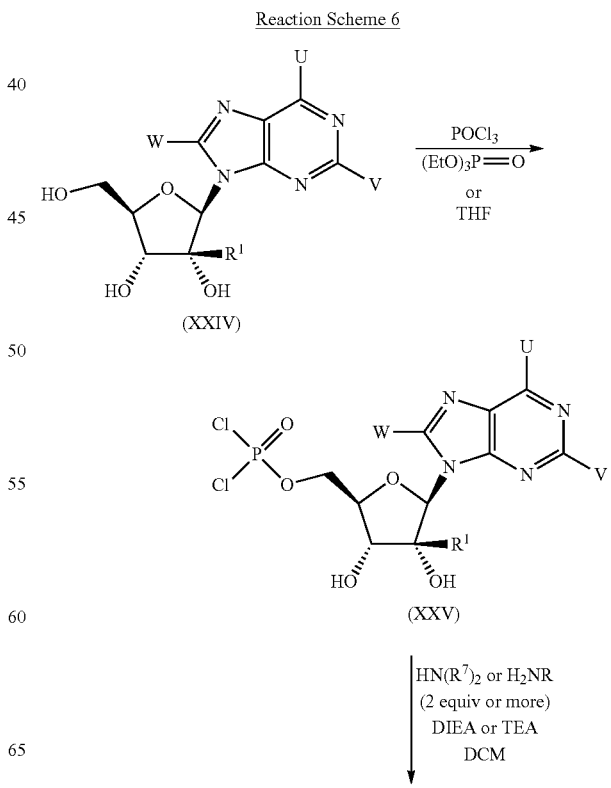

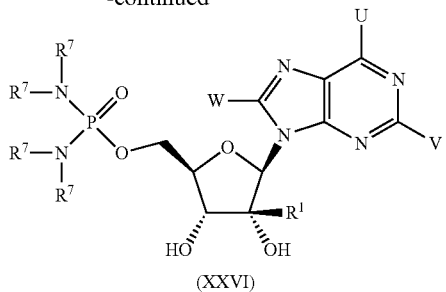

(XXVI)

In this scheme, nucleosides of the formula (XXIV), [e.g. nucleosides of formula (X) where Y=H, $X^1$ and $X^2$=OH, prepared as described Reaction Scheme 1], or in International Application PCT/US10/20632 are dissolved in a neutral aprotic solvent such as THF or triethyl phosphate or similar solvent and cooled to below ambient temperature, preferably to 0-5° C. Phosphorus oxychloride (phosphoryl chloride) of high quality is added to the solution with careful protection from moisture. The reaction is stirred for 1-48 h at temperatures from −20° C. to 20° C. and optimally for 24 h at 5° C. forming compounds of the formula (XXV). The solution is diluted with an aprotic solvent, preferably DCM, and a primary or secondary amine, of formula $R^7NH_2$ or $(R^7)_2NH$, where each $R^7$ may be the same or different, as defined above. These include such primary or secondary amines as the HCl or tosylate salt of an amino acid ester. The addition of the amine is carried out at reduced temperatures of from about −78° C. to about 5° C. and preferably at about 0° C. This is followed by the addition of a non-nucleophilic base such as a tertiary amine such as triethylamine, or preferably diisopropylethylamine. The solution is stirred for about 1 h to about 10 days at reduced temperatures and preferably at about 5° C. for about 5 days, forming phosphodiamidate (XXVI).

Alternatively the nucleoside (XVI) can be dissolved in a neutral aprotic solvent such as THF or triethyl phosphate or similar solvent, but preferably THF, and a non-nucleophilic base such as a tertiary amine or diisopropylethylamine or preferably triethylamine is added and stirred for a period of about 5 min to about 1 h, preferably about 30 min. The solution is then cooled to about −100° C. to rt, or preferably about −78° C., and phosphorus oxychloride (phosphoryl chloride) of high quality is added slowly to the solution with careful protection from moisture. The reaction is stirred for about 5 min to about 2 h at temperatures from about −100° C. to about 0° C. and optimally for about 30 min at about −78° C., then warmed to ambient temperature for about 5 min to about 2 h, preferably about 30 min forming compound (XVII). The solution is further diluted with an aprotic solvent, preferably DCM, and a primary or secondary amine, such as the HCl or tosylate salt of an amino acid ester, is added followed by the addition of a non-nucleophilic base such as a tertiary amine preferably triethylamine at reduced temperatures of about −78° C. to about 5° C. and preferably at about −78° C. The solution is warmed to ambient temperature and stirred for about 1 h to about 48 h, preferably about 24 h, forming phosphodiamidate (XVIII). The reaction can be worked up using standard methods familiar to one skilled in the art, for example extraction with a sodium chloride solution, drying with sodium sulfate and purification by silica gel chromatography. Changes to this procedure including solvent switches and optimization of the temperature, familiar to those skilled in the art of organic chemistry would be anticipated.

Reaction Scheme 7 illustrates a general method of preparation of asymmetrical phosphoramidates.

Reaction Scheme 7

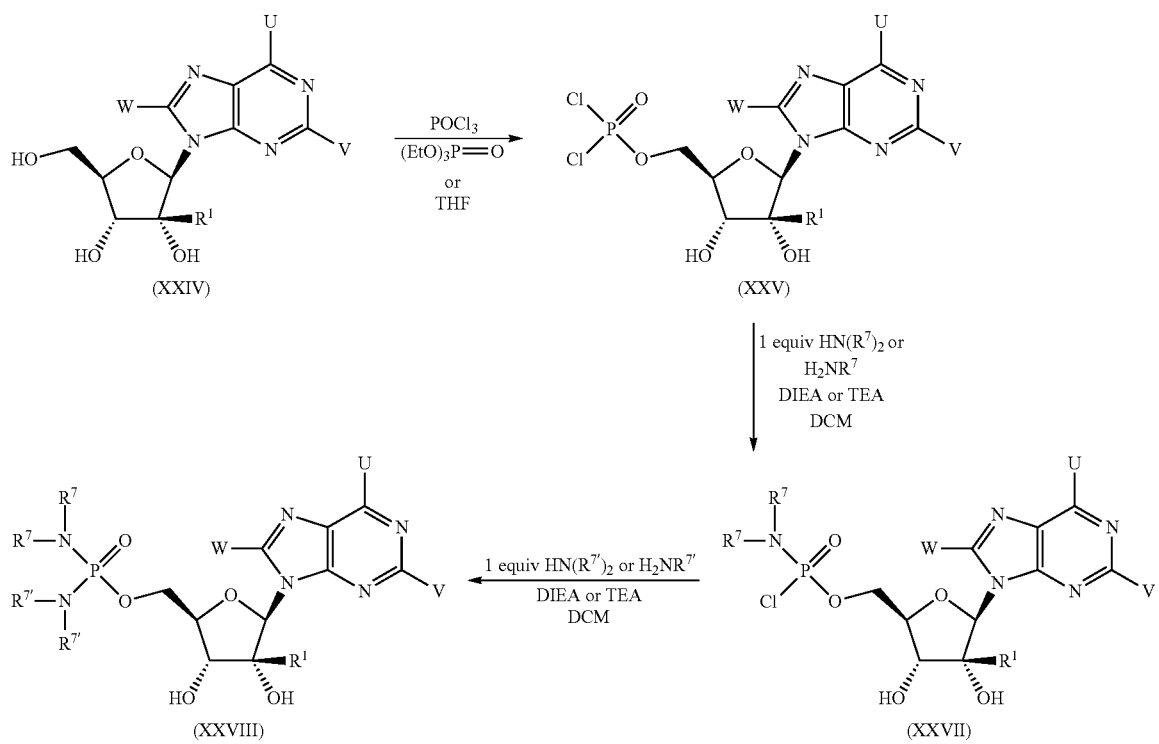

In this scheme a general method for synthesizing asymmetrical phosphordiamidates is described. The nucleoside (XXIV) can be dissolved in a neutral aprotic solvent such as THF or triethyl phosphate or similar solvent, but preferably THF, and a non-nucleophilic base such as a tertiary amine or diisopropylethylamine or preferably triethylamine is added and stirred for a period of about 5 min to about 1 h, preferably about 30 min. The solution is then cooled to about −100° C. to rt, or preferably about −78° C., and phosphorus oxychloride (phosphoryl chloride) of high quality is added slowly to the solution with careful protection from moisture. The reaction is stirred for about 5 min to about 2 h at temperatures ranging from about −100° C. to about 0° C. and optimally for about 30 min at about −78° C., then warmed to ambient temperature for about 5 min to about 2 h, preferably about 30 min forming compound (XXV). The solution is further diluted with an aprotic solvent, preferably DCM, and one equivalent of a primary or secondary amine of formula $R^7NH_2$ or $(R^7)_2NH$, where each $R^7$ may be the same or different, as defined above, is added. The primary or secondary amine includes a HCl or tosylate salt of an amino acid ester. Addition of the amine is followed by the addition of a non-nucleophilic base such as a tertiary amine, preferably triethylamine at reduced temperatures of about −78° C. to about 5° C. and preferably at about −78° C. The solution is warmed to ambient temperature and stirred for about 1 h to about 48 h, preferably about 24 h, forming the compound of formula (XXVII). A phosphorus NMR can be acquired to determine the status of the reaction.

The solution is then cooled to about −100° C. to rt, or preferably −78° C. One to 10 equivalents, preferably 5 equivalents, of a primary or secondary amine of formula $R^{7'}NH_2$ or $(R^{7'})_2NH$, is added, where $R^{7'}$ is as defined above for $R^7$, and each $R^{7'}$ may be the same or different. The primary or secondary amine includes a HCl or tosylate salt of an amino acid ester, such as the HCl or tosylate salt of an amino acid ester. This is followed by the addition of an excess of a non-nucleophilic base such as a tertiary amine, preferably triethylamine (5-10 equivalents) at reduced temperatures of about −78° C. to about 5° C. and preferably at about −78° C. The solution is warmed to ambient temperature and stirred for about 1 h to about 48 h, preferably about 24 h, forming phosphodiamidate (XXVIII). The reaction is worked up using standard methods familiar to one skilled in the art, for example extraction with a sodium chloride solution, drying with sodium sulfate and purification by silica gel chromatography.

It is to be understood that each of the $R^7$ or $R^{7'}$ may be the same or different and are independently selected from the $R^7$ groups as defined above for formula (I). It is also to be understood that changes to this procedure, including solvent switches and optimization of the temperature, familiar to those skilled in the art of organic chemistry, can be made and are anticipated.

Reaction Scheme 8 illustrates an alternative method for synthesizing asymmetrical phosphordiamidates.

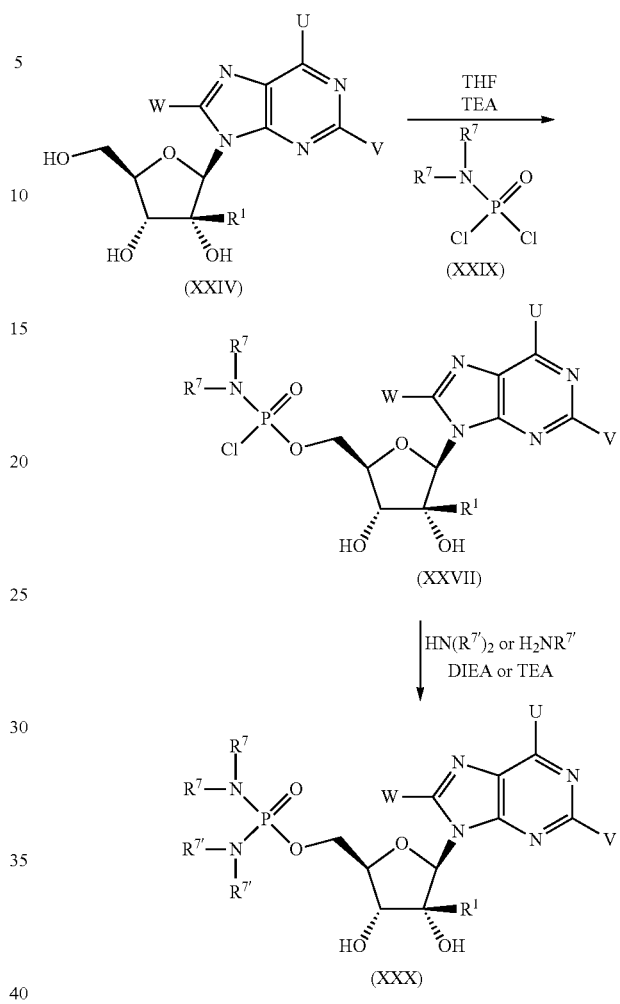

Reaction Scheme 8

This scheme describes a second general method for synthesizing asymmetrical phosphorodiamidates. The nucleoside (XXIV) can be dissolved in a neutral aprotic solvent such as THF or triethyl phosphate or similar solvent, but preferably THF. A non-nucleophilic base such as a tertiary amine or diisopropylethylamine or preferably triethylamine is added in excess, preferably 1.2 equivalents. The solution can be stirred at ambient temperature and 1 to 3 equivalents of an amino acid ester dichloridate (XXIX), can be added. Compounds of the general structure (XXIX) can be synthesized using techniques familiar to one skilled in the art. A phosphorus NMR can be acquired to determine the status of the formation of the compound of formula (XXVII) The solution is then cooled to −100° C. to rt, or preferably −78° C., and 1 to 10 equivalents, preferably 5 equivalents, of a primary or secondary amine of formula $R^{7'}NH_2$ or $(R^{7'})_2NH$ are added, where $R^{7'}$ is as defined above for $R^7$, and each $R^{7'}$ may be the same or different. The solution is warmed to ambient temperature and stirred for 1 h to 48 h, preferably 24 h, forming phosphodiamidate (I). The reaction is worked up using standard methods familiar to one skilled in the art, for example extraction with a sodium chloride solution, drying with sodium sulfate and purification by silica gel chromatography.

It is to be understood that each of the $R^7$ or $R^{7'}$ may be the same or different and are independently selected from the $R^7$ groups as defined above for formula (I). It is also to be understood that changes to this procedure, including solvent switches and optimization of the temperature, familiar to those skilled in the art of organic chemistry, can be made and are anticipated.

The general schemes above are preferably carried out in the presence of a suitable solvent. Suitable solvents include hydrocarbon solvents such as benzene and toluene; ether type solvents such as diethyl ether, tetrahydrofuran, diphenyl ether, anisole and dimethoxybenzene; halogenated hydrocarbon solvents such as methylene chloride, chloroform and chlorobenzene; ketone type solvents such as acetone, methyl ethyl ketone and methyl isobutyl ketone; alcohol type solvents such as methanol, ethanol, propanol, isopropanol, n-butyl alcohol and tert-butyl alcohol; nitrile type solvents such as acetonitiile, propionitrile and benzonitrile; ester type solvents such as ethyl acetate and butyl acetate; carbonate type solvents such as ethylene carbonate and propylene carbonate; and the like. These may be used singly or two or more of them may be used in admixture. Preferably an inert solvent is used in the process of the present invention. The term "inert solvent" means a solvent inert under the conditions of the reaction being described in conjunction therewith including, for example, benzene, toluene, acetonitrile, tetrahydrofuran, dimethylformamide, chloroform, methylene chloride (or dichloromethane), diethyl ether, ethyl acetate, acetone, methylethyl ketone, methanol, ethanol, propanol, isopropanol, tert-butanol, dioxane, pyridine, and the like.

Dosages and Routes of Administration.

In general, the compounds of this invention will be administered in a method wherein a therapeutically effective amount of the compounds (or a pharmaceutical composition comprising the compound and a pharmaceutically acceptable carrier, excipient or diluent). is administered to a mammal in need thereof by any of the accepted modes of administration for agents that serve similar utilities. The effective amount will be that amount of the compound of this invention that would be understood by one skilled in the art to provide therapeutic benefits, i.e., the active ingredient, and will thus depend upon numerous factors such as the severity of the disease to be treated, the age, size and relative health of the subject, the potency of the compound used, the route and form of administration, and other factors. The drug can be administered more than once a day, and in the preferred mode the drug is administered once or twice a day. As indicated above, all of the factors to be considered in determining the effective amount will be well within the skill of the attending clinician or other health care professional.

For example, therapeutically effective amounts of compounds of formula (I) may range from approximately 0.05 to 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-700 mg per day. In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract (see U.S. Pat. No. 5,607,915, said patent incorporated herein by reference).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Previously, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability. These patents are incorporated herein by reference.

As indicated above, the compositions in accordance with the invention generally comprise a compound of formula (I) in combination with at least one pharmaceutically acceptable carrier, excipient or diluent. Some examples of acceptable excipients are those that are non-toxic, will aid administration, and do not adversely affect the therapeutic benefit of the compound of the invention. Such excipient may be any solid, liquid, semi-solid or, in the case of an aerosol composition, gaseous excipient that is generally available to one of skill in the art.

Solid pharmaceutical excipients useful in the invention may include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990). The amount of the compound in a formulation can vary within the full range employed by those skilled in the art. For example, the formulation will contain, on a weight percent (wt %) basis, from about 0.01-99.99 wt % wherein the compound is a compound of formula (I) based on the total formulation, with the balance being one or more suitable pharmaceutical excipients. Preferably, the compound is present at a level of about 1-80 wt %. Pharmaceutical formulations containing a compound in accordance with the invention are described further below.

Additionally, the present invention is directed to a pharmaceutical composition comprising a therapeutically effective amount of a compound of the present invention in combination with a therapeutically effective amount of another active agent against RNA-dependent RNA virus and, in particular, against HCV. Agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffman-LaRoche, Nutley, N.J.), interferon-α2b (such as Intron-A interferon available from Schering Corp., Kenilworth, N.J., USA), a consensus interferon, and a purified interferon-α product. For a discussion of ribavirin and its activity against HCV, see J. O. Saunders and S. A. Raybuck, "Inosine Monophosphate Dehydrogenase: Consideration of Structure, Kinetics and Therapeutic Potential," *Ann. Rep. Med. Chem.*, 35:201-210 (2000).

Even further, the present invention is directed to a pharmaceutical composition comprising a therapeutically effective amount of a compound of the present invention in combination with a therapeutically effective amount of another agent active against hepatitis C virus. Such agents include those that inhibit HCV proteases, HCV polymerase, HCV helicase, HCV NS4B protein, HCV entry, HCV assembly, HCV egress, HCV NS5A protein, and inosine 5'-monophosphate dehydrogenase. Other agents include nucleoside analogs for the treatment of an HCV infection. Still other compounds include those disclosed in WO 2004/014313 and WO 2004/014852 and in the references cited therein. The patent applications WO 2004/014313 and WO 2004/014852 are hereby incorporated by references in their entirety. Specific antiviral agents include Omega IFN (BioMedicines Inc.), BILN-2061 (Boehringer Ingelheim), Summetrel (Endo Pharmaceuticals Holdings Inc.), Roferon A (F. Hoffman-La Roche), Pegasys (F. Hoffman-La Roche), Pegasys/Ribaravin (F. Hoffman-La Roche), CellCept (F. Hoffman-La Roche), Wellferon (GlaxoSmithKline), Albuferon-α (Human Genome Sciences Inc.), Levovirin (ICN Pharmaceuticals), IDN-6556 (Idun Pharmaceuticals), IP-501 (Indevus Pharmaceuticals), Actimmune (InterMune Inc.), Infergen A (InterMune Inc.), ISIS 14803 (ISIS Pharmaceuticals Inc.), JTK-003 (Japan Tobacco Inc.), Pegasys/Ceplene (Maxim Pharmaceuticals), Ceplene (Maxim Pharmaceuticals), Civacir (Nabi Biopharmaceuticals Inc.), Intron A/Zadaxin (RegeneRx), Levovirin (Ribapharm Inc.), Viramidine (Ribapharm Inc.), Heptazyme (Ribozyme Pharmaceuticals), Intron A (Schering-Plough), PEG-Intron (Schering-Plough), Rebetron (Schering-Plough), Ribavirin (Schering-Plough), PEG-Intron/Ribavirin (Schering-Plough), Zadazim (SciClone), Rebif (Serono), IFN-β/EMZ701 (Transition Therapeutics), T67 (Tularik Inc.), VX-497 (Vertex Pharmaceuticals Inc.), VX-950/LY-5703 10 (Vertex Pharmaceuticals Inc.), Omniferon (Viragen Inc.), XTL-002 (XTL Biopharmaceuticals), SCH 503034 (Schering-Plough), isatoribine and its prodrugs ANA971 and ANA975 (Anadys), R1479 (Roche Biosciences), Valopicitabine (Idenix), NIM811 (Novartis), and Actilon (Coley Pharmaceuticals).

In some embodiments, the compositions and methods of the present invention contain a compound of formula (I) and interferon. In some aspects, the interferon is selected from the group consisting of interferon alpha 2B, pegylated interferon alpha, consensus interferon, interferon alpha 2A, and lymphoblastoid interferon tau.

In other embodiments the compositions and methods of the present invention utilize a combination of a compound of formula (I) and a compound having anti-HCV activity such as those selected from the group consisting of interleukin 2, interleukin 6, interleukin 12, a compound that enhances the development of a type 1 helper T cell response, interfering RNA, anti-sense RNA, Imiqimod, ribavirin, an inosine 5' monophospate dehydrogenase inhibitor, amantadine, and rimantadine.

Anti-Hepatitis C Activity Assays

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture was disclosed in U.S. Pat. No. 5,738,985 to Miles et al. In vitro assays have been reported in Ferrari et al. *J. of Vir.*, 73:1649-1654, 1999; Ishii et al., *Hepatology*, 29:1227-1235, 1999; Lohmann et al., *J. Bio. Chem.*, 274:10807-10815, 1999; and Yamashita et al., *J. of Bio. Chem.*, 273:15479-15486, 1998.

WO 97/12033 relates to HCV polymerase assay that can be used to evaluate the activity of the of the compounds described herein. Another HCV polymerase assay has been reported by Bartholomeusz, et al., Hepatitis C Virus (HCV) RNA polymerase assay using cloned HCV non-structural proteins; Antiviral Therapy 1996:1 (Supp 4) 18-24.

Screens that measure reductions in kinase activity from HCV drugs were disclosed in U.S. Pat. No. 6,030,785, to Katze et al., U.S. Pat. No. 6,228,576, Delvecchio, and U.S. Pat. No. 5,759,795 to Jubin et al. Screens that measure the protease inhibiting activity of proposed HCV drugs were disclosed in U.S. Pat. No. 5,861,267 to Su et al., U.S. Pat. No. 5,739,002 to De Francesco et al., and U.S. Pat. No. 5,597,691 to Houghton et al. All of said patents are incorporated herein by reference.

EXAMPLES

Embodiments of the present invention will now be described by way of example only with respect to the following non-limiting examples.

General Procedures

All experiments involving water-sensitive compounds were conducted under scrupulously dry conditions. Anhydrous tetrahydrofuran (THF) and dichloromethane were purchased from Aldrich and used directly. The sugar derivative (2S,3R,4R,5R)-5-(benzoyloxymethyl)-3-methyltetrahydrofuran-2,3,4-triyl tribenzoate or equivalently: 2,3,4,5-tetra-O-benzoyl-2-C-methyl-β-D-ribofuranose was purchased from CarboSynth Limited, 8&9 Old Station Business Park, Compton, Berkshire, RG20 6NE, UK. The purine derivative 2-amino-6-chloropurine or equivalently, 6-chloro-9H-purin-2-amine, was purchased from Aldrich. 2'-C-Methylguanosine (2-amino-9-((3R,4R,5R)-3,4-dihydroxy-5-(hydroxymethyl)-3-methyltetrahydrofuran-2-yl)-1H-purin-6 (9H)-one) is a commercial reagent and was purchased from CarboSynth Limited, 8&9 Old Station Business Park, Compton, Berkshire, RG20 6NE, UK. Salts of amino acid esters were prepared as described in PCT Int. Appl. (2010), WO 2010081082 A2 20100715. Column chromatography refers to flash column chromatography carried out using Merck silica gel 60 (40-60 μm) as stationary phase. Proton, carbon, and phosphorus nuclear magnetic resonance ($^1$H, $^{13}$C, $^{31}$P NMR) spectra were recorded on Bruker Avance spectrometers operating either at 500, 125, and 202 MHz or at 300, 75, and 121 MHz or a Varian Unity Inova instrument operating at 400, 100, and 161.9 MHz. The solvents used are indicated for each compound. All $^{13}$C and $^{31}$P spectra were recorded proton decoupled. Chemical shifts for $^1$H and $^{13}$C spectra are in parts per million downfield from tetramethylsilane. Coupling constants are referred to as J values. Signal splitting patterns are described as singlet (s), doublet (d), triplet (t), quartet (q), broad signal (br), doublet of doublet (dd), doublet of triplet (dt), or multiplet (m). Chemical shifts for $^{31}$P spectra are in parts per million relative to an external phosphoric acid standard. Some of the proton and carbon NMR signals were split because of the presence of (phosphate)diastereoisomers in the samples. The mode of ionization for mass spectrometry was fast atom bombardment (FAB) using MNOBA (m-nitrobenzyl alcohol) as matrix for some compounds. Electrospray mass spectra were obtained using a Waters LCT time-of-flight mass spectrometer coupled to a Waters M600 HPLC pump. Samples were dissolved in methanol and injected into the solvent stream via a Rheodyne injector. The mobile phase used was methanol at a flow rate of 200 μL/min. The electrospray source was operated at a temperature of 130° C. with a desolvation temperature of 300° C., a capillary voltage of 3 kV, and cone voltage of 30 V. Data were collected in the continuum mode over the mass range 100-2000 amu and processed using Masslynx 4.1 software. Accurate mass measurements were facilitated by the introduction of a single lockmass compound of known elemental composition into the source concurrently with sample.

Example 1

(2R,3R,4R,5R)-2-(2-Amino-6-chloro-9H-purin-9-yl)-5-(benzoyloxymethyl)-3-methyltetrahydrofuran-3,4-diyl Dibenzoate

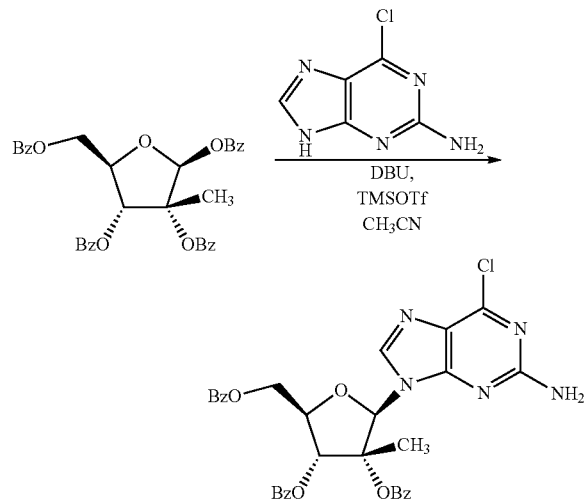

To a pre-cooled (0° C.) solution of (2S,3R,4R,5R)-5-(benzoyloxymethyl)-3-methyltetrahydrofuran-2,3,4-triyl tribenzoate (or 2,3,4,5-tetra-O-benzoyl-2-C-methyl-β-D-ribofuranose) (CarboSynth Ltd, 10.0 g, 17.22 mmol), 2-amino-6-chloropurine (Aldrich, 3.2 g, 18.87 mmol), and 1,8-diazabicycl[5.4.0]undec-7-ene (DBU) (7.7 mL, 51 mmol) in anhydrous acetonitrile (200 mL), was added trimethysilyl triflate (12.5 mL, 68.8 mmol) dropwise. The reaction mixture was then heated at 65° C. for 4 to 6 h, allowed to cool down to room temperature, poured into saturated aqueous sodium bicarbonate (300 mL), and extracted with dichloromethane (3×150 mL). The combined organic phase was dried over sodium sulfate and evaporated under reduced pressure. The residue was precipitated from dichloromethane and methanol, filtrated, the solid was washed 2 times with methanol and dried to give the desired compound (8.5 g, 79%) as a white solid (yields are from 65% (column) up to 90% (precipitation)).

The following are the NMR results analyzing the synthesized compounds:

$^1$H NMR (500 MHz, CDCl$_3$) δ 8.13 (dd, J=1.2, 8.3, 2H), 8.02-7.94 (m, 5H), 7.65-7.60 (m, 1H), 7.58-7.45 (m, 4H), 7.35 (q, J=7.7, 4H), 6.65 (s, 1H), 6.40 (d, J=6.7, 1H), 5.31 (s, 2H), 5.08 (dd, J=4.2, 11.6, 1H), 4.79 (dd, J=6.4, 11.6, 1H), 4.74 (td, J=4.2, 6.5, 1H), 1.60 (s, 3H).

$^{13}$C NMR (126 MHz, CDCl$_3$) δ 166.31 (C=O), 165.38 (C=O), 165.32 (C=O), 159.13 (C2), 152.87 (C6), 152.06 (C4), 141.42 (C8), 133.77 (C—H), 133.69 (C—H), 133.28 (C—H), 129.90 (C—H), 129.82 (C—H), 129.78 (C), 129.70 (C—H), 129.41 (C), 128.78 (C), 128.61 (C—H), 128.50 (C—H), 128.41 (C—H), 126.00 (C5), 88.84 (C1'), 85.68 (C2'), 79.43 (C4'), 76.07 (C3'), 63.57 (C5'), 17.77 (2'-Me).

Example 2

(2R,3R,4R,5R)-2-(2-Amino-6-methoxy-9H-purin-9-yl)-5-(hydroxymethyl)-3-methyltetrahydrofuran-3,4-diol

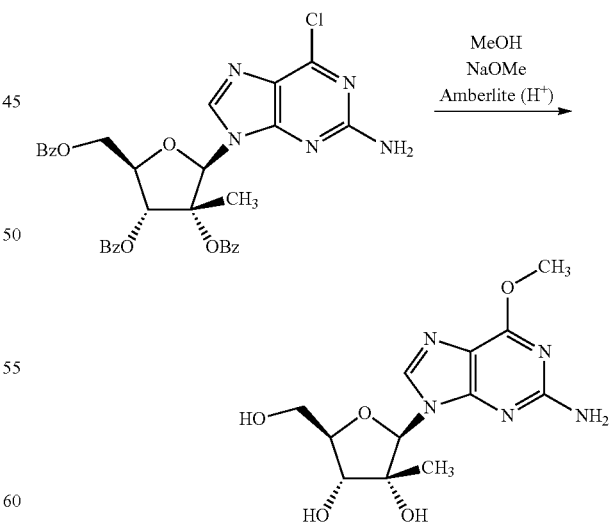

To a suspension of (2R,3R,4R,5R)-2-(2-amino-6-chloro-9H-purin-9-yl)-5-(benzoyloxymethyl)-3-methyltetrahydrofuran-3,4-diyl dibenzoate (3.0 g, 4.78 mmol) in methanol (36 mL) at 0° C. was added NaOMe in methanol (5.4 mL, 25% w/w). The mixture was stirred at room temperature for 24 h then quenched by addition of amberlite (H+). The mixture was then filtrated and methanol was removed under reduced pressure. The resultant residue was dissolved in water (50 mL) and extracted with hexane (50 mL). The organic layer was then extracted with water (50 mL), and the combined water fractions were concentrated under reduced pressure. The residue was purified by silica gel chromatography (CHCl$_3$/MeOH 85:15) to give the pure compound (1.125 g, 76%) as a white solid.

The following are the NMR, HPLC and CHN results analyzing the synthesized compound:

$^1$H NMR (500 MHz, MeOH-d$_4$) δ 8.26 (s, 1H), 5.99 (s, 1H), 4.24 (d, J=9.1, 1H), 4.08 (s, 3H), 4.04 (ddd, J=2.3, 5.7, 8.6, 2H), 3.87 (dd, J=3.0, 12.4, 1H), 0.96 (s, 3H).

$^{13}$C NMR (126 MHz, MeOH-d$_4$) δ 162.75 (C6), 161.86 (C2), 154.50 (C4), 139.35 (C8), 115.36 (C5), 93.00 (C1'), 84.15 (C4'), 80.34 (C2'), 73.57 (C3'), 61.17 (C5'), 54.25 (6-OMe), 20.35 (2'-Me).

HPLC: $t_R$=9.00 min; column: Varian Pursuit XRs 5, C18, 150×4.6 mm The method is: Linear gradient H$_2$O/ACN: 0% to 100% ACN in 30 min).

Elemental analysis: calculated for C$_{12}$H$_{17}$N$_5$O$_5$+0.75H$_2$O: C, 44.37; H, 5.74; N, 21.56. Found: C, 44.24; H, 5.49; N, 20.83.

Example 3

(2R,3R,4R,5R)-2-(2-Amino-8-iodo-6-methoxy-9H-purin-9-yl)-5-(hydroxymethyl)-3-methyltetrahydrofuran-3,4-diol was synthesized as follows

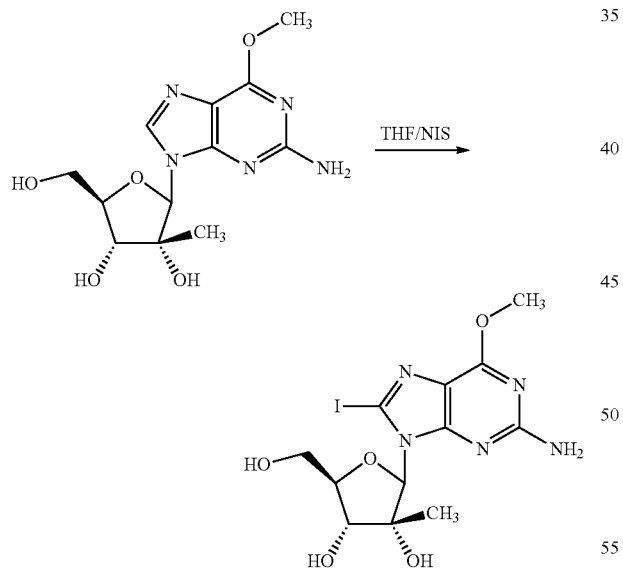

2-Amino-6-methoxy-9-(2-C-methyl-β-D-ribofuranosyl) purine (1.5 g, 4.82 mmol) was suspended in dry THF (40 mL) and 1 mol eq. of NIS (1.1 g, 4.82 mmol) was added. The mixture was warmed to 35° C. and stirred in the dark for 3 days. After that time, solution was concentrated and the resulting solid was purified by silica gel chromatography using 1-4% (gradient) of MeOH in chloroform to yield 980 mg (47% yield) of the desired product.

The following are the NMR, HPLC and MS results analyzing the synthesized compound:

$^1$H NMR (500 MHz, MeOH-d$_4$) δ 6.00 (s, 1H, H$_1'$), 4.64 (d, J=9.0 Hz, 1H, H$_3'$), 4.07-3.98 (m, 3H, H$_4'$, and H$_5'$), 4.05 (s, 3H, 6OC$\underline{H}_3$), 1.01 (s, 3H, 2'CC$\underline{H}_3$).

$^{13}$C NMR (126 MHz, MeOH-d$_4$) δ 161.70 (C6), 161.08 (C2), 154.28 (C4), 119.18 (C5), 99.27 (C8), 98.71 (C1'), 84.39 (C4'), 80.31 (C2'), 74.52 (C3'), 62.40 (C5'), 54.41 (6OCH$_3$), 21.25 (2'CCH$_3$).

HPLC: $t_R$=7.65 min; column: Varian Pursuit XRs 5, C18, 150×4.6 mm The method is: Linear gradient H$_2$O/ACN: 0% to 100% ACN in 30 min).

MS (TOF AP+) m/z: 438.03 (MH+, 100%);

HRMS C$_{12}$H$_{17}$N$_5$O$_5$I$_1$ Calculated: 438.0274. found: 438.0288.

Example 4

2-Amino-9-((2R,3R,4R,5R)-3,4-dihydroxy-5-(hydroxymethyl)-3-methyltetrahydrofuran-2-yl)-8-iodo-1H-purin-6(9H)-one was synthesized as follows

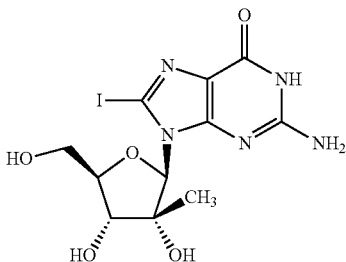 [SMILES: C[C@@]1(O)[C@H](O)[C@@H](CO)O[C@H]1n1c(I)nc2c(=O)[nH]c(N)nc21]

This compound can be synthesized from 2-amino-8-iodo-6-methoxy-9-(2-C-methyl-β-D-ribofuranosyl)purine using procedures familiar to one skilled in the art. For example: To a solution of 2-amino-8-iodo-6-methoxy-9-(2-C-methyl-β-D-ribofuranosyl)purine (XV)(1 mmol) in acetonitrile (3.0 mL) under nitrogen is added diethylisopropyl amine (52 mL, 0.3 mmol), followed by the addition of NaI (99 mg, 0.5 mmol) and TMSCl (64 mL, 0.5 mmol). The contents are stirred under nitrogen for 16 h. After completion of the reaction (monitoring by TLC), triethyl amine (30 mL, 0.3 mmol) are added. The reaction is concentrated under vacuum, and the solids are dissolved in methanol/water mixture (1.5 mL, 0.5 mL) and are stirred for 15 min.

Example 5

(2R,3R,4R,5R)-2-(2-Amino-8-bromo-6-methoxy-9H-purin-9-yl)-5-(hydroxymethyl)-3-methyltetrahydrofuran-3,4-diol was synthesized as follows

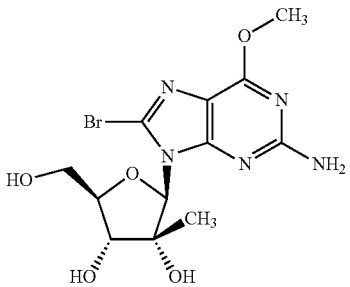 [SMILES: COc1nc(N)nc2c1nc(Br)n2[C@@H]1O[C@H](CO)[C@@H](O)[C@@]1(C)O]

2-Amino-6-methoxy-9-(2-C-methyl-β-D-ribofuranosyl) purine (1.5 g, 4.82 mmol) was suspended in MeOH (50 mL) and 1 mol eq. of NBS (1.03 g, 4.82 mmol) was added. The mixture was stirred at room temperature for 4 h. After that time, solution was concentrated and the resulting solid was purified by silica gel chromatography using 1-4% (gradient) of MeOH in chloroform to yield 1.65 g (88% yield) of the desired product.

The following are the NMR, HPLC and MS results analyzing the synthesized compound:

$^1$H NMR (500 MHz, MeOD) δ 6.04 (s, 1H, H$_{1'}$), 4.60 (d, J=8.0 Hz, 1H, H$_{3'}$), 4.09-4.05 (m, 2H, H$_{4'}$ and H$_{5'a}$), 4.04 (s, 3H, 6OC$\underline{H}_3$), 3.98 (dd, J=4.0 Hz, J=12.5 Hz, 1H, H$_{5'b}$), 1.01 (s, 3H, 2'CC$\underline{H}_3$).

$^{13}$C NMR (126 MHz, MeOD) δ 161.89 (C6), 161.18 (C2), 154.45 (C4), 125.57 (C8), 116.37 (C5), 96.70 (C1'), 84.40 (C4'), 80.38 (C2'), 74.34 (C3'), 62.27 (C5'), 54.66 (6OCH$_3$), 21.23 (2'CCH$_3$).

HPLC t$_R$=7.37 min

MS (TOF AP+) m/z: 390.04 (MH$^+$, 100%);

HRMS C$_{12}$H$_{17}$N$_5$O$_5$Br$_1$ Calculated: 390.0413. found: 390.0400.

Example 6

(2R,3R,4R,5R)-2-(2-Amino-8-chloro-6-methoxy-9H-purin-9-yl)-5-(hydroxymethyl)-3-methyltetrahydrofuran-3,4-diol was synthesized as follows

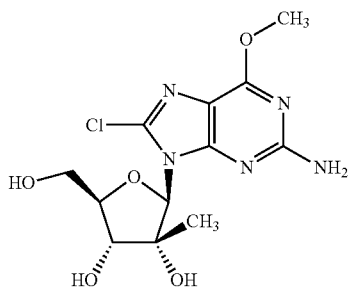

2-Amino-6-methoxy-9-(2-C-methyl-β-D-ribofuranosyl) purine (250 mg, 0.80 mmol) was suspended in dry THF (10 mL) and 1 mol eq. of NCS (110 mg, 0.80 mmol) was added. The mixture was warmed to 35° C. and stirred in the dark overnight. After that time, solution was concentrated and the resulting solid was purified by silica gel chromatography using 1-4% (gradient) of MeOH in chloroform to yield 235 mg (85% yield) of the desired product.

The following are the NMR, HPLC and MS results analyzing the synthesized compound:

$^1$H NMR (500 MHz, MeOD) δ 6.03 (s, 1H, H$_{1'}$), 4.58 (d, J=8.0 Hz, 1H, H$_{3'}$), 4.09-4.04 (m, 2H, H$_{4'}$ and H$_{5'a}$), 4.05 (s, 3H, 6OC$\underline{H}_3$), 3.97 (dd, J=4.0 Hz, J=11.0 Hz, 1H, H$_{5'b}$), 1.03 (s, 3H, 2'CC$\underline{H}_3$).

$^{13}$C NMR (126 MHz, MeOD) δ 162.02 (C6), 161.30 (C2), 154.35 (C4), 136.59 (C8), 114.52 (C5), 95.55 (C1'), 84.29 (C4'), 80.31 (C2'), 74.42 (C3'), 62.35 (C5'), 54.55 (6OCH$_3$), 21.03 (2'CCH$_3$).

HPLC t$_R$=7.63 min

MS (TOF AP+) m/z: 346.09 (MH$^+$, 100%);

HRMS C$_{12}$H$_{17}$N$_5$O$_5$Cl$_1$ Calculated: 346.0918. found: 346.0901.

The 5'-phosphoroamidates of 2-amino-8-iodo-6-methoxy-9-(2-C-methyl-β-D-ribofuranosyl)purine were synthesized by procedures available to one skilled in the art, including the Methods A and B below:

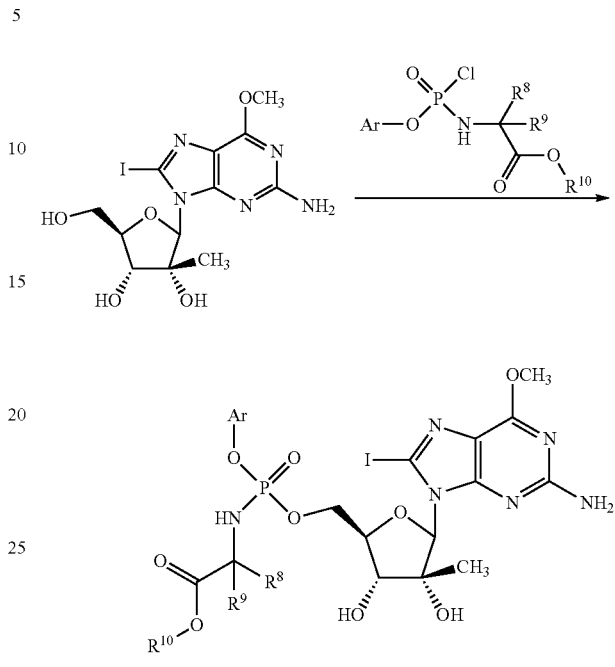

Method A:

To a solution of the nucleoside (e.g. 2-amino-8-iodo-6-methoxy-9-(2-C-methyl-β-D-ribofuranosyl)purine, Example 3) (1 equiv) dissolved in THF (20 mL/g) was added N-methyl-imidazole (NMI, Aldrich, 5 equiv) followed by the chloro(naphthalen-1-yloxy)phosphorylamino acid derivative (3 equiv) dissolved in THF (20 mL). The mixture was stirred overnight and the solvent was removed under reduced pressure. The residue was then purified on silica gel (CHCl$_3$/MeOH 95:5) to give the pure phosphoroamidate in 20 to 30% yield. In some cases, some trace of N-methyl-imidazole remains: to remove the N-methyl-imidazole, the phosphoroamidate was dissolved in chloroform and washed 3 times with hydrochloric acid (HCl 0.1N). The organic layer was then dried over sodium sulfate and evaporated under reduced pressure to afford the pure compound. In some cases, the latter needed to be purified a second time (100% CHCl$_3$ to 95:5 CHCl$_3$/MeOH).

Method B.

To a solution of the nucleoside (e.g. 2-amino-8-iodo-6-methoxy-9-(2-C-methyl-β-D-ribofuranosyl)purine) (Aldrich, 1 equiv) dissolved in anhydrous THF (4 mL/mmol) was added 1M solution of tert-buty MgCl in THF (Aldrich, 2 equiv) at 0° C. After stirring 15 min, a solution of the chloro (naphthalen-1-yloxy)phosphorylamino acid derivative (2 equiv) in THF (30 mL) was added dropwise into the reaction mixture, which was then allowed to warm to room temperature and stirred overnight. The reaction was monitored by TLC. The reaction mixture was washed with a saturated NH$_4$Cl solution (300 mL) and brine (100 mL). The organic layer was dried over anhydrous sodium sulfate and concentrated. The crude material was purified by column chromatography on silica gel using CH$_2$Cl$_2$/MeOH (96:4) to obtain phosphoroamidate in 10-50% yields.

Example 7

Benzyl 2(S)-((((2R,3R,4R,5R)-5-(2-Amino-8-iodo-6-methoxy-9H-purin-9-yl)-3,4-dihydroxy-4-methyltetrahydrofuran-2-yl)methoxy(naphthalene-1-yloxy)phosphorylamino)propanoate was synthesized as follows

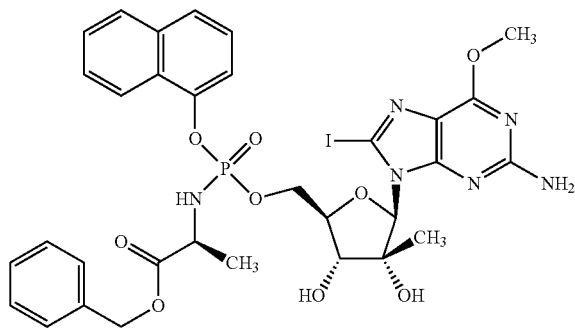 [SMILES: COc1nc(N)nc2c1nc(I)n2[C@@H]1O[C@H](COP(=O)(N[C@@H](C)C(=O)OCc2ccccc2)Oc2cccc3ccccc23)[C@@H](O)[C@@]1(C)O]

The general Method B for the synthesis of 5'-phosphoroamidates was used. To a solution of 300 mg (0.67 mmol) of (2R,3R,4R,5R)-2-(2-amino-8-iodo-6-methoxy-9H-purin-9-yl)-5-(hydroxymethyl)-3-methyltetrahydrofuran-3,4-diol in 5 mL of THF, t-BuMgCl 1.37 mL (1.37 mmol), was added followed by naphthalen-1-yl(benzoxy-L-alaninyl)phosphorochloridate 550 mg (1.37 mmol) in 5 mL of THF. After silica gel column chromatography, 70 mg of pure product was obtained in a 13% yield, as an off white solid.

The following are the NMR results analyzing the synthesized compound:

$^1$H NMR (500 MHz, MeOH-d$_4$) δ 8.15, 7.98 (2d, 1H, J=8.0 Hz, H$_8$-naph), 7.87, 7.78 (2d, 1H, J=8.0 Hz, H$_5$-napht), 7.67, 7.56 (2d, J=8.0 Hz, 1H, H$_4$-napht), 7.53-7.41 (m, 3H, H$_2$, H$_7$, H$_6$-napht), 7.39-7.26 (m, 1H, H$_3$-napht), 7.28-7.23 (m, 5H, Ph), 5.97, 5.96 (2s, 1H, H$_{1'}$), 5.00-4.91 (m, 2H, CH$_2$ ester), 4.90-4.78 (m, 2H, H$_{3'}$ and H$_{5'a}$), 4.60-4.54 (m, 1H, H$_{5'b}$), 4.29-4.22 (m, 1H, H$_{4'}$), 4.08-4.02 (m, 1H, Hα, Ala), 3.98, 3.97 (2s, 3H, 6OCH$_3$), 1.30 (d, J=7.0 Hz, 3H, CH$_3$ Ala), 1.24 (d, J=6.0 Hz, 3H, CH$_3$ Ala), 1.03, 1.02 (2s, 3H, 2'CCH$_3$).

$^{13}$C NMR (126 MHz, MeOH-d$_4$) δ 174.79, 174.60 (2d, $^3J_{C-C-N-P}$=5.0 Hz, C=O ester), 161.34, 161.27 (C6), 161.20, 161.07 (C2), 154.50, 154.44 (C4), 148.01, 147.95 (2d, $^2J_{C-O-P}$=7.5 Hz, ipso Naph), 137.15, 137.12 (ipso Ph), 136.21, 136.07 (C10-Naph), 1129.50, 129.36, 129.33, 129.28, 129.19, 129.09, 129.07, 128.75, 128.60, 128.27, 128.01, 127.91, 127.86, 127.80, 127.75, 127.65, 127.53, 127.37, 127.13, 126.43, 126.31, 125.80, 125.58, 122.82, 122.70 (C-Naph and Ph), 119.14, 119.09 (C5), 116.28 (d, $^2J_{C-C-O-P}$=3.8 Hz, C2-Naph), 115.90 (d, $^2J_{C-C-O-P}$=2.5 Hz, C2-Naph), 99.75, 99.72 (C8), 98.04 (C1'), 83.33, 83.16 (2d, $^3J_{C-C-O-P}$=7.5 Hz, C4'), 80.22, 80.19 (C2'), 76.09, 76.04 (C3'), 69.52, 69.40 (2d, $^2J_{C-O-P}$=5.0 Hz, C5'), 67.82, 67.76 (CH$_2$ ester), 54.18, 54.16 (6OCH$_3$), 51.64, 51.61 (Cα Ala), 20.66, 20.45 (2d, $^3J_{C-C-N-P}$=6.3 Hz, CH$_3$ Ala), 20.10, 20.05 (2'CCH$_3$).

$^{31}$P NMR (202 MHz, MeOH-d$_4$) δ 4.17, 3.69.

HPLC t$_R$=19.76, 20.35 min

MS (TOF ES+) m/z: 805.12 (MH$^+$, 100%);

HRMS C$_{32}$H$_{35}$N$_6$O$_9$P$_1$I$_1$ Calculated: 805.1248. found: 805.1241.

Example 8

(2S)-2,4-Difluorobenzyl 2-((((2R,3R,4R,5R)-5-(2-Amino-8-iodo-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

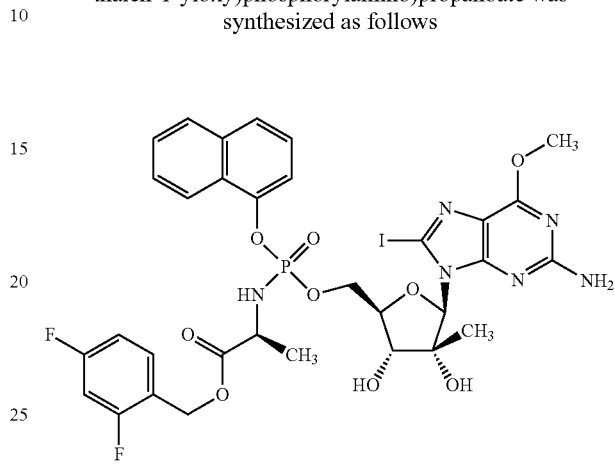

The general Method B for the synthesis of 5'-phosphoroamidates was used. To a solution of 300 mg (0.67 mmol) of (2R,3R,4R,5R)-2-(2-amino-8-iodo-6-methoxy-9H-purin-9-yl)-5-(hydroxymethyl)-3-methyltetrahydrofuran-3,4-diol in 5 mL of THF, tBuMgCl 1.37 mL (1.37 mmol), was added followed by naphthalen-1-yl (2,4difluorobenzoxy-L-alaninyl)phosphorochloridate 603 mg (1.37 mmol) in 5 mL of THF. After silica gel column chromatography, 120 mg of pure product was obtained in a 20% yield, as an off white solid.

The following are the NMR, HPLC and MS results analyzing the synthesized compound:

$^1$H NMR (500 MHz, MeOH-d$_4$) δ 8.14-8.12, 7.97-7.96 (2m, 1H, H$_8$-naph), 7.85-7.83, 7.75-7.74 (2m, 1H, H$_5$-napht), 7.64, 7.54 (2d, J=8.0 Hz, 1H, H$_4$-napht), 7.50-7.33 (m, 3H, H$_2$, H$_7$, H$_6$-napht), 7.32-7.24 (m, 2H, H$_3$-napht and CH-Ph), 6.89-6.78 (m, 2H, Ph), 5.96, 5.91 (2s, 1H, H$_{1'}$), 5.04-4.95 (m, 2H, CH$_2$ ester), 4.85-4.76 (m, 2H, H$_3$, and H$_{5'a}$), 4.64-4.55 (m, 1H, H$_{5'b}$), 4.28-4.22 (m, 1H, H$_{4'}$), 4.08-4.02 (m, 1H, Hα, Ala), 4.00, 3.99 (2s, 3H, 6OCH$_3$), 1.30, 1.24 (2d, J=7.0 Hz, 3H, CH$_3$ Ala), 1.01 (s, 3H, 2'CCH$_3$).

$^{13}$C NMR (126 MHz, MeOH-d$_4$) δ 174.62, 174.43 (2d, $^3J_{C-C-N-P}$=5.0 Hz, C=O ester), 159.50 (d, J$_{C-F}$=248.5 Hz, C—F Ph), 164.42 (d, J$_{C-F}$=243.7 Hz, C—F Ph), 162.46 (d, J$_{C-F}$=246.7 Hz, C—F Ph), 162.33 (d, J$_{C-F}$=251.2 Hz, C—F Ph), 161.46, 161.42 (C6), 161.29, 161.25 (C2), 154.50, 154.44 (C4), 148.00, 147.90 (2d, $^2J_{C-O-P}$=7.5 Hz, ipso Naph), 136.19, 136.01 (C10-Naph), 133.08, 133.05 (2d, $^3J_{C-F}$=7.1 Hz, CH-Ph), 128.78, 128.61 (C-Naph), 127.85 (d, $^3J_{C-C-O-P}$=6.3 Hz, C9-Naph), 127.72 (d, $^3J_{C-C-O-P}$=5.0 Hz, C9-Naph), 127.55, 127.38, 127.11, 126.43, 126.32, 125.85, 125.64, 122.78, 122.68 (C-Naph), 120.51-120.43 (m, ipso Ph), 118.80, 118.77 (C5), 116.28 (d, $^2J_{C-C-O-P}$=3.8 Hz, C2-Naph), 116.02 (d, $^2J_{C-C-O-P}$=2.5 Hz, C2-Naph), 112.35, 112.32 (2d, $^2J_{C-F}$=21.0 Hz, CH-Ph), 104.75, 104.55 (2d, $^2J_{C-F}$=25.2 Hz, CH-Ph), 99.75, 99.72 (C8), 98.05 (C1'), 83.37, 83.21 (2d, $^3J_{C-C-O-P}$=7.5 Hz, C4'), 80.18 (C2'), 76.04, 76.00 (C3'), 69.48, 69.34 (2d, $^2J_{C-O-P}$=5.0 Hz, C5'), 61.18, 61.16 (CH$_2$ ester), 54.52, 54.42 (6OCH$_3$), 51.61, 51.58

(Cα Ala), 20.79, 20.70 (2'CCH$_3$), 20.40 (d, $^3J_{C-C-N-P}$=5.0 Hz, CH$_3$ Ala), 20.36 (d, $^3J_{C-C-N-P}$=6.3 Hz, CH$_3$ Ala).

$^{31}$P NMR (202 MHz, MeOH-d$_4$) δ 4.16, 3.81.

$^{19}$F NMR (470 MHz, MeOH-d$_4$) δ −111.14, −113.69, −115.43, −117.41

HPLC t$_R$=19.29, 20.31 min

MS (TOF ES+) m/z: 863.08 (MNa$^+$, 100%);

HRMS C$_{32}$H$_{32}$N$_6$O$_9$F$_2$Na$_1$P$_1$I$_1$ Calculated: 863.0879. found: 863.0838.

Example 9

(2S)-Propyl 2-((((2R,3R,4R,5R)-5-(2-Amino-8-iodo-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

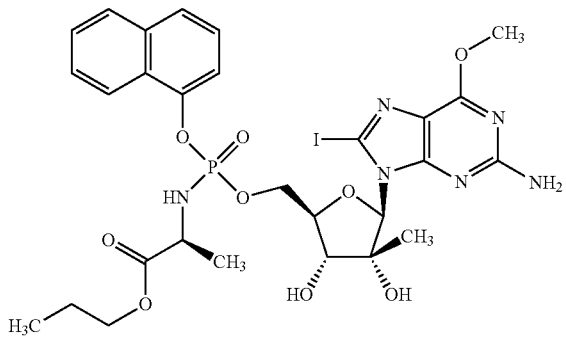 [SMILES: CCCOC(=O)[C@H](C)NP(=O)(OC[C@H]1O[C@@H](n2c(I)nc3c(OC)nc(N)nc32)[C@](C)(O)[C@@H]1O)Oc1cccc2ccccc12]

The general Method B for the synthesis of 5'-phosphoroamidates was used. To a solution of 300 mg (0.67 mmol) of (2R,3R,4R,5R)-2-(2-amino-8-iodo-6-methoxy-9H-purin-9-yl)-5-(hydroxymethyl)-3-methyltetrahydrofuran-3,4-diol in 5 mL of THF, t-BuMgCl 1.37 mL (1.37 mmol), was added followed by naphthalen-1-yl(propoxy-L-alaninyl)phosphorochloridate 488 mg (1.37 mmol) in 3 mL of THF. After silica gel column chromatography, 100 mg of pure compounds was obtained in a 17% yield, as an off white solid.

The following are the NMR, HPLC and MS results analyzing the synthesized compound:

$^1$H NMR (500 MHz, MeOH-d$_4$) δ 8.17-8.15, 8.00-7.98 (2m, 1H, H$_8$-naph), 7.84-7.83, 7.76-7.75 (2m, 1H, H$_5$-napht), 7.64, 7.55 (2d, J=8.0 Hz, 1H, H$_4$-napht), 7.51-7.36 (m, 3H, H$_2$, H$_7$, H$_6$-napht), 7.33-7.26 (m, 1H, H$_3$-napht), 5.99, 5.98 (2s, 1H, H$_{1'}$), 4.91-4.84 (m, 2H, H$_{3'}$ and H$_{5'a}$), 4.64-4.56 (m, 1H, H$_{5'b}$), 4.32-4.26 (m, 1H, H$_{4'}$), 4.04-3.97 (m, 1H, HαAla), 4.00, 3.96 (2s, 3H, 6OCH$_3$), 3.91-3.79 (m, 2H, OCH$_2$CH$_2$CH$_3$ ester), 1.52-1.45 (m, 2H, OCH$_2$CH$_2$CH$_3$ ester), 1.29, 1.23 (2d, J=7.0 Hz, 3H, CH$_3$ Ala), 1.03, 1.02 (2s, 3H, 2'CCH$_3$), 0.87, 0.84 (t, J=7.0 Hz, 3H, OCH$_2$CH$_2$CH$_3$ ester).

$^{13}$C NMR (126 MHz, MeOH-d$_4$) δ 175.12, 174.84 (2d, 3J$_{C-C-N-P}$=5.0 Hz, C=O ester), 161.37, 161.28 (C6), 161.18, 161.06 (C2), 154.53, 154.47 (C4), 148.04 (d, $^2J_{C-O-P}$=7.5 Hz, ipso Naph), 147.98 (d, $^2J_{C-O-P}$=8.8 Hz, ipso Naph), 136.20, 136.07 (C10-Naph), 128.79, 128.64 (C-Naph), 127.89 (d, $^3J_{C-C-O-P}$=6.3 Hz, C9-Naph), 127.76 (d, $^3J_{C-C-O-P}$=7.5 Hz, C9-Naph), 127.69, 127.56, 127.38, 127.14, 126.46, 126.35, 125.82, 125.59, 122.83, 122.69 (C-Naph), 119.19, 119.14 (C5), 116.24, 115.87 (2d, $^3J_{C-C-C-O-P}$=2.5 Hz, C2-Naph), 99.76, 99.65 (C8), 98.04 (C1'), 83.35 (d, $^3J_{C-C-O-P}$=7.5 Hz, C4'), 83.20 (d, $^3J_{C-C-O-P}$=8.8 Hz, C4'), 80.26, 80.25 (C2'), 76.15, 76.08

(C3'), 69.54, 69.41 (2d, $^2J_{C-O-P}$=5.0 Hz, C5'), 67.86, 67.85 (OCH$_2$CH$_2$CH$_3$ ester), 54.29, 54.26 (6OCH$_3$), 51.61, 51.58 (Cα Ala), 22.90, 22.88 (OCH$_2$CH$_2$CH$_3$ ester), 20.78, 20.73 (2'CCH$_3$), 20.66, 20.61 (CH$_3$ Ala), 10.65 (OCH$_2$CH$_2$CH$_3$ ester).

$^{31}$P NMR (202 MHz, MeOH-d$_4$) δ 4.22, 3.37

HPLC t$_R$=17.48, 18.29 min

MS (TOF ES+) m/z: 757.12 (MH$^+$, 100%);

HRMS C$_{28}$H$_{35}$N$_6$O$_9$P$_1$I$_1$ Calculated: 757.1248. found: 757.1229.

Example 10

(2S)-Butyl 2-((((2R,3R,4R,5R)-5-(2-Amino-8-iodo-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

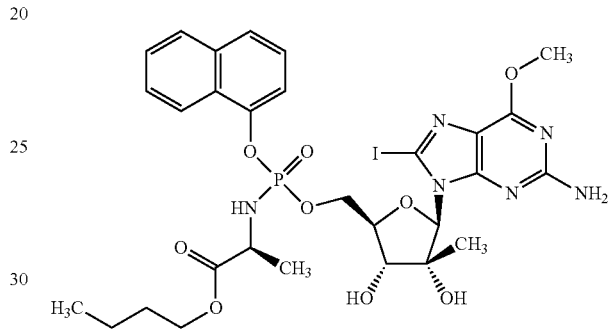

The general Method B for the synthesis of 5'-phosphoroamidates was used. To a solution of 300 mg (0.67 mmol) of (2R,3R,4R,5R)-2-(2-amino-8-iodo-6-methoxy-9H-purin-9-yl)-5-(hydroxymethyl)-3-methyltetrahydrofuran-3,4-diol in 5 mL of THF, t-BuMgCl 1.37 mL (1.37 mmol), was added followed by naphthalen-1-yl(butoxy-L-alaninyl)phosphorochloridate 510 mg (1.37 mmol) in 5 mL of THF. After silica gel column chromatography, 150 mg of pure product was obtained in a 28% yield, as an off white solid.

The following are the NMR, HPLC and MS results analyzing the synthesized compound:

$^1$H NMR (500 MHz, MeOH-d$_4$) δ 8.17-8.15, 7.99-7.97 (2m, 1H, H$_8$-naph), 7.85-7.83, 7.76-7.75 (2m, 1H, H$_5$-napht), 7.64, 7.55 (2d, J=8.0 Hz, 1H, H$_4$-napht), 7.51-7.35 (m, 3H, H$_2$, H$_7$, H$_6$-napht), 7.34-7.26 (m, 1H, H$_3$-napht), 5.99, 5.98 (2s, 1H, H$_{1'}$), 4.91-4.81 (m, 2H, H$_{3'}$ and H$_{5'a}$), 4.65-4.56 (m, 1H, H$_{5'b}$), 4.34-4.26 (m, 1H, H$_{4'}$), 4.03-3.99 (m, 1H, HαAla), 4.00, 3.96 (2s, 3H, 6OCH$_3$), 3.92-3.83 (m, 2H, OCH$_2$CH$_2$CH$_2$CH$_3$ ester), 1.46-1.39 (m, 2H, OCH$_2$CH$_2$CH$_2$CH$_3$ ester), 1.30-1.23 (m, 5H, OCH$_2$CH$_2$CH$_2$CH$_3$ ester and CH$_3$ Ala), 1.03 (s, 3H, 2'CCH$_3$), 0.84, 0.83 (2t, J=7.5 Hz, 3H, OCH$_2$CH$_2$CH$_3$ ester).

$^{13}$C NMR (126 MHz, MeOH-d$_4$) δ 175.12 (d, $^3J_{C-C-N-P}$=5.0 Hz, C=O ester), 174.85 (d, $^3J_{C-C-N-P}$=6.3 Hz, C=O ester), 161.33, 161.25 (C6), 161.19, 161.06 (C2), 154.50, 154.44 (C4), 148.03 (d, $^2J_{C-O-P}$=7.5 Hz, ipso Naph), 147.97 (d, $^2J_{C-O-P}$=8.8 Hz, ipso Naph), 136.19, 136.05 (C10-Naph), 128.81, 128.65 (C-Naph), 127.87 (d, $^3J_{C-C-O-P}$=6.3 Hz, C9-Naph), 127.73 (d, $^3J_{C-C-O-P}$=7.5 Hz, C9-Naph), 127.57, 127.40, 127.16, 126.49, 126.37, 125.83, 125.59, 122.83, 122.69 (C-Naph), 119.13, 119.09 (C5), 116.25, 115.83 (2d, $^3J_{C-C-C-O-P}$=2.5 Hz, C2-Naph), 99.87, 99.76 (C8), 98.03 (C1'), 83.35, 83.20 (2d, $^3J_{C-C-O-P}$=7.5 Hz, C4'), 80.25 (C2'), 76.14, 76.07

(C3'), 69.54, 69.40 (2d, $^2J_{C—O—P}$=5.0 Hz, C5'), 66.12, 65.99 (O$\underline{C}$H$_2$CH$_2$CH$_2$CH$_3$ ester), 54.31, 54.28 (6OCH$_3$), 51.60, 51.58 (Cα Ala), 31.65, 31.60 (OCH$_2$$\underline{C}$H$_2$CH$_2$CH$_3$ ester), 22.90, 22.88 (OCH$_2$CH$_2$$\underline{C}$H$_2$CH$_3$ ester), 20.80 (2'C$\underline{C}$H$_3$), 20.74, 20.63 (2d, $^3J_{C—C—O—P}$=7.5 Hz, CH$_3$ Ala), 14.14, 14.12 (OCH$_2$CH$_2$CH$_2$$\underline{C}$H$_3$ ester).

$^{31}$P NMR (202 MHz, MeOH-d$_4$) δ 4.26, 3.68

HPLC t$_R$=18.92, 19.65 min

MS (TOF ES+) m/z: 771.14 (MH$^+$, 100%);

HRMS C$_{29}$H$_{37}$N$_6$O$_9$P$_1$I$_1$ Calculated: 771.1404. found: 771.1400.

Example 11

(2S)-Pentyl 2-((((2R,3R,4R,5R)-5-(2-Amino-8-iodo-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

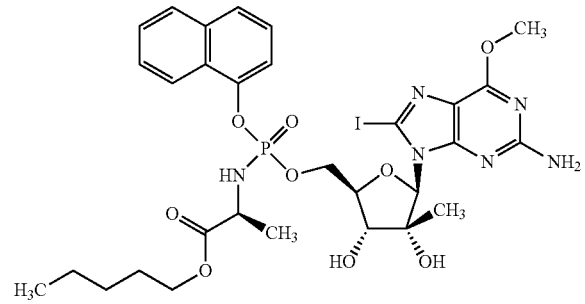 [SMILES: CCCCCOC(=O)[C@H](C)NP(=O)(OC[C@H]1O[C@@H](n2c(I)nc3c(OC)nc(N)nc32)[C@](C)(O)[C@@H]1O)Oc1cccc2ccccc12]

The general Method B for the synthesis of 5'-phosphoroamidates was used. To a solution of 300 mg (0.67 mmol) of (2R,3R,4R,5R)-2-(2-amino-8-iodo-6-methoxy-9H-purin-9-yl)-5-(hydroxymethyl)-3-methyltetrahydrofuran-3,4-diol in 5 mL of THF, t-BuMgCl 1.37 mL (1.37 mmol), was added followed by naphthalen-1-yl(butoxy-L-alaninyl)phosphorochloridate 500 mg (1.37 mmol) in 5 mL of THF. After silica gel column chromatography, 120 mg of pure product was obtained in a 22% yield, as an off white solid.

The following are the NMR, HPLC and MS results analyzing the synthesized compound:

$^1$H NMR (500 MHz, MeOH-d$_4$) δ 8.17-8.15, 8.00-7.98 (2m, 1H, H$_8$-naph), 7.85-7.83, 7.76-7.75 (2m, 1H, H$_5$-napht), 7.65, 7.55 (2d, J=8.5 Hz, 1H, H$_4$-napht), 7.51-7.35 (m, 3H, H$_2$, H$_7$, H$_6$-napht), 7.34-7.26 (m, 1H, H$_3$-napht), 5.99, 5.98 (2s, 1H, H$_1$'), 4.87-4.81 (m, 2H, H$_3$' and H$_{5'a}$), 4.65-4.56 (m, 1H, H$_{5'b}$), 4.34-4.26 (m, 1H, H$_4$'), 4.04-3.97 (m, 1H, HαAla), 4.00, 3.96 (2s, 3H, 6OCH$_3$), 3.92-3.81 (m, 2H, OC$\underline{H}_2$CH$_2$CH$_2$CH$_3$ ester), 1.47-1.41 (m, 2H, OCH$_2$C$\underline{H}_2$CH$_2$CH$_3$ ester), 1.29, 1.23 (2d, J=7.0 Hz, 3H, CH$_3$ Ala), 1.21-1.16 (m, 4H, OCH$_2$CH$_2$$\underline{C}$H$_2$CH$_2$CH$_3$ and OCH$_2$CH$_2$CH$_2$$\underline{C}$H$_2$CH$_3$ ester), 1.03 (s, 3H, 2'CCH$_3$), 0.83, 0.82 (2t, J=7.5 Hz, 3H, OCH$_2$CH$_2$C$\underline{H}_3$ ester).

$^{13}$C NMR (126 MHz, MeOH-d$_4$) δ 175.12, 174.86 (2d, $^3J_{C—C—N—P}$=5.0 Hz, C=O ester), 161.33, 161.25 (C6), 161.20, 161.07 (C2), 154.51, 154.44 (C4), 148.03 (d, $^2J_{C—O—P}$=7.5 Hz, ipso Naph), 147.97 (d, $^2J_{C—O—P}$=8.8 Hz, ipso Naph), 136.19, 136.05 (C10-Naph), 128.81, 128.65 (C-Naph), 127.87 (d, $^3J_{C—C—O—P}$=6.3 Hz, C9-Naph), 127.74 (d, $^3J_{C—C—O—P}$=8.8 Hz, C9-Naph), 127.57, 127.40, 127.15, 126.49, 126.37, 125.83, 125.59, 122.84, 122.70 (C-Naph), 119.12, 119.08 (C5), 116.25, 115.83 (2d, $^3J_{C—C—O—P}$=2.5 Hz, C2-Naph), 99.86, 99.77 (C8), 98.03 (C1'), 83.35, 83.20 (2d, $^3J_{C—C—O—P}$=7.5 Hz, C4'), 80.25 (C2'), 76.14, 76.08 (C3'), 69.55 (d, $^2J_{C—O—P}$=6.3 Hz, C5'), 69.40 (d, $^2J_{C—O—P}$=5.0 Hz, C5'), 66.39, 66.31 (O$\underline{C}$H$_2$CH$_2$CH$_2$CH$_2$CH$_3$ ester), 54.30, 54.27 (6OCH$_3$), 51.60, 51.58 (CαAla), 29.28, 29.23 (OCH$_2$$\underline{C}$H$_2$CH$_2$CH$_2$CH$_3$ ester), 29.06, 29.05 (OCH$_2$CH$_2$$\underline{C}$H$_2$CH$_2$CH$_3$ ester), 23.36, 23.34 (OCH$_2$CH$_2$CH$_2$$\underline{C}$H$_2$CH$_3$ ester), 20.79, 20.74 (2'C$\underline{C}$H$_3$), 20.70, 20.62 (2d, $^3J_{C—C—N—P}$=6.3 Hz, CH$_3$ Ala), 14.40 (OCH$_2$CH$_2$CH$_2$CH$_2$$\underline{C}$H$_3$ ester).

$^{31}$P NMR (202 MHz, MeOH-d$_4$) δ 4.27, 3.68

HPLC t$_R$=20.51, 21.31 min

MS (TOF ES+) m/z: 785.16 (MH$^+$, 100%);

HRMS C$_{30}$H$_{39}$N$_6$O$_9$P$_1$I$_1$ Calculated: 785.1561. found: 785.1575.

Example 12

(2S)-Neopentyl 2-((((2R,3R,4R,5R)-5-(2-Amino-8-iodo-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

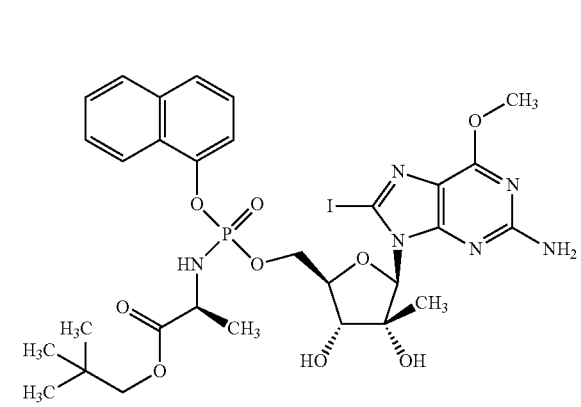 [SMILES: COc1nc(N)nc2c1nc(I)n2[C@@H]1O[C@H](COP(=O)(N[C@@H](C)C(=O)OCC(C)(C)C)Oc2cccc3ccccc23)[C@@H](O)[C@@]1(C)O]

The general Method B for the synthesis of 5'-phosphoroamidates was used. To a solution of 100 mg (0.23 mmol) of (2R,3R,4R,5R)-2-(2-amino-8-iodo-6-methoxy-9H-purin-9-yl)-5-(hydroxymethyl)-3-methyltetrahydrofuran-3,4-diol in 3 mL of THF, t-BuMgCl 0.46 mL (0.46 mmol), was added followed by naphthalen-1-yl (2,2-dimethylpropoxy-L-alaninyl)phosphorochloridate 152 mg (0.46 mmol) in 2 mL of THF. After silica gel column chromatography, 46 mg of pure product was obtained in a 27% yield, as an off white solid.

The following are the NMR results analyzing the synthesized compound:

$^1$H NMR (500 MHz, MeOH-d$_4$) δ 8.18-8.16, 7.99-7.97 (2m, 1H, H$_8$-naph), 7.87-7.85, 7.77-7.76 (2m, 1H, H$_5$-napht), 7.67, 7.56 (2d, J=8.0 Hz, 1H, H$_4$-napht), 7.53-7.37 (m, 3H, H$_2$, H$_7$, H$_6$-napht), 7.34-7.26 (m, 1H, H$_3$-napht), 5.97, 5.96 (2s, 1H, H$_1$'), 4.89-4.82 (m, 2H, H$_3$' and H$_{5'a}$), 4.62-4.53 (m, 1H, H$_{5'b}$), 4.32-4.23 (m, 1H, H$_4$'), 4.08-3.99 (m, 1H, HαAla), 4.01, 3.97 (2s, 3H, 6OCH$_3$), 3.75, 3.72, 3.64, 3.58 (2AB, J$_{AB}$=10.5 Hz, 2H, CH$_2$ ester), 1.32, 1.25 (2d, J=7.0 Hz, 3H, CH$_3$ Ala), 1.03, 1.02 (2s, 3H, 2'CCH$_3$), 0.87, 0.84 (2s, 9H, 3×CH$_3$ ester).

$^{13}$C NMR (126 MHz, MeOH-d$_4$) δ 175.04 (d, $^3J_{C—C—N—P}$=5.0 Hz, C=O ester), 174.77 (d, $^3J_{C—C—N—P}$=6.3 Hz, C=O ester), 161.35, 161.27 (C6), 161.20, 161.06 (C2), 154.53, 154.45 (C4), 148.04, 147.97 (2d, $^2J_{C—O—P}$=7.5 Hz, ipso Naph), 136.23, 136.09 (C10-Naph), 128.78, 128.62 (C-Naph), 127.89, 127.77 (2d, $^3J_{C-C-O-P}$=6.3 Hz, C9-Naph), 127.68, 127.53, 127.38, 127.14, 126.46, 126.33, 125.82, 125.59, 122.83, 122.68 (C-Naph), 119.16, 119.12 (C5), 115.89, 115.86 (C2-Naph), 99.72 (C8), 98.04 (C1'), 83.36, 83.21 (2d, $^3J_{C-C-O-P}$=7.5 Hz, C4'), 80.24, 80.21 (C2'), 76.12, 76.02 (C3'), 75.34, 75.28 (CH$_2$ ester), 69.60, 69.44 (2d, $^2J_{C-O-P}$=5.0 Hz, C5'), 54.22, 54.20 (6OCH$_3$), 51.66, 51.60 (CαAla), 32.25 (C ester), 26.73 (3×CH$_3$ ester), 20.81 (d, $^3J_{C-C-N-P}$=6.3 Hz, CH$_3$ Ala), 20.70 (d, $^3J_{C-C-N-P}$=5.0 Hz, CH$_3$ Ala), 20.66 66 (2'CCH$_3$).

$^{31}$P NMR (202 MHz, MeOH-d$_4$) δ 4.18, 3.68.

HPLC t$_R$=20.23, 21.23 min

MS (TOF ES+) m/z: 785.15 (MH$^+$, 100%);

HRMS C$_{30}$H$_{39}$N$_6$O$_9$P$_1$I$_1$ Calculated: 785.1546. found: 785.1561.

Example 13

(2S)-Neopentyl 2-((((2R,3R,4R,5R)-5-(2-Amino-8-bromo-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

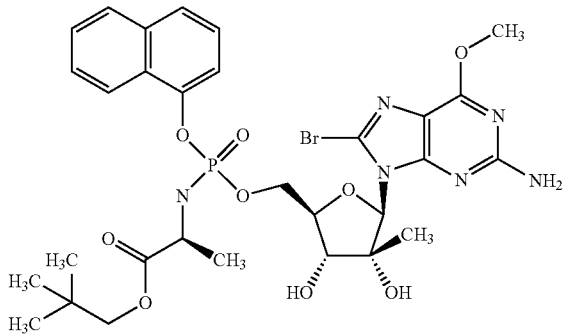 [SMILES: COc1nc(N)nc2c1nc(Br)n2[C@@H]1O[C@H](COP(=O)(N[C@@H](C)C(=O)OCC(C)(C)C)Oc2cccc3ccccc23)[C@@H](O)[C@@]1(C)O]

The general Method B for the synthesis of 5'-phosphoroamidates was used. To a solution of 160 mg (0.41 mmol) of (2R,3R,4R,5R)-2-(2-amino-8-bromo-6-methoxy-9H-purin-9-yl)-5-(hydroxymethyl)-3-methyltetrahydrofuran-3,4-diol in 3 mL of THF, t-BuMgCl 0.81 mL (0.81 mmol), was added followed by naphthalen-1-yl (2,2-dimethylpropoxy-L-alaninyl)phosphorochloridate 270 mg (0.81 mmol) in 2 mL of THF. After silica gel column chromatography, 70 mg of pure product was obtained in a 23% yield, as an off white solid.

The following are the NMR, and HPLC results analyzing the synthesized compound:

$^1$H NMR (500 MHz, MeOD) δ 8.17-8.15, 8.01-8.00 (2m, 1H, H$_8$-naph), 7.83-7.81, 7.75-7.73 (2m, 1H, H$_5$-napht), 7.63, 7.64 (2d, J=8.0 Hz, 1H, H$_4$-naph), 7.50-7.41 (m, 3H, H$_2$, H$_7$, H$_6$-naph), 7.36, 7.27 (2t, J=8.0 Hz, 1H, H$_3$-napht), 6.05, 6.04 (2s, 1H, H$_{1'}$), 4.86-4.82 (m, 2H, H$_{3'}$ and H$_{5'a}$), 4.67-4.57 (m, 1H, H$_{5'b}$), 4.35-4.27 (m, 1H, H$_{4'}$), 4.08-4.01 (m, 1H, Hα), 4.00, 3.96 (2s, 3H, 6OCH$_3$), 3.75, 3.72, 3.64, 3.58 (2 AB, J$_{AB}$=10.5 Hz, 2H, CH$_2$ ester), 1.33, 1.27 (2d, J=7.0 Hz, 3H, CH$_3$ Ala), 1.05, 1.04 (2s, 3H, 2'CCH$_3$), 0.84, 0.82 (2s, 9H, 3×CH$_3$ ester).

$^{13}$C NMR (126 MHz, MeOD) δ 175.05, 174.77 (2d, $^3J_{C-C-N-P}$=6.3 Hz, C=O ester), 161.58, 161.49 (C6), 161.40, 161.27 (C2), 154.83, 154.75 (C4), 148.03, 147.96 (2d, $^2J_{C-O-P}$=7.5 Hz, ipso Naph), 136.23, 136.09 (C10-Naph), 128.79, 128.63 (C-Naph), 127.82, 127.71 (2d, $^3J_{C-C-O-P}$=7.5 Hz, C9-Naph), 127.53, 127.38, 127.12, 126.44, 126.43, 125.82 (C-Naph), 125.71 (C8), 125.59, 122.81, 122.69 (C-Naph), 116.26, 116.23 (2d, $^3J_{C-C-O-P}$=2.5 Hz, C2-Naph), 115.90, 115.87 (C5), 95.88 (C1'), 83.42 (d, $^3J_{C-C-O-P}$=6.3 Hz, C4'), 83.24 (d, $^3J_{C-C-O-P}$=7.5 Hz, C4'), 80.19, 80.17 (C2'), 76.03, 75.93 (C3'), 75.34, 75.29 (CH$_2$ ester), 69.51, 69.39 (2d, $^2J_{C-O-P}$=5.0 Hz, C5'), 54.29, 54.27 (6OCH$_3$), 51.66, 51.60 (CαAla), 32.24 (C ester), 26.72, 26.71 (3×CH$_3$ ester), 20.82 (d, $^3J_{C-C-N-P}$=6.3 Hz, CH$_3$ Ala), 20.69 (d, $^3J_{C-C-N-P}$=7.5 Hz, CH$_3$ Ala), 20.56, 20.51 (2'CCH$_3$).

$^{31}$P NMR (202 MHz, CDCl$_3$) δ 4.15, 3.71.

HPLC t$_R$=20.97, 21.77 min

Example 14

(2S)-Neopentyl 2-((((2R,3R,4R,5R)-5-(2-Amino-8-chloro-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

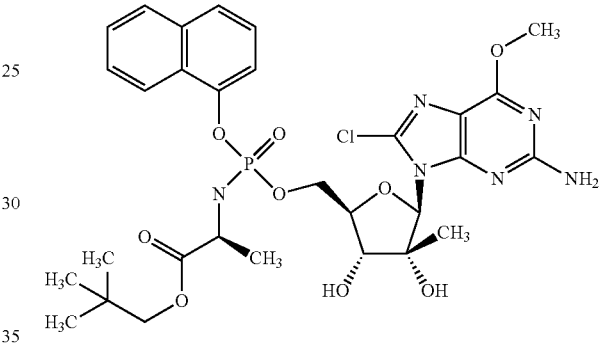

The general Method B for the synthesis of 5'-phosphoroamidates was used. To a solution of 160 mg (0.41 mmol) of (2R,3R,4R,5R)-2-(2-amino-8-chloro-6-methoxy-9H-purin-9-yl)-5-(hydroxymethyl)-3-methyltetrahydrofuran-3,4-diol in 3 mL of THF, t-BuMgCl 0.81 mL (0.81 mmol), was added, followed by naphthalen-1-yl (2,2-dimethylpropoxy-L-alaninyl)phosphorochloridate 270 mg (0.81 mmol) in 2 mL of THF. After silica gel column chromatography, 70 mg of pure product was obtained in a 23% yield, as an off white solid.

The following are the NMR, HPLC and MS results analyzing the synthesized compound:

$^1$H NMR (500 MHz, MeOD) δ 8.17-8.16, 8.02-8.00 (2m, 1H, H$_8$-naph), 7.86-7.85, 7.78-7.76 (2m, 1H, H$_5$-napht), 7.67, 7.56 (2d, J=8.0 Hz, 1H, H$_4$-napht), 7.53-7.36 (m, 3H, H$_2$, H$_7$, H$_6$-napht), 7.35-7.27 (m, 1H, H$_3$-napht), 6.02, 6.01 (2s, 1H, H$_{1'}$), 4.88-4.80 (m, 2H, H$_{3'}$ and H$_{5'a}$), 4.63-4.53 (m, 1H, H$_{5'b}$), 4.32-4.24 (m, 1H, H$_{4'}$), 4.08-4.02 (m, 1H, Hα), 4.01, 3.98 (2s, 3H, 6OCH$_3$), 3.76, 3.73, 3.65, 3.59 (2 AB, J$_{AB}$=10.5 Hz, 2H, CH$_2$ ester), 1.33, 1.27 (2d, J=7.0 Hz, 3H, CH$_3$ Ala), 1.06, 1.05 (2s, 3H, 2'CCH$_3$), 0.86, 0.84 (2s, 9H, 3×CH$_3$ ester).

$^{13}$C NMR (126 MHz, MeOD) δ 175.04 (2d, $^3J_{C-C-N-P}$=5.0 Hz, C=O ester), 174.76 (2d, $^3J_{C-C-N-P}$=6.3 Hz, C=O ester), 161.70, 161.61 (C6), 161.50, 161.38 (C2), 154.68, 154.61 (C4), 148.06, 147.96 (2d, $^2J_{C-O-P}$=7.5 Hz, ipso Naph), 136.65, 136.58 (C8), 136.23, 136.09 (C10-Naph), 128.79, 128.64 (C-Naph), 127.89, 127.78 (2d, $^3J_{C-C-O-P}$=6.3 Hz, C9-Naph), 127.68, 127.53, 127.37, 127.12, 126.45, 126.34, 125.83, 125.60, 122.81, 122.70 (C-Naph), 116.25 (d, $^3J_{C-C-O-P}$=3.8 Hz, C2-Naph), 115.89 (d, $^3J_{C-C-O-P}$=2.5 Hz, C2-Naph), 114.38 (C5), 94.67 (C1'), 83.39 (d, $^3J_{C-C-O-P}$=7.5 Hz, C4'), 83.20 (d, $^3J_{C-C-O-P}$=8.8 Hz, C4'), 80.13 (C2'), 75.99, 75.90 (C3'), 75.34, 75.30 (CH$_2$ ester), 69.45, 69.33 (2d, $^2J_{C-O-P}$=5.0 Hz, C5'), 54.30, 54.28 (6OCH$_3$), 51.66, 51.60 (CαAla), 32.24, 32.23 (C ester), 26.72, 26.69 (3×CH$_3$ ester), 20.83, 20.70 (2d, $^3J_{C-C-N-P}$=6.3 Hz, CH$_3$ Ala), 20.48, 20.43 (2'CCH$_3$).

$^{31}$P NMR (202 MHz, CDCl$_3$) δ 4.16, 3.74.

HPLC Rt=20.89, 21.72 min

MS (TOF ES+) m/z: 713.19 (MH$^+$, 100%);

HRMS C$_{32}$H$_{35}$N$_6$O$_9$P$_1$Cl$_1$ Calculated: 713.1892. found: 713.1911.

Example 15

(2S)-Cyclobutyl 2-((((2R,3R,4R,5R)-5-(2-Amino-8-iodo-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

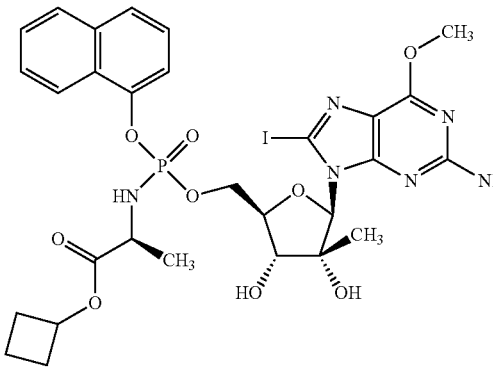

The general Method B for the synthesis of 5'-phosphoroamidates was used. To a solution of 300 mg (0.67 mmol) of (2R,3R,4R,5R)-2-(2-amino-8-iodo-6-methoxy-9H-purin-9-yl)-5-(hydroxymethyl)-3-methyltetrahydrofuran-3,4-diol in 5 mL of THF, t-BuMgCl 1.37 mL (1.37 mmol), was added followed by naphthalen-1-yl(cyclobutoxy-L-alaninyl)phosphorochloridate 510 mg (1.37 mmol) in 5 mL of THF. After silica gel column chromatography, 79 mg of pure product was obtained in a 15% yield, as an off white solid.

The following are the NMR, HPLC and MS results analyzing the synthesized compound:

$^1$H NMR (500 MHz, MeOH-d$_4$) δ 8.18-8.16, 7.99-7.98 (2m, 1H, H$_8$-naph), 7.87-7.85, 7.78-7.77 (2m, 1H, H$_5$-napht), 7.67, 7.57 (2d, J=8.0 Hz, 1H, H$_4$-napht), 7.53-7.36 (m, 3H, H$_2$, H$_7$, H$_6$-napht), 7.35-7.27 (m, 1H, H$_3$-napht), 5.98, 5.97 (2s, 1H, H$_{1'}$), 4.90-4.80 (m, 2H, H$_{3'}$ and H$_{5'a}$), 4.77-4.70 (m, 1H, CH ester), 4.63-4.54 (m, 1H, H$_{5'b}$), 4.32-4.24 (m, 1H, H$_{4'}$), 4.01, 3.97 (2s, 3H, 6OCH$_3$), 3.96-3.92 (m, 1H, HαAla), 2.21-2.16 (m, 2H, 2×OCHCH$_{2a''}$ ester), 1.92-1.83 (m, 2H, 2×OCHCH$_{2a''}$ ester), 1.73-1.66 (m, 1H, OCHCH$_2$CH$_{2b'}$ ester), 1.61-1.51 (m, 1H, OCHCH$_2$CH$_{2b'}$ ester), 1.29, 1.23 (2d, J=7.0 Hz, 3H, CH$_3$ Ala), 1.03, 1.02 (2s, 3H, 2'CCH$_3$).

$^{13}$C NMR (126 MHz, MeOH-d$_4$) δ 174.37 (d, $^3J_{C-C-N-P}$=5.0 Hz, C=O ester), 174.14 (d, $^3J_{C-C-N-P}$=6.3 Hz, C=O ester), 161.36, 161.27 (C6), 161.21, 161.07 (C2), 154.52, 154.45 (C4), 148.07, 148.01 (ipso Naph), 136.22, 136.08 (C10-Naph), 128.78, 128.62 (C-Naph), 127.92, 128.87 (C9-Naph), 127.78, 127.68, 127.55, 127.37, 127.11, 126.44, 126.33, 125.80, 125.55, 122.83, 122.70 (C-Naph), 119.15, 119.11 (C5), 116.23, 115.79 (2d, $^3J_{C-C-O-P}$=2.5 Hz, C2-Naph), 99.76 (C8), 98.05 (C1'), 83.34 (d, $^3J_{C-C-O-P}$=7.5 Hz, C4'), 83.20 (d, $^3J_{C-C-O-P}$=8.8 Hz, C4'), 80.24, 80.21 (C2'), 76.12, 76.05 (C3'), 70.96, 70.95 (CH ester), 69.53, 69.42 (2d, $^2J_{C-O-P}$=5.0 Hz, C5'), 54.23, 54.19 (6OCH$_3$), 51.47, 51.44 (Cα Ala), 31.07, 30.92 (2×OCHCH$_{2a}$), 20.72, 20.67 (2'C CH$_3$), 20.55, 20.44 (2d, $^3J_{C-C-N-P}$=6.3 Hz, CH$_3$ Ala), 14.23, 14.21 (OCHCH$_2$CH$_2$ ester).

$^{31}$P NMR (202 MHz, MeOH-d$_4$) δ 4.21, 3.63

HPLC t$_R$=17.80, 18.72 min

MS (TOF ES+) m/z: 769.12 (MH$^+$, 100%);

HRMS C$_{29}$H$_{35}$N$_6$O$_9$P$_1$I$_1$ Calculated: 769.1248. found: 769.1222.

Example 16

(2S)-Cyclopentyl 2-((((2R,3R,4R,5R)-5-(2-Amino-8-iodo-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

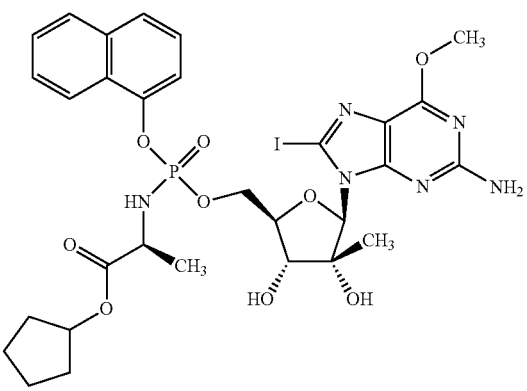 [SMILES: COc1nc(N)nc2c1nc(I)n2[C@@H]1O[C@H](COP(=O)(N[C@@H](C)C(=O)OC2CCCC2)Oc2cccc3ccccc23)[C@@H](O)[C@@]1(C)O]

The general Method B for the synthesis of 5'-phosphoroamidates was used. To a solution of 300 mg (0.67 mmol) of (2R,3R,4R,5R)-2-(2-amino-8-iodo-6-methoxy-9H-purin-9-yl)-5-(hydroxymethyl)-3-methyltetrahydrofuran-3,4-diol in 5 mL of THF, t-BuMgCl 1.37 mL (1.37 mmol), was added followed by naphthalen-1-yl(cyclopentoxy-L-alaninyl)phosphorochloridate 520 mg (1.37 mmol) in 5 mL of THF. After silica gel column chromatography, 80 mg of pure product was obtained in a 15% yield, as an off white solid.

The following are the NMR, HPLC and MS results analyzing the synthesized compound:

$^1$H NMR (500 MHz, MeOH-d$_4$) δ 8.17-8.15, 7.98-7.97 (2m, 1H, H$_8$-naph), 7.87-7.85, 7.78-7.76 (2m, 1H, H$_5$-napht), 7.67, 7.56 (2d, J=8.5 Hz, 1H, H$_4$-napht), 7.53-7.36 (m, 3H, H$_2$, H$_7$, H$_6$-napht), 7.35-7.27 (m, 1H, H$_3$-napht), 5.97, 5.96 (2s, 1H, H$_{1'}$), 4.97-4.92 (m, 1H, CH ester), 4.90-4.79 (m, 2H, H$_{3'}$ and H$_{5'a}$), 4.62-4.54 (m, 1H, H$_{5'b}$), 4.31-4.23 (m, 1H, H$_{4'}$), 4.01, 3.97 (2s, 3H, 6OCH$_3$), 3.95-3.89 (m, 1H, Hα Ala), 1.75-1.70 (m, 2H, 2×CH$_{2a'}$), 1.62-1.59 (m, 6H, 2×CH$_{2a''}$, 2×CH$_2$ ester), 1.28, 1.20 (2d, J=7.0 Hz, 3H, CH$_3$ Ala), 1.03, 1.02 (2×s, 3H, 2'CCH$_3$).

$^{13}$C NMR (126 MHz, MeOH-d$_4$) δ 174.88, 174.61 (2d, $^3J_{C-C-N-P}$=5.0 Hz, C=O ester), 161.37, 161.28 (C6), 161.18, 161.04 (C2), 154.54, 154.47 (C4), 148.04 (d, $^2J_{C-O-P}$=7.5 Hz, ipso Naph), 147.96 (d, $^2J_{C-O-P}$=6.3 Hz, ipso Naph), 136.20, 136.06 (C10-Naph), 128.82, 128.66

(C-Naph), 127.88, 128.74 (2d, $^3J_{C\_C\_O\_P}$=6.3 Hz, C9-Naph), 127.58, 127.40, 127.25, 127.16, 126.48, 126.36, 125.85, 125.62, 122.82, 122.68 (C-Naph), 119.21, 119.17 (C5), 116.26 (d, $^3J_{C\_C\_O\_P}$=3.4 Hz, C2-Naph), 115.85 (d, $^3J_{C\_C\_O\_P}$=2.5 Hz, C2-Naph), 99.79, 99.66 (C8), 98.03, 97.84 (C1'), 83.36 (d, $^3J_{C\_C\_O\_P}$=7.5 Hz, C4'), 83.22 (d, $^3J_{C\_C\_O\_P}$=8.8 Hz, C4'), 80.28, 80.26 (C2'), 79.52, 79.48 (CH ester), 76.19, 76.09 (C3'), 69.57 (d, $^2J_{C\_O\_P}$=6.3 Hz, C5'), 69.22 (d, $^2J_{C\_O\_P}$=5.0 Hz, C5'), 54.33, 54.30 (6OCH$_3$), 51.69, 51.63 (Cα Ala) 33.53, 33.43 (2CH$_2$ ester), 24.64, 24.60 (2CH$_2$ ester), 20.83, 20.79 (2'CCH$_3$), 20.68, 20.60 (2d, $^3J_{C\_C\_N\_P}$=6.3 Hz, CH$_3$ Ala).

$^{31}$P NMR (202 MHz, MeOH-d$_4$) δ 4.25, 3.67

HPLC t$_R$=18.99, 19.81 min

MS (TOF ES+) m/z: 783.14 (MH$^+$, 100%);

HRMS C$_{30}$H$_{37}$N$_6$O$_9$P$_1$I$_1$ Calculated: 783.1404. found: 783.1382.

Example 17

(2S)-Cyclohexyl 2-((((2R,3R,4R,5R)-5-(2-Amino-8-iodo-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

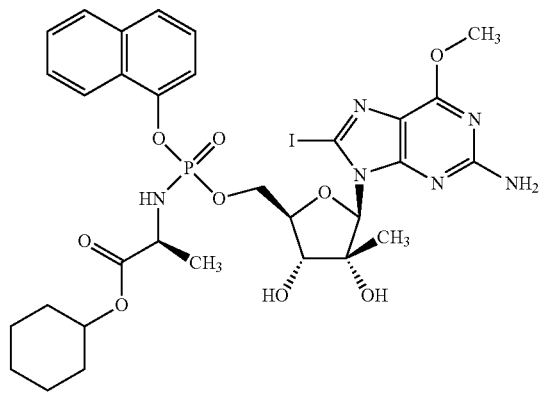 [SMILES: COc1nc(N)nc2c1nc(I)n2[C@@H]1O[C@H](COP(=O)(N[C@@H](C)C(=O)OC2CCCCC2)Oc2cccc3ccccc23)[C@@H](O)[C@@]1(C)O]

The general Method B for the synthesis of 5'-phosphoroamidates was used. To a solution of 300 mg (0.67 mmol) of (2R,3R,4R,5R)-2-(2-amino-8-iodo-6-methoxy-9H-purin-9-yl)-5-(hydroxymethyl)-3-methyltetrahydrofuran-3,4-diol in 5 mL of THF, tBuMgCl 1.37 mL (1.37 mmol), was added followed by naphthalen-1-yl(cyclohexoxy-L-alaninyl)phosphorochloridate 550 mg (1.37 mmol) in 5 mL of THF. After silica gel column chromatography, 75 mg of pure product was obtained in a 14% yield, as an off white solid.

The following are the NMR, HPLC and MS results analyzing the synthesized compound:

$^1$H NMR (500 MHz, MeOH-d$_4$) δ 8.17-8.15, 7.99-7.98 (2m, 1H, H$_8$-naph), 7.86-7.84, 7.77-7.76 (2m, 1H, H$_5$-napht), 7.66, 7.56 (2d, J=8.0 Hz, 1H, H$_4$-napht), 7.52-7.36 (m, 3H, H$_2$, H$_7$, H$_6$-napht), 7.35-7.27 (m, 1H, H$_3$-napht), 5.98, 5.97 (2s, 1H, H$_{1'}$), 4.90-4.81 (m, 2H, H$_{3'}$ and H$_{5'a}$), 4.63-4.51 (m, 2H, H$_{5'b}$ and CH ester), 4.32-4.24 (m, 1H, H$_{4'}$), 4.00, 3.97 (2s, 3H, 6OCH$_3$), 3.99-3.91 (m, 1H, Hα Ala), 1.68-1.63 (m, 4H, 2×CH$_2$), 1.48-1.47 (m, 1H, CH$_{2a'}$ ester), 1.34-1.26 (m, 7H, CH$_{2a''}$ and 3×CH$_2$ ester), 1.29, 1.22 (2d, J=7.0 Hz, 3H, CH$_3$ Ala), 1.03 (s, 3H, 2'CCH$_3$).

$^{13}$C NMR (126 MHz, MeOH-d$_4$) δ 174.50 (d, $^3J_{C\_C\_N\_P}$=5.0 Hz, C=O ester), 174.24 (d, $^3J_{C\_C\_N\_P}$=6.3 Hz, C=O ester), 161.36, 161.27 (C6), 161.20, 161.06 (C2), 154.53, 154.46 (C4), 148.06 (d, $^2J_{C\_O\_P}$=7.5 Hz, ipso Naph), 147.99 (d, $^2J_{C\_O\_P}$=8.8 Hz, ipso Naph), 136.23, 136.09 (C10-Naph), 128.79, 128.62 (C-Naph), 127.90, 128.76 (2d, $^3J_{C\_C\_O\_P}$=6.3 Hz, C9-Naph), 127.54, 127.37, 127.11, 126.46, 126.33, 125.80, 125.55, 122.83, 122.70 (C-Naph), 119.16, 119.11 (C5), 116.23, 115.80 (2d, $^3J_{C\_C\_O\_P}$=3.4 Hz, C2-Naph), 99.73, 99.65 (C8), 98.04 (C1'), 83.37, 83.21 (2d, $^3J_{C\_C\_O\_P}$=7.5 Hz, C4'), 80.24 (C2'), 76.12, 76.05 (C3'), 74.88 (CH ester), 69.56, 69.43 (2d, $^2J_{C\_O\_P}$=5.0 Hz, C5'), 54.24, 54.22 (6OCH$_3$), 51.74, 51.71 (Cα Ala) 32.32, 32.27 (2CH$_2$ ester), 26.37 (2CH$_2$ ester), 24.55 (CH$_2$ ester), 20.73, 20.69 (2'CCH$_3$), 20.72, 20.62 (2d, $^3J_{C\_C\_N\_P}$=6.3 Hz, CH$_3$ Ala).

$^{31}$P NMR (202 MHz, MeOH-d$_4$) δ 4.23, 3.66

HPLC t$_R$=20.35, 21.16 min

MS (TOF ES+) m/z: 819.14 (MNa$^+$, 100%);

HRMS C$_{31}$H$_{38}$N$_6$O$_9$P$_1$I$_1$Na$_1$ Calculated: 819.1380. found: 819.1390.

Example 18

(2S)-Tetrahydro-2H-pyran-4-yl 2-((((2R,3R,4R,5R)-5-(2-Amino-8-iodo-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

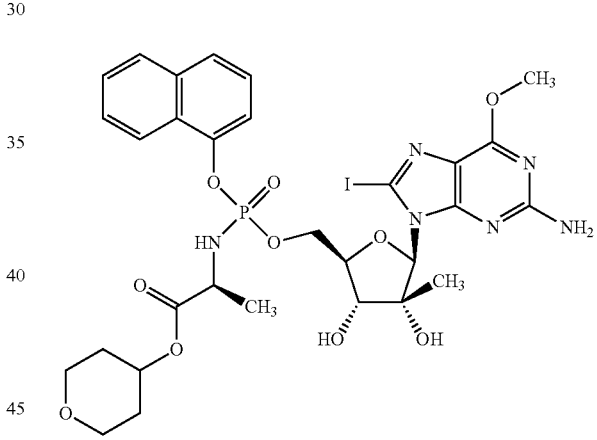

The general Method B for the synthesis of 5'-phosphoroamidates was used. To a solution of 300 mg (0.67 mmol) of (2R,3R,4R,5R)-2-(2-amino-8-iodo-6-methoxy-9H-purin-9-yl)-5-(hydroxymethyl)-3-methyltetrahydrofuran-3,4-diol in 5 mL of THF, t-BuMgCl 1.37 mL (1.37 mmol), was added followed by naphthalen-1-yl(tetrahydropyroxy-L-alaninyl) phosphorochloridate 550 mg (1.37 mmol) in 5 mL of THF. After silica gel column chromatography, 150 mg of pure product was obtained in a 27% yield, as an off white solid.

The following are the NMR, HPLC and MS results analyzing the synthesized compound:

$^1$H NMR (500 MHz, MeOH-d$_4$) δ 8.18-8.16, 7.99-7.98 (2m, 1H, H$_8$-naph), 7.86-7.84, 7.77-7.76 (2m, 1H, H$_5$-napht), 7.66, 7.56 (2d, J=8.0 Hz, 1H, H$_4$-napht), 7.52-7.36 (m, 3H, H$_2$, H$_7$, H$_6$-napht), 7.33-7.27 (m, 1H, H$_3$-napht), 5.98, 5.97 (2s, 1H, H$_{1'}$), 4.90-4.84 (m, 2H, H$_{3'}$ and H$_{5'a}$), 4.77-4.68 (m, 1H, CH ester) 4.63-4.51 (m, 1H, H$_{5'b}$), 4.32-4.24 (m, 1H, H$_{4'}$), 4.03-3.95 (m, 1H, Hα Ala), 4.01, 3.97 (2s, 3H, 6OCH$_3$), 3.80-3.74 (m, 2H, OCH$_2$ ester), 3.47-3.40 (m, 2H, OCH$_2$ ester), 1.77-1.69 (m, 2H, CHCH₂ ester), 1.52-1.43 (m, 2H, CHCH₂ ester), 1.30, 1.23 (2d, J=6.5 Hz, 3H, CH₃ Ala), 1.03, 1.02 (s, 3H, 2'CCH₃).

¹³C NMR (126 MHz, MeOH-d₄) δ 174.30 (d, $^3J_{C-C-N-P}$=4.3 Hz, C=O ester), 174.06 (d, $^3J_{C-C-N-P}$=6.3 Hz, C=O ester), 161.37, 161.29 (C6), 161.21, 161.06 (C2), 154.55, 154.46 (C4), 148.03 (d, $^2J_{C-O-P}$=7.5 Hz, ipso Naph), 147.97 (d, $^2J_{C-O-P}$=8.8 Hz, ipso Naph), 136.23, 136.08 (C10-Naph), 128.82, 128.65 (C-Naph), 127.89 (d, $^3J_{C-C-O-P}$=6.3 Hz, C9-Naph), 127.74 (d, $^3J_{C-C-O-P}$=5.0 Hz, C9-Naph), 127.58, 127.41, 127.15, 126.49, 126.37, 125.85, 125.59, 122.81, 122.67 (C-Naph), 119.19, 119.13 (C5), 116.27, 115.82 (2d, $^3J_{C-C-O-P}$=3.4 Hz, C2-Naph), 99.78, 99.66 (C8), 98.05 (C1'), 83.40 (d, $^3J_{C-C-O-P}$=6.3 Hz, C4'), 83.23 (d, $^3J_{C-C-O-P}$=7.5 Hz, C4'), 80.24, 80.22 (C2'), 76.13, 76.04 (C3'), 71.25, 71.22 (CH ester), 69.59 (d, $^2J_{C-O-P}$=6.3 Hz, C5'), 69.44 (d, $^2J_{C-O-P}$=5.0 Hz, C5'), 66.07, 66.01, 65.99 (O(CH₂)₂ ester), 54.28, 54.24 (6OCH₃), 51.70, 51.66 (Cα Ala) 32.50, 32.44, 32.41 (CH(CH₂)₂ ester), 26.37 (2CH₂ ester), 24.55 (CH₂ ester), 20.75, 20.71 (2'CCH₃), 20.63, 20.55 (2d, $^3J_{C-C-N-P}$=6.3 Hz, CH₃ Ala).

³¹P NMR (202 MHz, MeOH-d₄) δ 4.17, 3.61

HPLC $t_R$=14.91, 15.71 min

MS (TOF ES+) m/z: 799.13 (MH⁺, 100%);

HRMS C₃₀H₃₇N₆O₁₀P₁I₁ Calculated: 799.1354. found: 799.1349.

Example 19

(2S)-Benzyl 2-((((2R,3R,4R,5R)-5-(2-Amino-8-iodo-6-methoxy-9H-purin-9-yl)-3,4-dihydroxy-4-methyltetrahydrofuran-2-yl)methoxy)(naphthalen-1-yloxy)phosphorylamino)-4-(methylthio)butanoate was synthesized as follows

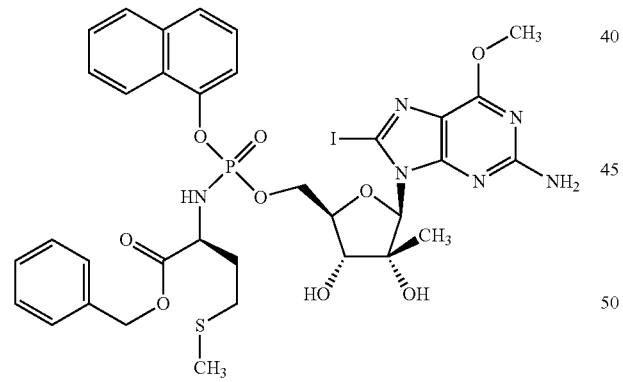

The general Method B for the synthesis of 5'-phosphoroamidates was used. To a solution of 300 mg (0.67 mmol) of (2R,3R,4R,5R)-2-(2-amino-8-iodo-6-methoxy-9H-purin-9-yl)-5-(hydroxymethyl)-3-methyltetrahydrofuran-3,4-diol in 5 mL of THF, t-BuMgCl 1.37 mL (1.37 mmol), was added followed by naphthalen-1-yl(benzoxy-L-methioninyl)phosphorochloridate (640 mg, 1.37 mmol) in 5 mL of THF. After silica gel column chromatography, 180 mg of pure product was obtained in a 30% yield, as an off white solid.

The following are the NMR, HPLC and MS results analyzing the synthesized compound:

¹H NMR (500 MHz, MeOH-d₄) δ 8.18-8.16, 8.00-7.99 (2m, 1H, H₈-naph), 7.85-7.83, 7.76-7.75 (2m, 1H, H₅-napht), 7.64, 7.55 (2d, J=8.5 Hz, 1H, H₄-napht), 7.50-7.41 (m, 3H, H₂, H₇, H₆-napht), 7.36-7.29 (m, 1H, H₃-napht), 7.26-7.23 (m, 5H, Ph), 5.99, 5.98 (2s, 1H, H₁'), 5.03-4.87 (m, 2H, CH₂ ester), 4.85-4.80 (m, 2H, H₃', and H₅'ₐ), 4.65-4.57 (m, 1H, H₅'ᵦ), 4.34-4.24 (m, 1H, H₄'), 4.16-4.68 (m, 1H, Hα Met), 3.98, 3.95 (2s, 3H, 6OCH₃), 2.28 (t, J=7.0 Hz, 2H, CH₂—S), 1.89-1.75 (m, 2H, CHCH₂ Met), 1.86, 1.83 (2s, 3H, SCH₃ Met) 1.03 (s, 3H, 2'CCH₃).

¹³C NMR (126 MHz, MeOH-d₄) δ 174.04, 173.86 (2d, $^3J_{C-C-N-P}$=5.0 Hz, C=O ester), 161.37, 161.26 (C6), 161.17, 161.03 (C2), 154.53, 154.45 (C4), 148.01 (d, $^2J_{C-O-P}$=7.5 Hz, ipso Naph), 147.93 (d, $^2J_{C-O-P}$=6.3 Hz, ipso Naph), 137.05, 137.01 (ipso Ph), 136.22, 136.06 (C10-Naph), 129.67, 129.56, 129.54, 129.34, 129.32, 129.28, 128.81, 128.66 (C-Naph and Ph), 127.85 (d, $^3J_{C-C-O-P}$=6.3 Hz, C9-Naph), 127.75 (d, $^3J_{C-C-O-P}$=5.0 Hz, C9-Naph), 127.60, 127.45, 127.23, 126.48, 126.37, 125.86, 125.68, 122.89, 122.75 (C-Naph), 119.19, 119.14 (C5), 116.19 (d, $^3J_{C-C-O-P}$=3.8 Hz, C2-Naph), 115.98 (d, $^3J_{C-C-O-P}$=2.5 Hz, C2-Naph), 99.79, 98.02 (C1'), 83.37, 83.15 (2d, $^3J_{C-C-O-P}$=7.5 Hz, C4'), 80.27, 80.22 (C2'), 76.14, 76.05 (C3'), 69.64 (d, $^2J_{C-O-P}$=6.3 Hz, C5'), 69.59 (d, $^2J_{C-O-P}$=5.0 Hz, C5'), 67.99 (CH₂ ester), 55.02 (CαMet), 54.29, 54.25 (6OCH₃), 34.44 (d, $^3J_{C-C-N-P}$=6.3 Hz, CβMet), 34.33 (d, $^3J_{C-C-N-P}$=7.5 Hz, CβMet), 30.68 (CH₂S Met), 20.79, 20.72 (2'CCH₃), 15.22 (CH₃ Met).

³¹P NMR (202 MHz, MeOH-d₄) δ 4.17, 3.61

HPLC $t_R$=19.93, 20.75 min

MS (TOF ES+) m/z: 865.13 (MH⁺, 100%);

HRMS C₃₀₄H₃₉N₆O₁₀P₁S₁I₁ Calculated: 865.1282. found: 865.1256.

Example 20

(2S)-Benzyl 2-((((2R,3R,4R,5R)-5-(2-Amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate was synthesized as follows

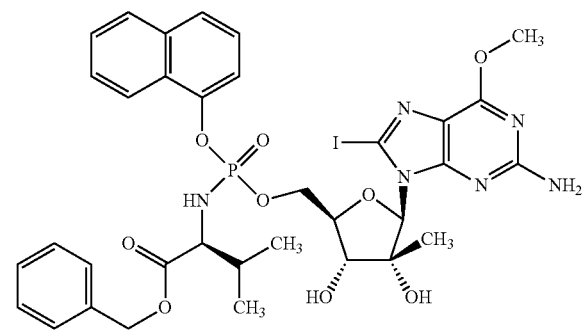 [SMILES: COc1nc(N)nc2c1nc(I)n2[C@@H]1O[C@H](COP(=O)(N[C@H](C(=O)OCc2ccccc2)C(C)C)Oc2cccc3ccccc23)[C@@H](O)[C@@]1(C)O]

The general Method B for the synthesis of 5'-phosphoroamidates was used. To a solution of 300 mg (0.67 mmol) of nucleoside in 5 mL of THF, t-BuMgCl 1.37 mL (1.37 mmol), was added followed by naphthalen-1-yl(benzoxy-L-valinyl) phosphorochloridate 592 mg (1.37 mmol) in 5 mL of THF. After silica gel column chromatography, 129 mg of pure product was obtained in a 23% yield, as an off white solid.

The following are the NMR results analyzing the synthesized compound:

¹H NMR (500 MHz, MeOH-d₄) δ 8.14, 7.98 (2d, 1H, J=7.5 Hz, H₈-naph), 7.82-7.80, 7.73-7.71 (m, 1H, H₅-napht), 7.62, 7.51 (2d, J=7.5 Hz, 1H, H$_4$-napht), 7.48-7.38 (m, 3H, H$_2$, H$_7$, H$_6$-napht), 7.35-7.29 (m, 1H, H$_3$-napht), 7.24-7.19 (m, 5H, Ph), 6.01, 5.99 (2s, 1H, H$_{1'}$), 4.97-4.88 (m, 2H, CH$_2$ ester), 4.85-4.79 (m, 2H, H$_{3'}$ and H$_{5'a}$), 4.64-4.61 (m, 1H, H$_{5'b}$), 4.33-4.28 (m, 1H, H$_{4'}$), 3.97, 3.94 (2s, 3H, 6OCH$_3$), 3.80-3.72 (m, 1H, Hα, Val), 2.04-1.83 (m, 1H, Hβ, Val), 1.04, 1.02 (2s, 3H, 2'CCH$_3$), 0.79, 0.70 (2d, J=6.5 Hz, 3H, CH$_3$ Val), 0.77, 0.74 (2d, J=6.0 Hz, 3H, CH$_3$ Val).

$^{13}$C NMR (126 MHz, MeOH-d$_4$) δ 174.02 (d, $^3J_{C-C-N-P}$=3.7 Hz, C=O ester), 173.84 (2d, $3J_{C-C-N-P}$=2.5 Hz, C=O ester), 161.38, 161.28 (C6), 161.20, 161.16 (C2), 154.53, 154.47 (C4), 148.04, 147.96 (2d, $^2J_{C-O-P}$=7.5 Hz, ipso Naph), 136.97, 136.93 (ipso Ph), 136.18, 136.03 (C10-Naph), 129.86, 129.73, 129.67, 129.64, 129.62, 129.54, 129.48, 129.43, 129.35, 128.83, 128.66, 127.90, 127.85, 127.73, 127.59, 127.45, 127.18, 126.52, 126.37, 125.85, 125.64, 122.89, 122.76 (C-Naph and Ph), 119.27, 119.24 (C5), 116.22 (d, $^2J_{C-C-O-P}$=3.8 Hz, C2-Naph), 115.95 (d, $^2J_{C-C-O-P}$=2.5 Hz, C2-Naph), 99.83, 99.66 (C8), 97.99 (C1'), 83.50, 83.24 (2d, $^3J_{C-C-O-P}$=7.5 Hz, C4'), 80.30, 80.24 (C2'), 76.16, 76.04 (C3'), 69.72, 69.40 (2d, $^2J_{C-O-P}$=5.0 Hz, C5'), 67.84, 67.76 (CH$_2$ ester), 61.85, 61.76 (Cα Val), 54.39, 54.37 (6OCH$_3$), 33.36 (d, $^3J_{C-C-N-P}$=6.3 Hz, Cβ Val), 33.23 (d, $^3J_{C-C-N-P}$=7.5 Hz, Cβ Val), 20.90, 20.81 (2'CCH$_3$), 19.42, 19.37, 18.36, 18.31 (CH$_3$ Val)

$^{31}$P NMR (202 MHz, MeOH-d$_4$) δ 4.97, 4.37.

HPLC t$_R$=21.65, 22.11 min

MS (TOF ES+) m/z: 833.15 (MH$^+$, 100%);

HRMS C$_{34}$H$_{39}$N$_6$O$_9$P$_1$I$_1$ Calculated: 833.1561. found: 833.1540.

General Methods for Preparation of Diamidates

Method A: Symmetrical Phosphoroamidates Using Triethyl Phosphate and Phosphoryl Chloride To a solution of the nucleoside (for example (2R,3R,4R,5R)-2-(2-amino-8-iodo-6-methoxy-9H-purin-9-yl)-5-(hydroxymethyl)-3-methyltetrahydrofuran-3,4-diol) (1 equiv) in anhydrous triethyl phosphate is added phosphoryl chloride (2 equiv) at 0° C. The reaction mixture is stirred 24 h at 5° C. Anhydrous dichloromethane is added to the reaction mixture followed by amino acid ester (5 equiv) and diisopropylethylamine (10 equiv) at 0° C. After stirring at 5° C. for 5 days, water is added and the layers are separated. The aqueous phase is extracted with dichloromethane and the organic phase washed with brine. The combined organic layers are dried over anhyd sodium sulfate, filtered and evaporated to dryness. The resulting residue is purified by silica gel column chromatography using as eluent a gradient of methanol in dichloromethane. A subsequent repurification, if necessary, is accomplished either by preparative HPLC (gradient of methanol in water) or preparative TLC.

Method B: Symmetrical Phosphoroamidates Using THF and Phosphoryl Chloride

To a suspension of nucleoside, (for example (2R,3R,4R,5R)-2-(2-amino-8-iodo-6-methoxy-9H-purin-9-yl)-5-(hydroxymethyl)-3-methyltetrahydrofuran-3,4-diol) (1 equiv) in anhyd tetrahydrofuran is added triethylamine (1.2 equiv). After stirring for 30 min at room temperature, phosphoryl chloride (1.2 equiv) is added dropwise at −78° C. The reaction mixture is stirred 30 min at −78° C. then allowed to warm to room temperature over 30 min. Anhydrous dichloromethane is added, followed by amino acid ester (5 equiv) and triethylamine (10 equiv) at −78° C. After stirring at room temperature for 20 h, water is added and the layers are separated. The aqueous phase is extracted with dichloromethane and the organic phase washed with brine. The combined organic layers are dried over anhyd sodium sulfate, filtered and evaporated to dryness. The resulting residue is purified by silica gel column chromatography using as eluent a gradient of methanol in dichloromethane. In some cases, a subsequent repurification is necessary either by preparative HPLC (gradient of methanol in water) or preparative TLC.

Method C: Asymmetrical Phosphorodiamidates with Phosphorus Chloride

To a suspension of the nucleoside (1 equiv) in anhydrous tetrahydrofuran, is added triethylamine (1.2 equiv). After stirring for 30 min at room temperature, phosphoryl chloride (1.2 equiv) is added dropwise at −78° C. The reaction mixture is stirred 30 min at −78° C. then allowed to warm to room temperature over 30 min. Anhydrous dichloromethane is added, followed by a first amino acid ester or amine (1 equiv) and triethylamine (2 or 1 equiv respectively) at −78° C. The solution is warmed to room temperature and monitored by $^{31}$P NMR. When NMR indicates completion of the reaction (no starting material, presence of mono-substituted product) a second amino acid ester or amine (5 equiv) is added followed by the addition of triethylamine (10 or 5 equiv respectively) at −78° C. After stirring at room temperature for 20 h, water is added and the layers are separated. The aqueous phase is extracted with dichloromethane and the organic phase is washed with brine. The combined organic layers are dried over anhydrous sodium sulfate, filtered and evaporated to dryness. The resulting residue is purified by silica gel column chromatography using as eluent a gradient of methanol in chloroform (0-5%).

Method D: Asymmetrical Phosphorodiamidates Using Amino Acid Ester Phosphodichloridate To a suspension of the nucleoside (1 equiv) in anhydrous tetrahydrofuran is added triethylamine (1.2 equiv). After stirring for 30 min at room temperature an amino acid ester phosphodichloridate (2 equiv) is added. After stirring at room temperature for 20 h, the solution is cooled to −78° C. and a primary amine is added (5 equiv) followed by triethylamine (5 equiv). The solution is warmed to room temperature and stirred for 20 h. Water is added and the layers are separated. The aqueous phase is extracted with dichloromethane and the organic phase washed with brine. The combined organic layers are dried over anhydrous sodium sulfate, filtered and evaporated to dryness. The resulting residue is purified by silica gel column chromatography using as eluent a gradient of methanol in chloroform (0-5%)

Example 21

(2S,2'S)-Benzyl 2,2'-((((2R,3R,4R,5R)-5-(2-Amino-8-iodo-6-methoxy-9H-purin-9-yl)-3,4-dihydroxy-4-methyltetrahydrofuran-2-yl)methoxy)phosphoryl)bis (azanediyl)dipropanoate was synthesized as follows

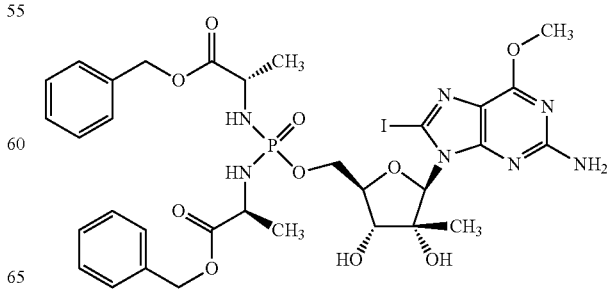

The general Method B for the synthesis of 5'-phosphorodiamidates was used. A solution of 2-amino-8-iodo-6-methoxy-9-(2-C-methyl-β-D-ribofuranosyl)purine (300 mg, 0.69 mmol) in anhyd tetrahydrofuran (5 mL) was allowed to react with triethylamine (96 μL, 0.69 mmol) and phosphorus oxychloride (60 μL, 0.69 mmol). Anhydrous dichloromethane (5 mL), and the tosylate salt of benzyl-L-alanine (1.21 g, 3.43 mmol) and triethylamine (0.96 mL, 6.86 mmoles) were added and reaction was stirred overnight. After work-up and silica gel column chromatography, 230 mg of the product was obtained in 40% yield as an off white solid.

The following are the NMR and HPLC results analyzing the synthesized compound:

$^1$H NMR (500 MHz, MeOH-d$_4$) δ 7.35-7.23 (m, 10H, 2Ph), 6.01 (2s, 1H, H$_{1'}$), 5.09, 5.05, 4.94, 4.88 (2AB, J$_{AB}$=12.0 Hz, 2H, CH$_2$ ester), 4.88-4.85 (m, 1H, H$_{3'}$), 4.59-4.56 (m, 1H, H$_{5'a}$), 4.47-4.43 (m, 1H, H$_{5'b}$), 4.25-4.21 (m, 1H, H$_{4'}$), 4.01-3.88 (m, 2H, 2×Hα, Ala), 3.99 (s, 3H, 6OCH$_3$), 1.31 (d, J=7.0 Hz, 3H, CH$_3$ Ala), 1.20 (d, J=7.5 Hz, 3H, CH$_3$ Ala), 1.04 (s, 3H, 2'CCH$_3$).

$^{13}$C NMR (126 MHz, MeOH-d$_4$) δ 175.55 (d, $^3$J$_{C-C-N-P}$=5.0 Hz, C=O ester), 175.44 (d, $^3$J$_{C-C-N-P}$=5.0 Hz, C=O ester), 161.44 (C6), 161.15 (C2), 154.52 (C4), 137.28, 137.19 (ipso Ph), 129.99, 129.67, 129.64, 129.44, 129.36, 129.27, 128.35, 128.07 (C-Ph), 119.17 (C5), 99.89 (C8), 97.98 (C1'), 83.35 (d, $^3$J$_{C-C-O-P}$=6.3 Hz, C4'), 80.39 (C2'), 76.16 (C3'), 67.93 (d, $^2$J$_{C-O-P}$=5.0 Hz, C5'), 67.60, 67.57 (CH$_2$ ester), 54.49 (6OCH$_3$), 51.09, 51.01 (2CαAla), 21.28 (2'CCH$_3$), 20.93 (d, $^3$J$_{C-C-N-P}$=5.0 Hz, CH$_3$ Ala), 20.84 (d, $^3$J$_{C-C-N-P}$=5.0 Hz, CH$_3$ Ala)

$^{31}$P NMR (202 MHz, MeOH-d$_4$) δ 13.86

HPLC t$_R$=18.60 min

Example 22

(2S,2'S)-Bis(3,3-Dimethylbutyl) 2,2'-(((((2R,3R,4R,5R)-5-(2-Amino-8-iodo-6-methoxy-9H-purin-9-yl)-3,4-dihydroxy-4-methyltetrahydrofuran-2-yl)methoxy)phosphoryl)bis(azanediyl)dipropanoate was synthesized as follows

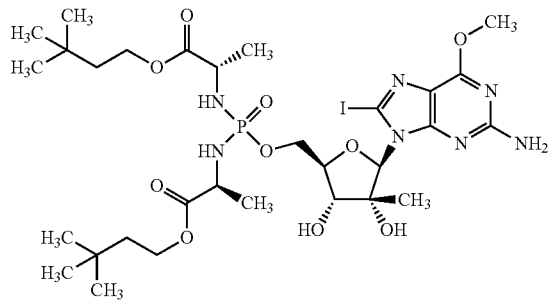 [SMILES: COc1nc(N)nc2c1nc(I)n2[C@@H]1O[C@H](COP(=O)(N[C@@H](C)C(=O)OCCC(C)(C)C)N[C@@H](C)C(=O)OCCC(C)(C)C)[C@@H](O)[C@@]1(C)O]

The general Method B for the synthesis of 5'-phosphorodiamidates was used. A solution of 2-amino-8-iodo-6-methoxy-9-(2-C-methyl-β-D-ribofuranosyl)purine (300 mg, 0.69 mmol) in anhyd tetrahydrofuran (5 mL) was allowed to react with triethylamine (96 μL, 0.69 mmol) and phosphorus oxychloride (60 μL, 0.69 mmol). Anhydrous dichloromethane (5 mL), and the tosylate salt of 3,3-dimethylbutyl-L-alanine (1.18 g, 3.43 mmol) and triethylamine (0.96 mL, 6.86 mmoles) were added and reaction was stirred overnight. After work-up and silica gel column chromatography, 130 mg of the product was obtained in 23% yield as an off white solid.

The following are the NMR, HPLC and MS results analyzing the synthesized compound:

$^1$H NMR (500 MHz, MeOH-d$_4$) 5.98 (s, 1H, H$_{1'}$), 4.89-4.81 (m, 2H, H$_{3'}$), 4.63-4.57 (m, 1H, H$_{5'a}$), 4.41-4.37 (m, 1H, H$_{5'b}$), 4.21-4.09 (m, 5H, H$_{4'}$ and 2 OCH$_2$ ester), 4.04 (s, 3H, 6OCH$_3$), 3.92-3.86 (m, 1H, Hα Ala), 3.85-3.80 (m, 1H, Hα Ala), 1.57 (t, J=7.0 Hz, 2H, CH$_2$ ester), 1.52 (t, J=7.0 Hz, 2H, CH$_2$ ester), 1.34 (d, J=7.0 Hz, 3H, CH$_3$ Ala), 1.20 (d, J=7.0 Hz, 3H, CH$_3$ Ala), 1.03 (s, 3H, 2'CCH$_3$), 0.97 (s, 9H, 3×CH$_3$ ester), 0.94 (s, 9H, 3×CH$_3$ ester).

$^{13}$C NMR (126 MHz, MeOH-d$_4$) δ 175.74 (d, $^3$J$_{C-C-N-P}$=5.0 Hz, C=O ester), 175.56 (d, $^3$J$_{C-C-N-P}$=5.0 Hz, C=O ester), 161.44 (C6), 161.17 (C2), 154.58 (C4), 119.13 (C5), 99.72 (C8), 97.98 (C1'), 83.33 (d, $^3$J$_{C-C-O-P}$=7.5 Hz, C4'), 80.34 (C2'), 76.13 (C3'), 67.57 (d, $^2$J$_{C-O-P}$=5.0 Hz, C5'), 63.95, 63.89 (OCH$_2$ ester), 54.238 (6OCH$_3$), 51.03 (CαAla), 50.91 (CαAla), 42.87 (CH$_2$ ester), 30.63 (C ester), 30.61 (C ester), 30.13 (3×CH$_3$ ester), 30.11 (3×CH$_3$ ester), 20.90 (CH$_3$ Ala), 20.85 (CH$_3$ Ala), 20.62 (2'CCH$_3$)

$^{31}$P NMR (202 MHz, MeOH-d$_4$) 13.96

HPLC t$_R$=22.51 min

MS (TOF ES+) m/z: 828.25 (M+Na$^+$, 100%);

HRMS C$_{30}$H$_{52}$N$_7$O$_{10}$P$_1$I$_1$ calculated: 828.2558. found 828.2524.

Example 23

(2S,2'S)-Neopentyl 2,2'-(((((2R,3R,4R,5R)-5-(2-Amino-8-iodo-6-methoxy-9H-purin-9-yl)-3,4-dihydroxy-4-methyltetrahydrofuran-2-yl)methoxy)phosphoryl)bis(azanediyl)dipropanoate was synthesized as follows

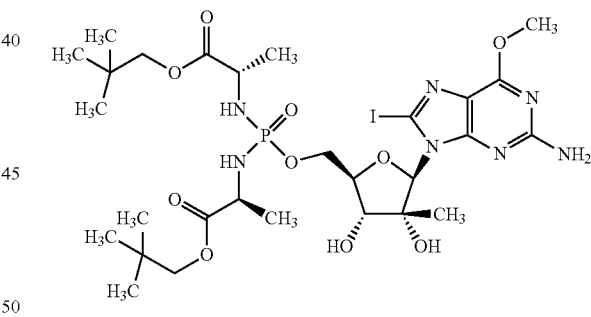

The general Method B for the synthesis of 5'-phosphorodiamidates was used. A solution of 2-amino-8-iodo-6-methoxy-9-(2-C-methyl-β-D-ribofuranosyl)purine (300 mg, 0.69 mmol) in anhyd tetrahydrofuran (5 mL) was allowed to react with triethylamine (96 μL, 0.69 mmol) and phosphorus oxychloride (60 μL, 0.69 mmol). Anhydrous dichloromethane (5 mL), and the tosylate salt of 2,2-dimethylpropyl-L-alanine (1.14 g, 3.43 mmol) and triethylamine (0.96 mL, 6.86 mmoles) were added and reaction was stirred overnight. After work-up and silica gel column chromatography, 50 mg of the product was obtained in 10% yield as an off white solid.

The following are the NMR, HPLC and MS results analyzing the synthesized compound:

$^1$H NMR (500 MHz, MeOH-d$_4$) 5.98 (s, 1H, H$_{1'}$), 4.91-4.83 (m, 2H, H$_{3'}$), 4.63-4.57 (m, 1H, H$_{5'a}$), 4.42-4.38 (m, 1H,

H$_{5'b}$), 4.21-4.18 (m, 1H, H$_{4'}$), 4.04 (s, 3H, 6OCH$_3$), 3.97-3.90 (m, 2H, 2Hα Ala), 3.78, 3.75, 3.67, 3.61 (2AB, J$_{AB}$=10.5 Hz, 2H, CH$_2$ ester), 1.38 (d, J=7.0 Hz, 3H, CH$_3$ Ala), 1.24 (d, J=7.0 Hz, 3H, CH$_3$ Ala), 1.04 (2s, 3H, 2'CCH$_3$), 0.96 (s, 9H, 3×CH$_3$ ester), 0.91 (s, 9H, 3×CH$_3$ ester).

$^{13}$C NMR (126 MHz, MeOH-d$_4$) δ 175.74 (d, $^3$J$_{C-C-N-P}$=5.0 Hz, C=O ester), 175.55 (d, $^3$J$_{C-C-N-P}$=6.3 Hz, C=O ester), 161.40 (C6), 161.27 (C2), 154.64 (C4), 119.12 (C5), 99.76 (C8), 98.00 (C1'), 83.35 (d, 3J$_{C-C-O-P}$=7.5 Hz, C4'), 80.29 (C2'), 76.07 (C3'), 75.35, 75.29 (CH$_2$ ester), 67.66 (d, $^2$J$_{C-O-P}$=5.0 Hz, C5'), 54.24 (6OCH$_3$), 51.05 (Cα Ala), 50.92 (Cα Ala), 32.36 (C ester), 32.29 (C ester), 26.87 (3×CH$_3$ ester), 26.80 (3×CH$_3$ ester), 21.07 (CH$_3$ Ala), 21.03 (CH$_3$ Ala), 20.78 (2'CCH$_3$)

$^{31}$P NMR (202 MHz, MeOH-d$_4$) 13.89

HPLC t$_R$=15.12 min

MS (TOF ES+) m/z: 800.22 (M+Na$^+$, 100%);

HRMS C$_{28}$H$_{48}$N$_7$O$_{10}$P$_1$I$_1$ calculated: 800.2245. found 800.2212.

Example 24

(2S,2'S)-Neopentyl 2,2'-((((2R,3R,4R,5R)-5-(2-Amino-8-bromo-6-methoxy-9H-purin-9-yl)-3,4-dihydroxy-4-methyltetrahydrofuran-2-yl)methoxy) phosphoryl)bis(azanediyl)dipropanoate was synthesized as follows

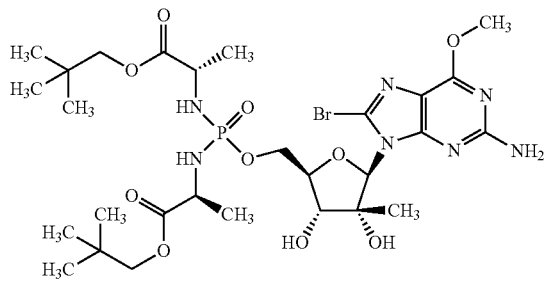 [SMILES: COc1nc(N)nc2c1nc(Br)n2[C@@H]1O[C@H](COP(=O)(N[C@@H](C)C(=O)OCC(C)(C)C)N[C@@H](C)C(=O)OCC(C)(C)C)[C@@H](O)[C@@]1(C)O]

Step 1: (2S,2'S)-Neopentyl 2,2'-((((2R,3R,4R,5R)-5-(2-Amino-6-methoxy-9H-purin-9-yl)-3,4-dihydroxy-4-methyltetrahydrofuran-2-yl)methoxy)phosphoryl)bis(azanediyl)dipropanoate

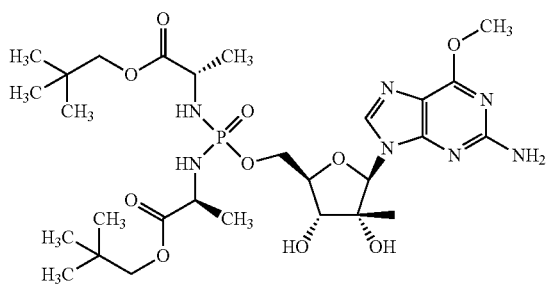 [SMILES: COc1nc(N)nc2c1ncn2[C@@H]1O[C@H](COP(=O)(N[C@@H](C)C(=O)OCC(C)(C)C)N[C@@H](C)C(=O)OCC(C)(C)C)[C@@H](O)[C@@]1(C)O]

Using the General Method B for phosphordiamidates above, a suspension of (2R,3R,4R,5R)-2-(2-amino-6-methoxy-9H-purin-9-yl)-5-(hydroxymethyl)-3-methyltetrahydrofuran-3,4-diol (250 mg, 0.803 mmole) in anhydrous tetrahydrofuran (4 mL) was combined with triethylamine (135 μL, 0.964 mmole) and phosphoryl chloride (89 μL, 0.964 mmole). Anhydrous dichloromethane (4 mL), the tosylate salt of neopentyloxy-L-alanine (1.33 g, 4.02 mmol) and triethylamine (1.12 mL, 8.03 mmol) were added to the mixture from step 1. After work-up and silica gel column chromatography, 151 mg of the product was obtained in 28% yield as an off white solid.

The following are the NMR results of the synthesized compound:

$^1$H NMR (500 MHz, MeOH-d$_4$) δ 7.98 (s, 1H), 5.99 (s, 1H), 4.41-4.36 (m, 2H), 4.29 (d, 1H, J=9.0), 4.22-4.16 (m, 1H), 4.07 (s, 3H), 4.04-3.91 (m, 2H), 3.87, 3.85, 3.84, 3.82 (2 AB system, JAB=10.0, 2H), 3.75, 3.73, 3.70, 3.68 (2 AB system, JAB=10.0, 2H), 1.40 and 1.36 (2d, 6H, J=7.1), 0.99 (s, 3H), 0.93 and 0.94 (2s, 18H).

$^{31}$P NMR (202 MHz, MeOH-d$_4$) δ 14.01.

Step 2: (2S,2'S)-Neopentyl 2,2'-((((2R,3R,4R,5R)-5-(2-Amino-6-methoxy-9H-purin-9-yl)-3,4-dihydroxy-4-methyltetrahydrofuran-2-yl)methoxy)phosphoryl)bis(azanediyl) dipropanoate (200 mg, 0.30 mmol) was suspended in MeOH (10 mL) and 1 mol equiv of NBS (53 mg, 0.30 mmol) was added. The mixture was stirred at room temperature for 18 h. After that time, solution was concentrated and the resulting solid was purified by silica gel chromatography using 1-4% (gradient) of MeOH in chloroform to yield 56 mg (25% yield) of the desired product.

The following are the NMR, HPLC and MS results analyzing the synthesized compound:

$^1$H NMR (500 MHz, MeOH-d$_4$) 6.04 (s, 1H, H$_{1'}$), 4.91-4.80 (m, 2H, H$_{3'}$), 4.63-4.58 (m, 1H, H$_{5'a}$), 4.41-4.37 (m, 1H, H$_{5'b}$), 4.22-4.18 (m, 1H, H$_{4'}$), 4.04 (s, 3H, 6OCH$_3$), 3.97-3.88 (m, 2H, 2Hα Ala), 3.77, 3.76, 3.66, 3.60 (2AB, J$_{AB}$=10.5 Hz, 2H, CH$_2$ ester), 1.38 (d, J=7.0 Hz, 3H, CH$_3$ Ala), 1.25 (d, J=7.0 Hz, 3H, CH$_3$ Ala), 1.06 (s, 3H, 2'CCH$_3$), 0.96 (s, 9H, 3×CH$_3$ ester), 0.91 (s, 9H, 3×CH$_3$ ester).

$^{13}$C NMR (126 MHz, MeOH-d$_4$) δ 175.72 (d, $^3$J$_{C-C-N-P}$=5.0 Hz, C=O ester), 175.53 (d, 3J$_{C-C-N-P}$=7.5 Hz, C=O ester), 161.63 (C6), 161.47 (C2), 154.94 (C4), 125.83 (C8), 116.23 (C5), 95.86 (C1'), 83.40 (d, $^3$J$_{C-C-O-P}$=6.3 Hz, C4'), 80.24 (C2'), 76.00 (C3'), 75.34, 75.29 (CH$_2$ ester), 67.61 (d, $^2$J$_{C-O-P}$=5.0 Hz, C5'), 54.30 (6OCH$_3$), 51.05 (Cα Ala), 50.91 (Cα Ala), 32.34 (C ester), 32.27 (C ester), 26.84 (3×CH$_3$ ester), 26.78 (3×CH$_3$ ester), 21.07 (d, $^3$J$_{C-C-N-P}$=5.0 Hz, CH$_3$ Ala), 21.01 (d, $^3$J$_{C-C-N-P}$=6.3 Hz, CH$_3$ Ala), 20.60 (2'CCH$_3$)

$^{31}$P NMR (202 MHz, MeOH-d$_4$) 13.87

HPLC t$_R$=20.67 min

MS (TOF ES+) m/z: 754.24 (M+NH$^+$, 100%);

HRMS C$_{28}$H$_{48}$N$_7$O$_{10}$P$_1$Br$_1$ calculated: 752.2384. found 752.2379.

Example 25

(2S,2'S)-Neopentyl 2,2'-((((2R,3R,4R,5R)-5-(2-Amino-8-chloro-6-methoxy-9H-purin-9-yl)-3,4-dihydroxy-4-methyltetrahydrofuran-2-yl)methoxy) phosphoryl)bis(azanediyl)dipropanoate was synthesized as follows

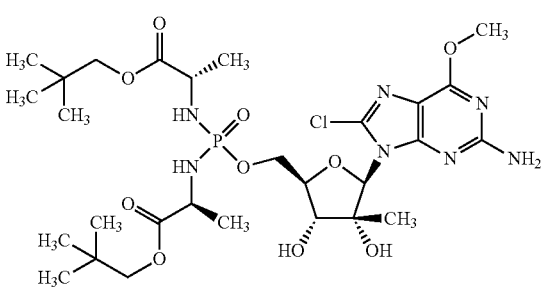 [SMILES: COc1nc(N)nc2c1nc(Cl)n2[C@@H]1O[C@H](COP(=O)(N[C@@H](C)C(=O)OCC(C)(C)C)N[C@@H](C)C(=O)OCC(C)(C)C)[C@@H](O)[C@@]1(C)O]

The general Method B for the synthesis of 5'-phosphorodiamidates was used. A solution of 2-amino-8-chloro-6-methoxy-9-(2-C-methyl-β-D-ribofuranosyl)purine (300 mg, 0.87 mmol) in anhydrous tetrahydrofuran (5 mL) was allowed to react with triethylamine (120 µL, 0.87 mmol) and phosphorus oxychloride (80 µL, 0.87 mmol). Anhydrous dichloromethane (5 mL), and the tosylate salt of 2,2-dimethylpropyl-L-alanine (1.44 g, 4.36 mmol) and triethylamine (1.20 mL, 8.72 mmoles) were added and reaction was stirred overnight. After work-up and silica gel column chromatography, 160 mg of the product was obtained in 26% yield as an off white solid.

The following are the NMR and HPLC results analyzing the synthesized compound:

$^1$H NMR (500 MHz, MeOH-d$_4$) 6.03 (s, 1H, H$_{1'}$), 4.78-4.76 (m, 2H, H$_{3'}$), 4.62-4.57 (m, 1H, H$_{5'a}$), 4.43-4.38 (m, 1H, H$_{5'b}$), 4.23-4.19 (m, 1H, H$_{4'}$), 4.04 (s, 3H, 6OCH$_3$), 3.99-3.93 (m, 1H, Hα Ala), 3.92-3.87 (m, 1H, Hα Ala), 3.79, 3.78, 3.68, 3.61 (2AB, J$_{AB}$=10.5 Hz, 2H, CH$_2$ ester), 1.38 (d, J=7.0 Hz, 3H, CH$_3$ Ala), 1.25 (d, J=7.0 Hz, 3H, CH$_3$ Ala), 1.07 (s, 3H, 2'CCH$_3$), 0.95 (s, 9H, 3×CH$_3$ ester), 0.90 (s, 9H, 3×CH$_3$ ester).

$^{13}$C NMR (126 MHz, MeOH-d$_4$) δ 175.71 (d, $^3$J$_{C-C-N-P}$=6.3 Hz, C=O ester), 175.53 (d, $^3$J$_{C-C-N-P}$=6.3 Hz, C=O ester), 161.78 (C6), 161.48 (C2), 154.66 (C4), 136.71 (C8), 114.40 (C5), 94.63 (C1'), 83.40 (d, $^3$J$_{C-C-O-P}$=6.3 Hz, C4'), 80.22 (C2'), 75.96 (C3'), 75.36, 75.31 (CH$_2$ ester), 67.55 (d, $^2$J$_{C-O-P}$=5.0 Hz, C5'), 54.42 (6OCH$_3$), 51.06 (Cα Ala), 50.91 (Cα Ala), 32.36 (C ester), 32.29 (C ester), 26.88 (3×CH$_3$ ester), 26.82 (3×CH$_3$ ester), 21.15 (d, $^3$J$_{C-C-N-P}$=6.3 Hz, CH$_3$ Ala), 21.08 (d, $^3$J$_{C-C-N-P}$=6.3 Hz, CH$_3$ Ala), 20.61 (2'CCH$_3$)

$^{31}$P NMR (202 MHz, MeOH-d$_4$) 13.87

HPLC t$_R$=20.67 min

Example 26

(2S,2'S)-Dicyclohexyl 2,2'-((((2R,3R,4R,5R)-5-(2-Amino-8-iodo-6-methoxy-9H-purin-9-yl)-3,4-dihydroxy-4-methyltetrahydrofuran-2-yl)methoxy)phosphoryl)bis(azanediyl)dipropanoate was synthesized as follows

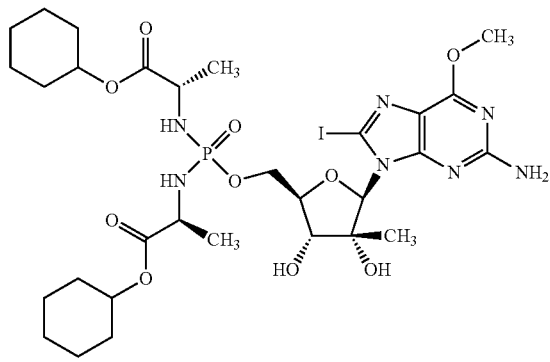 [SMILES: COc1nc(N)nc2c1nc(I)n2[C@@H]1O[C@H](COP(=O)(N[C@@H](C)C(=O)OC2CCCCC2)N[C@@H](C)C(=O)OC2CCCCC2)[C@@H](O)[C@@]1(C)O]

The general Method B for the synthesis of 5'-phosphorodiamidates was used. A solution of 2-amino-8-iodo-6-methoxy-9-(2-C-methyl-β-D-ribofuranosyl)purine (300 mg, 0.69 mmol) in anhyd tetrahydrofuran (5 mL) was allowed to react with triethylamine (96 µL, 0.69 mmol) and phosphorus oxychloride (60 µL, 0.69 mmol). Anhydrous dichloromethane (5 mL), and the HCl salt of cyclohexyl-L-alanine (0.72 g, 3.43 mmol) and triethylamine (0.96 mL, 6.86 mmoles) were added and reaction was stirred overnight. After work-up and silica gel column chromatography, 191 mg of the product was obtained in 34% yield as an off white solid.

The following are the NMR, HPLC and MS results analyzing the synthesized compound:

$^1$H NMR (500 MHz, MeOH-d$_4$) 5.98 (s, 1H, H$_{1'}$), 4.91-82 (m, 2H, H$_{3'}$), 4.72-4.67 (m, 1H, CH ester), 4.63-4.57 (m, 2H, H$_{5'a}$ and CH ester), 4.42-4.38 (m, 1H, H$_{5'b}$), 4.22-4.18 (m, 1H, H$_{4'}$), 4.04 (s, 3H, 6OCH$_3$), 3.87 (q, J=7.0 Hz, 1H, Hα Ala), 3.82 (q, J=7.0 Hz, 1H, Hα Ala), 1.84-1.69 (m, 8H, 4×CH$_2$ ester), 1.41-1.29 (m, 12H, 6×CH$_2$ ester), 1.34 (d, J=7.0 Hz, 3H, CH$_3$ Ala), 1.21 (d, J=7.0 Hz, 3H, CH$_3$ Ala), 1.04 (2s, 3H, 2'CCH$_3$).

$^{13}$C NMR (126 MHz, MeOH-d$_4$) δ 175.23 (d, $^3$J$_{C-C-N-P}$=6.3 Hz, C=O ester), 174.96 (d, $^3$J$_{C-C-N-P}$=6.3 Hz, C=O ester), 161.40 (C6), 161.20 (C2), 154.58 (C4), 119.09 (C5), 99.82 (C8), 97.98 (C1'), 83.39 (d, $^3$J$_{C-C-O-P}$=7.5 Hz, C4'), 80.31 (C2'), 76.05 (C3'), 74.80 (CH ester), 74.69 (CH ester), 67.62 (d, $^2$J$_{C-O-P}$=5.0 Hz, C5'), 54.34 (6OCH$_3$), 51.13 (Cα Ala), 50.94 (Cα Ala), 32.36 (CH$_2$ ester), 32.29 (C ester), 26.87 (3×CH$_3$ ester), 26.80 (3×CH$_3$ ester), 21.07 (CH$_3$ Ala), 21.03 (CH$_3$ Ala), 20.78 (2'CCH$_3$)

$^{31}$P NMR (202 MHz, MeOH-d$_4$) 13.97

HPLC t$_R$=20.91 min

Example 27

((2R,3R,4R,5R)-5-(2-Amino-8-iodo-6-oxo-1H-purin-9(6H)-yl)-3,4-dihydroxy-4-methyltetrahydrofuran-2-yl)methyl phosphate

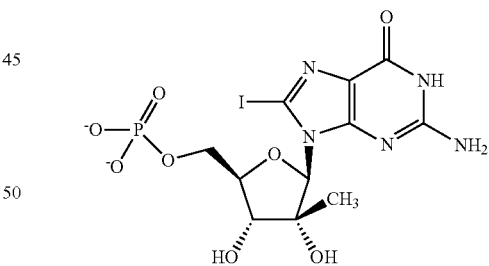

This compound can be synthesized using procedure familiar to one skilled in the art. For example: 2-Amino-9((2R,3R,4R,5R)-3,4-dihydroxy-5-(hydroxymethyl)-3-methyltetrahydrofuran-2-yl)-8-iodo-1H-purin-6(9H)-one is dissolved in anhydrous trimethylphosphate (20 mg/mL) and 1.5 equiv of anhydrous 2,4,6-collidine is added. The solution is stirred and warmed to ensure dissolution of the starting nucleoside. The solution is then cooled to −5° C. to 0° C. under a nitrogen atmosphere and phosphorous oxychloride (2 equiv) is added. The reaction is stirred at ~0° C. for 2 h, and is quenched with aqueous triethylammonium bicarbonate and is purified by preparative HPLC.

Example 28

((2R,3R,4R,5R)-5-(2-Amino-8-iodo-6-oxo-1H-purin-9(6H)-yl)-3,4-dihydroxy-4-methyltetrahydrofuran-2-yl)methyl triphosphate

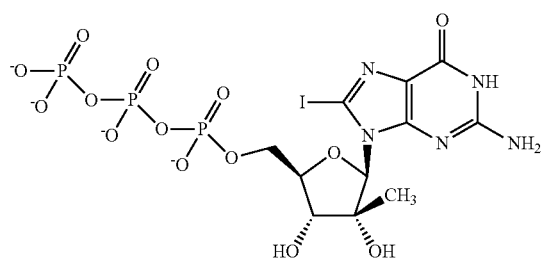

This compound can be synthesized using procedure familiar to one skilled in the art. For example: 2-Amino-9-((2R,3R,4R,5R)-3,4-dihydroxy-5-(hydroxymethyl)-3-methyltetrahydrofuran-2-yl)-8-iodo-1H-purin-6(9H)-one is dissolved in anhydrous trimethylphosphate (20 mg/mL) and 1.5 equiv of anhydrous 2,4,6-collidine is added. The solution is stirred and warmed to ensure dissolution of the starting nucleoside. The solution is then cooled to −5° C. to 0° C. under a nitrogen atmosphere and phosphorous oxychloride (2 equiv) is added. The reaction is stirred at ~0° C. for 2 h. 2.0 M pyrophosphate in DMF is added along with 4 equiv of anhydrous tributylamine. This solution is stirred for 1 h then 0.5M triethylammonium bicarbonate is added. This solution is stirred for 30 min then the reaction mixture is evaporated to dryness. The compound is purified by preparative HPLC.

Example 29

(S)-2-((((2R,3R,4R,5R)-5-(2-Amino-8-iodo-6-methoxy-9H-purin-9-yl)-3,4-dihydroxy-4-methyltetrahydrofuran-2-yl)methoxy)oxidophosphorylamino)propanoate

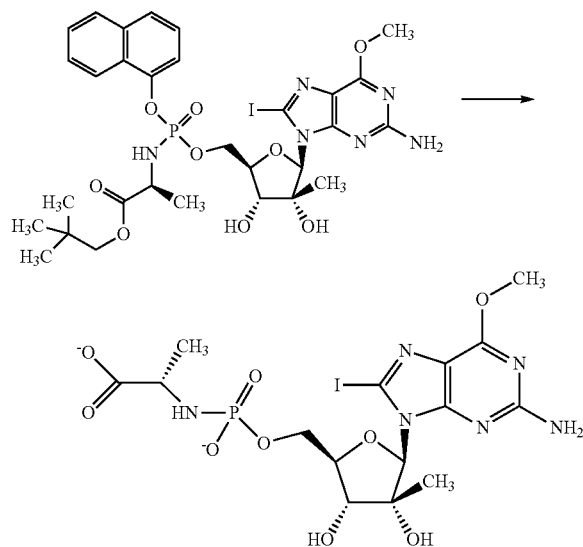

This compound can be synthesized by procedures familiar to one skilled in the art. For example: (2S)-neopentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate is dissolved in an solution of Trizma (or TRIS) buffer and acetone (2:1). Carboxypeptidase Y is added and the solution is incubated at 37° C. for 15 h. The solution is concentrated and purified by preparative HPLC Further to the above Examples, representative compounds, prepared according to the examples were tested for potency in an HCV replicon assay (Genotype 1b) for activity against the virus ($EC_{50}$) and toxicity to the cells ($CC_{50}$). These results are set forth below.

Huh7 Replicon Cell Lines and Cell Culture Conditions:

A luciferase-reporter genotype 1b subgenomic replicon cell line, and a genotype 1a full-length replicon cell line were obtained from Apath, LLC, Brooklyn, N.Y.: All cell lines were passaged twice a week by splitting 4 or 6 fold. Cells were maintained in DMEM-high glucose medium (HyClone, Logan, Utah) supplemented with 9% FBS (HyClone), 2 mM glutamine (Invitrogen, Carlsbad, Calif.), 100 U/mL PenStrep (Invitrogen). Media also contained 0.25 mg/mL of the antibiotic G-418 to maintain stable expression of the replicon (Invitrogen). Incubation was performed at 37° C. in 5% $CO_2$ atmosphere. Replicon cell lines were used until they accumulated 15-to-18 passages, after which cells were restarted from the frozen stock. Seeding cell counts were routinely determined using an automatic Cedex HiRes cell counter (Flownomics Analytical Instruments, Madison, Wis.) or manually using INCYTO C—Chip™ Disposable Hemacytometers (Fisher Scientific, Pittsburgh, Pa.).

The anti-HCV assays were done accordingly:

Luciferase Genotype 1b Replicon Potency Assay.

Replicon cells were seeded into white 96-well plates (Nunc/VWR) at a density of $2 \times 10^4$ cells/well in medium without G-418. A Stacker Multidrop Liquid Dispenser (MTX Lab Systems, Vienna, Va.) was employed to ensure uniform and fast cell seeding into multiple plates. 18-24 h after cell plating, inhibitors were added and cells were incubated for additional 24, 48, or 72 h (as indicated). Compounds were tested in triplicates and quadruplicates at 3× or 4× serial dilutions over a range of 0.0001-to-10 μM concentrations. HCV replication was monitored by Renilla luciferase reporter activity assay using Renilla luciferase reporter (Promega, Madison, Wis.) and a Veritas Luminometer (Turner Biosystems, Sunnyvale, Calif.). 50% and 90% inhibitory concentration ($IC_{50}$ and $IC_{90}$) values were calculated as the concentration of compound that results correspondingly in 50% and 90% decreases in the reporter expression as compared to untreated cells. The values were determined by non-linear regression (four-parameter sigmoidal curve fitting) analysis.

The cell cytotoxicity assay data was obtained as described below:

Cytotoxicity Assay.

Cells were seeded into 96-well plates at a density of $2 \times 10^4$ cells per well. 24 h after cell plating, 11 serial 2× compound dilutions, starting with 100 μM, were applied to the testing plates (3 repeats per compound dilution). Each testing plate was run with a "no-compound" control. Incubation with compounds was continued at 37° C. in a $CO_2$ incubator for 72 h. To determine cell viability, the CellTiter-Glo® assay (Promega, Madison, Wis.) was performed according to the manufacturer's protocol. The compound concentration resulting in 50% luminescent signal was reported as the $CC_{50}$ concentration.

The results of the assay in terms of IC$_{50}$ (μM) and CC$_{50}$ (μM) are given in Table 1 below:

TABLE 1

| Example No. | Structure | IC$_{50}$ μM | CC$_{50}$ μM |
|---|---|---|---|
| 3 | 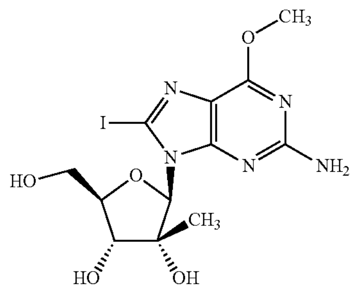 [SMILES: COc1nc(N)nc2c1nc(I)n2[C@@H]1O[C@H](CO)[C@@H](O)[C@@]1(C)O] | 6.1 | >100 |
| 4 | 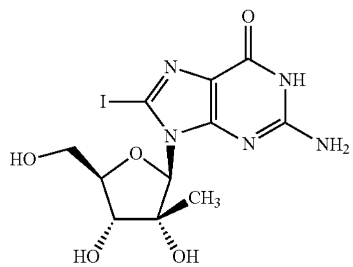 [SMILES: C[C@@]1(O)[C@H](O)[C@@H](CO)O[C@H]1n1c(I)nc2c(=O)[nH]c(N)nc21] | | |
| 5 | 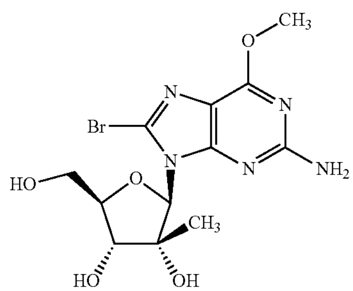 [SMILES: COc1nc(N)nc2c1nc(Br)n2[C@@H]1O[C@H](CO)[C@@H](O)[C@@]1(C)O] | >100 | >100 |
| 6 | 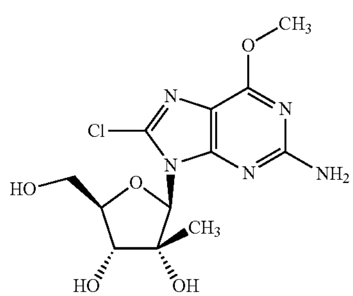 [SMILES: COc1nc(N)nc2c1nc(Cl)n2[C@@H]1O[C@H](CO)[C@@H](O)[C@@]1(C)O] | >100 | >100 |
| 7 | 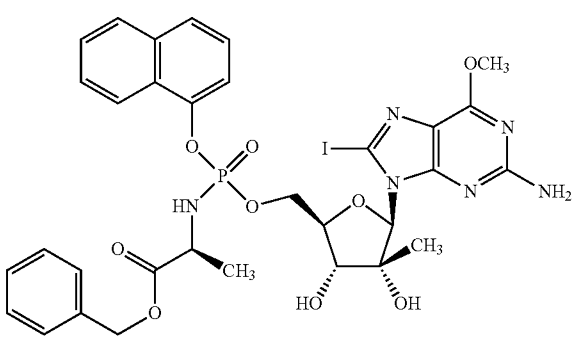 [SMILES: COc1nc(N)nc2c1nc(I)n2[C@@H]1O[C@H](COP(=O)(N[C@@H](C)C(=O)OCc2ccccc2)Oc2cccc3ccccc23)[C@@H](O)[C@@]1(C)O] | 0.031 | 18 |

TABLE 1-continued

| Example No. | Structure | IC$_{50}$ μM | CC$_{50}$ μM |
|---|---|---|---|
| 8 | 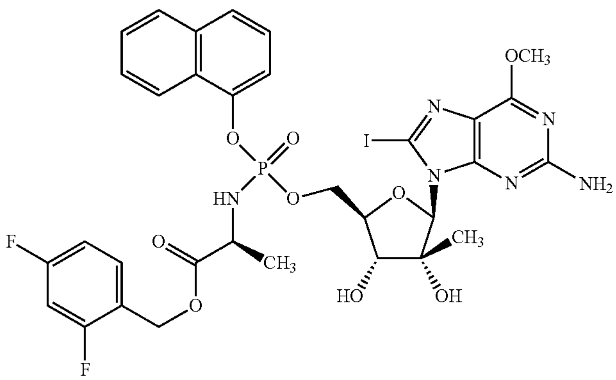 [SMILES: COc1nc(N)nc2c1nc(I)n2[C@@H]1O[C@H](COP(=O)(N[C@@H](C)C(=O)OCc2ccc(F)cc2F)Oc2cccc3ccccc23)[C@@H](O)[C@@]1(C)O] | 0.009 | 8.1 |
| 9 | 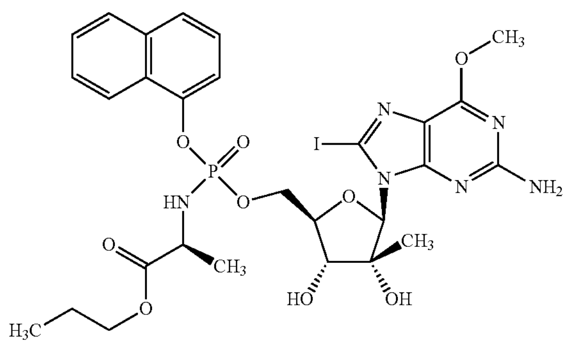 [SMILES: CCCOC(=O)[C@H](C)NP(=O)(OC[C@H]1O[C@@H](n2c(I)nc3c(OC)nc(N)nc32)[C@](C)(O)[C@@H]1O)Oc1cccc2ccccc12] | .009 | 6 |
| 10 | 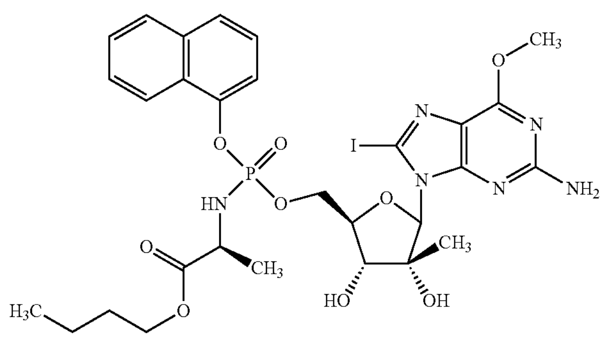 [SMILES: CCCCOC(=O)[C@H](C)NP(=O)(OC[C@H]1OC(n2c(I)nc3c(OC)nc(N)nc32)[C@](C)(O)[C@@H]1O)Oc1cccc2ccccc12] | 0.011 | 7.9 |
| 11 | 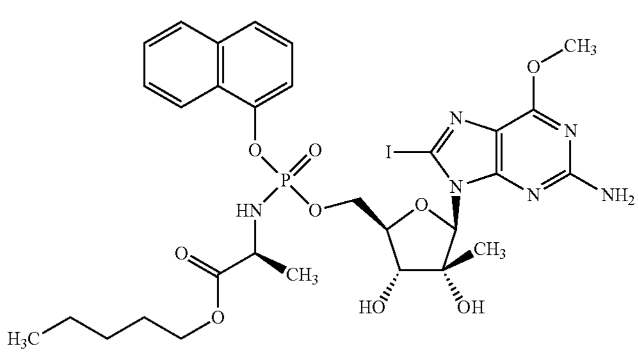 [SMILES: CCCCCOC(=O)[C@H](C)NP(=O)(OC[C@H]1O[C@@H](n2c(I)nc3c(OC)nc(N)nc32)[C@](C)(O)[C@@H]1O)Oc1cccc2ccccc12] | 0.012 | 11 |

TABLE 1-continued

| Example No. | Structure | IC$_{50}$ μM | CC$_{50}$ μM |
|---|---|---|---|
| 12 | 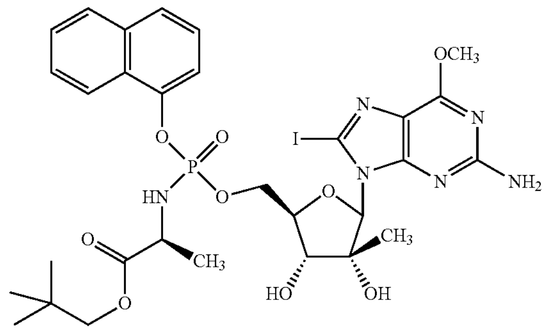 [SMILES: COc1nc(N)nc2c1nc(I)n2C1O[C@H](COP(=O)(N[C@@H](C)C(=O)OCC(C)(C)C)Oc2cccc3ccccc23)[C@@H](O)[C@@]1(C)O] | 0.02 | 14 |
| 13 | 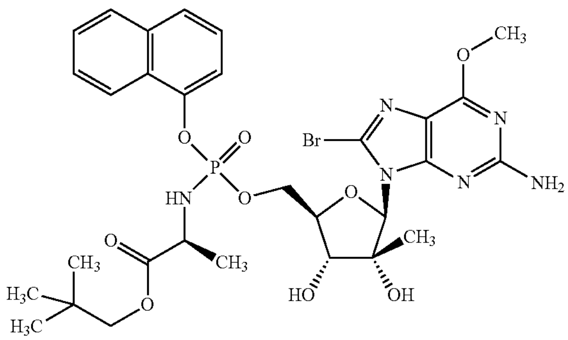 | 15 | 60 |
| 14 | 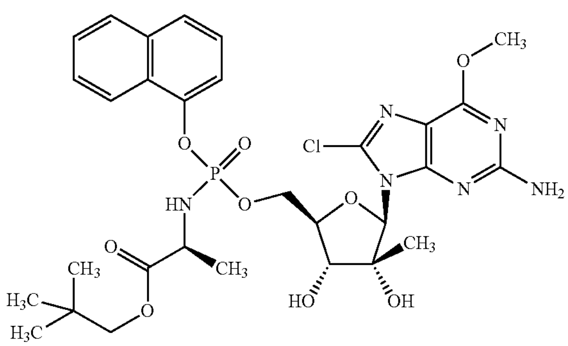 [SMILES: COc1nc(N)nc2c1nc(Cl)n2[C@@H]1O[C@H](COP(=O)(N[C@@H](C)C(=O)OCC(C)(C)C)Oc2cccc3ccccc23)[C@@H](O)[C@@]1(C)O] | >10 | 60 |
| 15 | 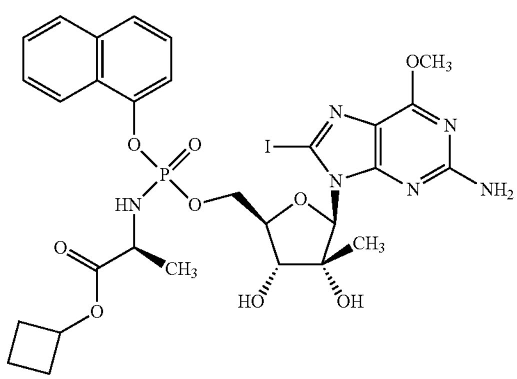 [SMILES: COc1nc(N)nc2c1nc(I)n2[C@@H]1O[C@H](COP(=O)(N[C@@H](C)C(=O)OC2CCC2)Oc2cccc3ccccc23)[C@@H](O)[C@@]1(C)O] | 0.010 | 6.8 |

TABLE 1-continued

| Example No. | Structure | IC$_{50}$ μM | CC$_{50}$ μM |
|---|---|---|---|
| 16 | 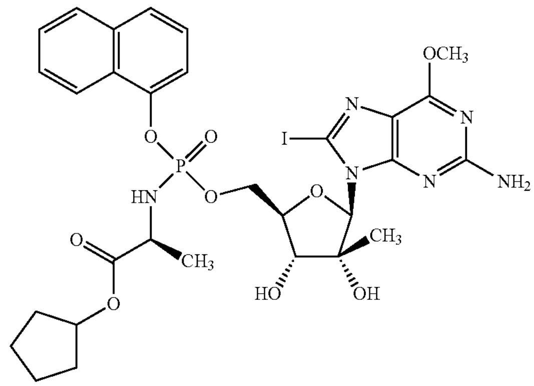 [SMILES: COc1nc(N)nc2c1nc(I)n2[C@@H]1O[C@H](COP(=O)(N[C@@H](C)C(=O)OC2CCCC2)Oc2cccc3ccccc23)[C@@H](O)[C@@]1(C)O] | 0.012 | 13 |
| 17 | 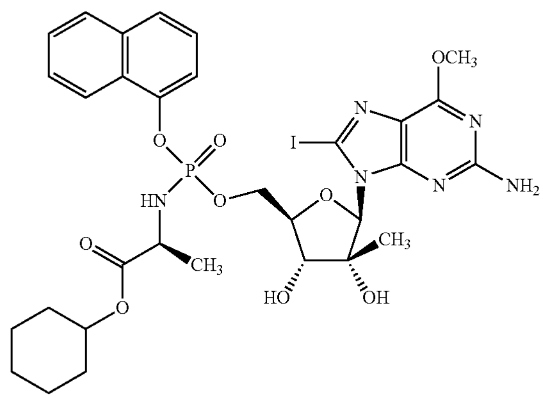 [SMILES: COc1nc(N)nc2c1nc(I)n2[C@@H]1O[C@H](COP(=O)(N[C@@H](C)C(=O)OC2CCCCC2)Oc2cccc3ccccc23)[C@@H](O)[C@@]1(C)O] | 0.016 | 11 |
| 18 | 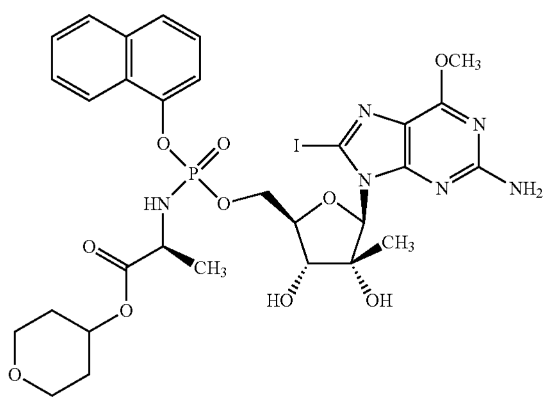 [SMILES: COc1nc(N)nc2c1nc(I)n2[C@@H]1O[C@H](COP(=O)(N[C@@H](C)C(=O)OC2CCOCC2)Oc2cccc3ccccc23)[C@@H](O)[C@@]1(C)O] | 0.018 | 26 |
| 19 | 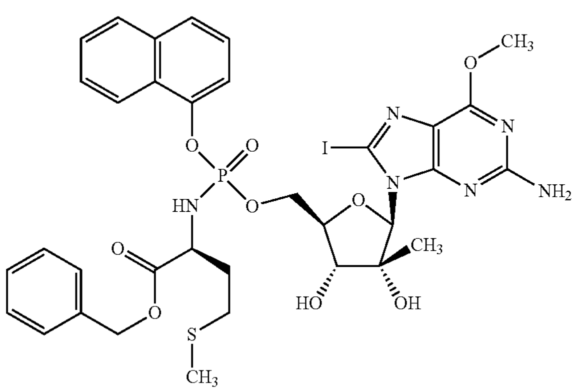 [SMILES: COc1nc(N)nc2c1nc(I)n2[C@@H]1O[C@H](COP(=O)(N[C@@H](CCSC)C(=O)OCc2ccccc2)Oc2cccc3ccccc23)[C@@H](O)[C@@]1(C)O] | 0.034 | 29 |

TABLE 1-continued

| Example No. | Structure | IC$_{50}$ μM | CC$_{50}$ μM |
|---|---|---|---|
| 20 | 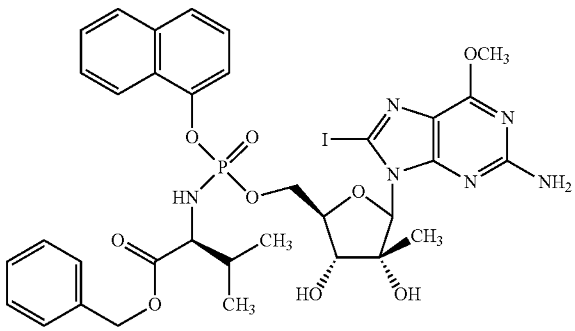 [SMILES: COc1nc(N)nc2c1nc(I)n2C1O[C@H](COP(=O)(N[C@H](C(=O)OCc2ccccc2)C(C)C)Oc2cccc3ccccc23)[C@@H](O)[C@@]1(C)O] | 0.14 | 25 |
| 21 | 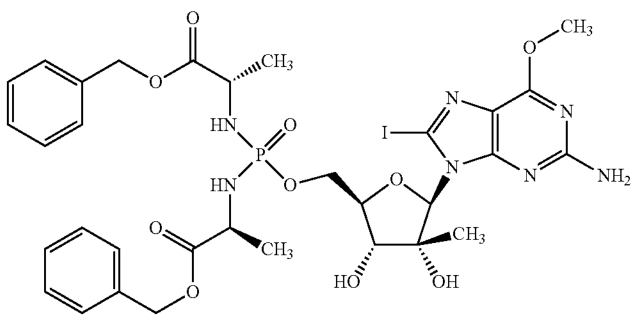 [SMILES: COc1nc(N)nc2c1nc(I)n2[C@@H]1O[C@H](COP(=O)(N[C@@H](C)C(=O)OCc2ccccc2)N[C@@H](C)C(=O)OCc2ccccc2)[C@@H](O)[C@@]1(C)O] | 0.046 | 22 |
| 22 | 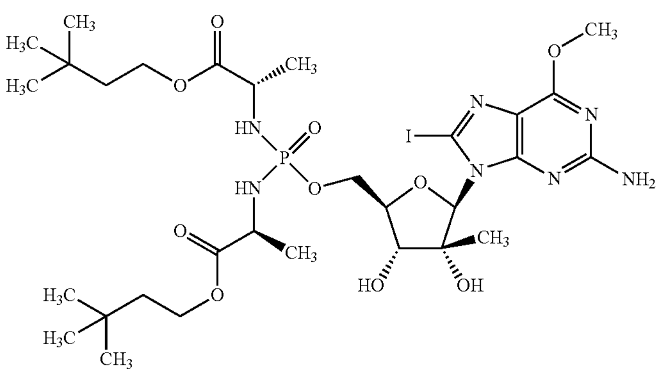 [SMILES: COc1nc(N)nc2c1nc(I)n2[C@@H]1O[C@H](COP(=O)(N[C@@H](C)C(=O)OCCC(C)(C)C)N[C@@H](C)C(=O)OCCC(C)(C)C)[C@@H](O)[C@@]1(C)O] | 0.072 | 11 |
| 23 | 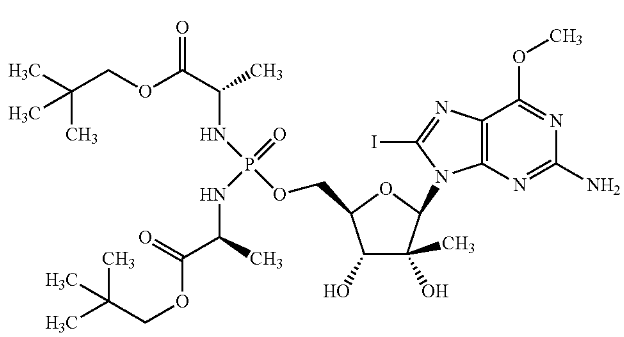 [SMILES: COc1nc(N)nc2c1nc(I)n2[C@@H]1O[C@H](COP(=O)(N[C@@H](C)C(=O)OCC(C)(C)C)N[C@@H](C)C(=O)OCC(C)(C)C)[C@@H](O)[C@@]1(C)O] | 0.11 | 53 |

TABLE 1-continued

| Example No. | Structure | IC$_{50}$ μM | CC$_{50}$ μM |
|---|---|---|---|
| 24 | 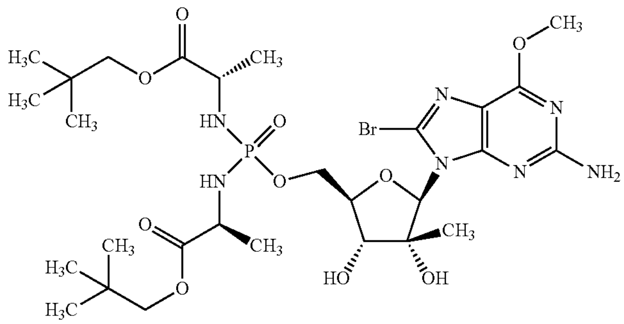 [SMILES: COc1nc(N)nc2c1nc(Br)n2[C@@H]1O[C@H](COP(=O)(N[C@@H](C)C(=O)OCC(C)(C)C)N[C@@H](C)C(=O)OCC(C)(C)C)[C@@H](O)[C@@]1(C)O] | >40 | >100 |
| 25 | 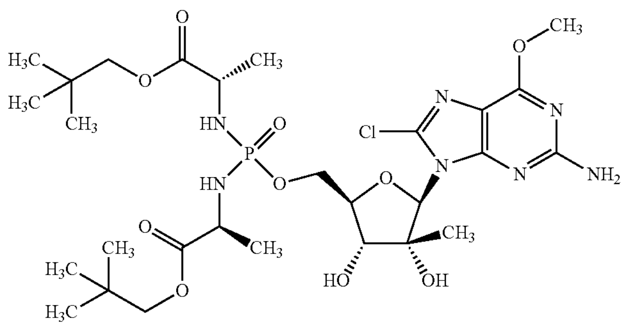 [SMILES: COc1nc(N)nc2c1nc(Cl)n2[C@@H]1O[C@H](COP(=O)(N[C@@H](C)C(=O)OCC(C)(C)C)N[C@@H](C)C(=O)OCC(C)(C)C)[C@@H](O)[C@@]1(C)O] | 10 | >100 |
| 26 | 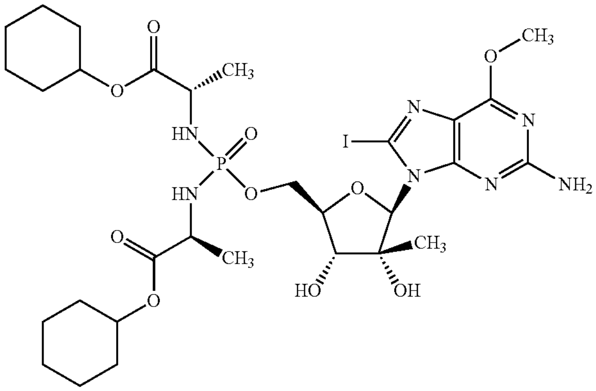 [SMILES: COc1nc(N)nc2c1nc(I)n2[C@@H]1O[C@H](COP(=O)(N[C@@H](C)C(=O)OC2CCCCC2)N[C@@H](C)C(=O)OC2CCCCC2)[C@@H](O)[C@@]1(C)O] | 0.13 | 54 |
| 27 | 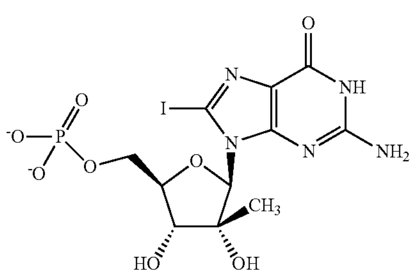 [SMILES: C[C@@]1(O)[C@H](O)[C@@H](COP(=O)([O-])[O-])O[C@H]1n1c(I)nc2c(=O)[nH]c(N)nc21] | | |
| 28 | 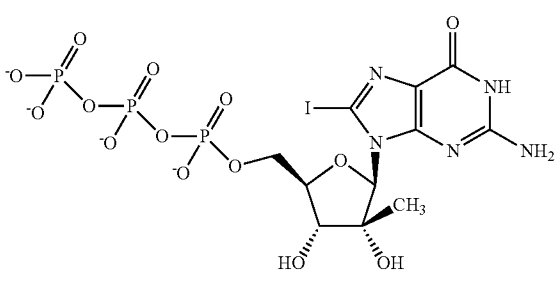 | | |

TABLE 1-continued

| Example No. | Structure | IC$_{50}$ μM | CC$_{50}$ μM |
|---|---|---|---|
| 29 | 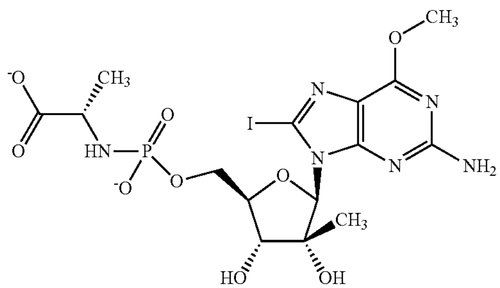 [SMILES: COc1nc(N)nc2c1nc(I)n2[C@@H]1O[C@H](COP(=O)([O-])N[C@@H](C)C(=O)[O-])[C@@H](O)[C@@]1(C)O] | | |
| 30 | 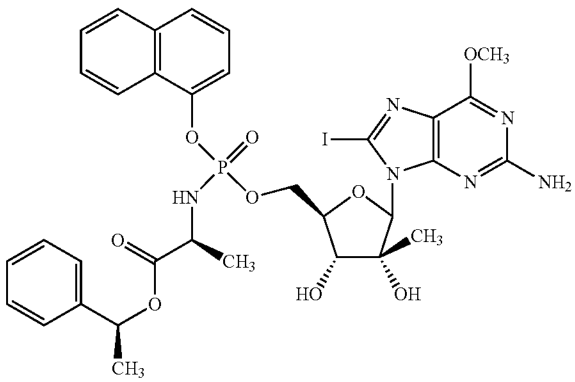 [SMILES: COc1nc(N)nc2c1nc(I)n2C1O[C@H](COP(=O)(N[C@@H](C)C(=O)O[C@@H](C)c2ccccc2)Oc2cccc3ccccc23)[C@@H](O)[C@@]1(C)O] | | |
| 31 | 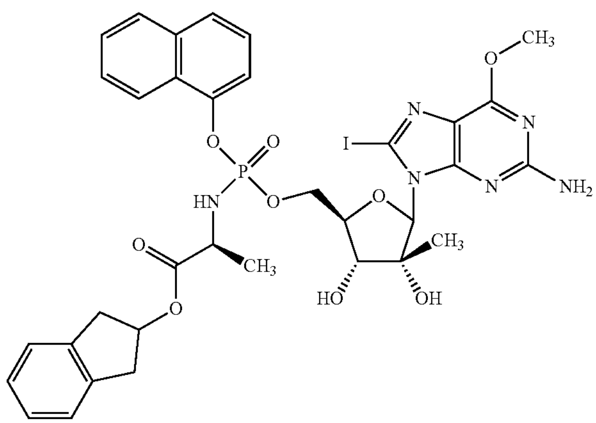 [SMILES: COc1nc(N)nc2c1nc(I)n2C1O[C@H](COP(=O)(N[C@@H](C)C(=O)OC2Cc3ccccc3C2)Oc2cccc3ccccc23)[C@@H](O)[C@@]1(C)O] | | |
| 32 | 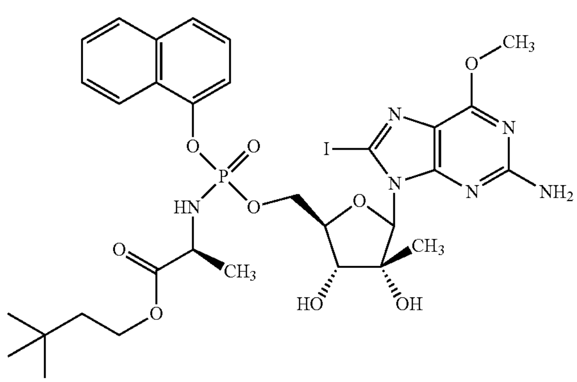 [SMILES: COc1nc(N)nc2c1nc(I)n2C1O[C@H](COP(=O)(N[C@@H](C)C(=O)OCCC(C)(C)C)Oc2cccc3ccccc23)[C@@H](O)[C@@]1(C)O] | | |

TABLE 1-continued

| Example No. | Structure | IC₅₀ μM | CC₅₀ μM |
|---|---|---|---|
| 33 | 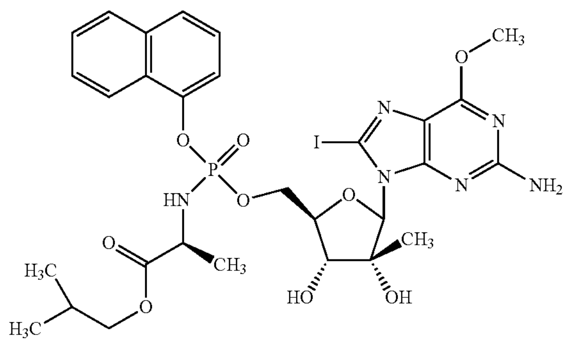 [SMILES: COc1nc(N)nc2c1nc(I)n2C1O[C@H](COP(=O)(N[C@@H](C)C(=O)OCC(C)C)Oc2cccc3ccccc23)[C@@H](O)[C@@]1(C)O] | | |
| 34 | 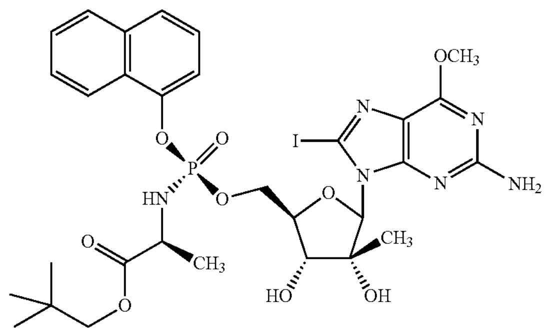 [SMILES: COc1nc(N)nc2c1nc(I)n2C1O[C@H](CO[P@@](=O)(N[C@@H](C)C(=O)OCC(C)(C)C)Oc2cccc3ccccc23)[C@@H](O)[C@@]1(C)O] | | |
| 35 | 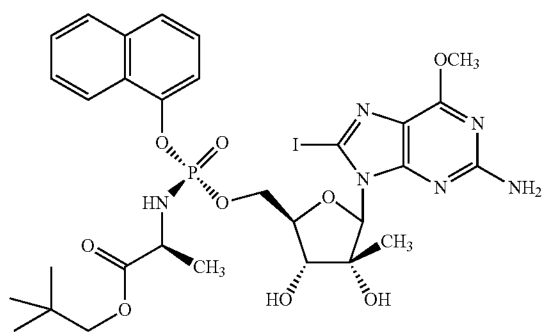 [SMILES: COc1nc(N)nc2c1nc(I)n2C1O[C@H](CO[P@](=O)(N[C@@H](C)C(=O)OCC(C)(C)C)Oc2cccc3ccccc23)[C@@H](O)[C@@]1(C)O] | | |
| 36 | 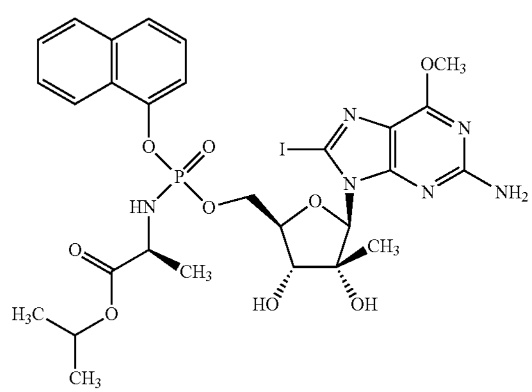 [SMILES: COc1nc(N)nc2c1nc(I)n2[C@@H]1O[C@H](COP(=O)(N[C@@H](C)C(=O)OC(C)C)Oc2cccc3ccccc23)[C@@H](O)[C@@]1(C)O] | | |

TABLE 1-continued

| Example No. | Structure | IC₅₀ μM | CC₅₀ μM |
|---|---|---|---|
| 37 | 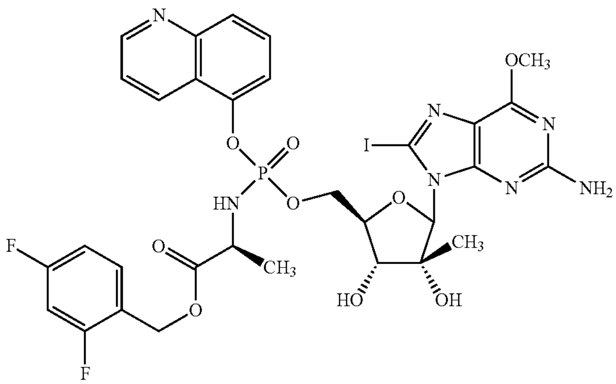 [SMILES: COc1nc(N)nc2c1nc(I)n2C1O[C@H](COP(=O)(N[C@@H](C)C(=O)OCc2ccc(F)cc2F)Oc2cccc3ncccc23)[C@@H](O)[C@@]1(C)O] | | |
| 38 | 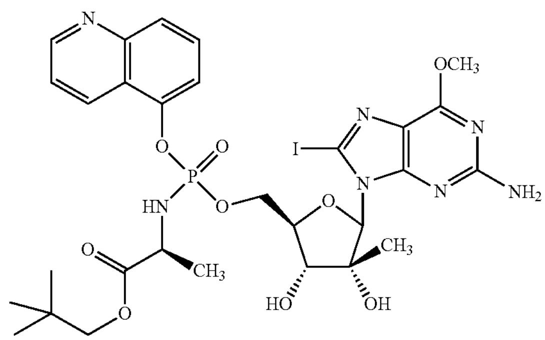 [SMILES: COc1nc(N)nc2c1nc(I)n2C1O[C@H](COP(=O)(N[C@@H](C)C(=O)OCC(C)(C)C)Oc2cccc3ncccc23)[C@@H](O)[C@@]1(C)O] | | |
| 39 | 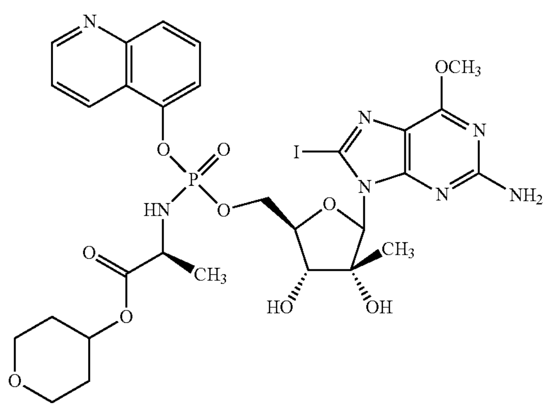 [SMILES: COc1nc(N)nc2c1nc(I)n2C1O[C@H](COP(=O)(N[C@@H](C)C(=O)OC2CCOCC2)Oc2cccc3ncccc23)[C@@H](O)[C@@]1(C)O] | | |
| 40 | 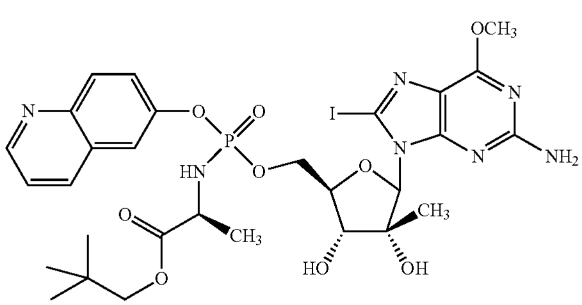 [SMILES: COc1nc(N)nc2c1nc(I)n2C1O[C@H](COP(=O)(N[C@@H](C)C(=O)OCC(C)(C)C)Oc2ccc3ncccc3c2)[C@@H](O)[C@@]1(C)O] | | |

TABLE 1-continued

| Example No. | Structure | IC$_{50}$ μM | CC$_{50}$ μM |
|---|---|---|---|
| 41 | 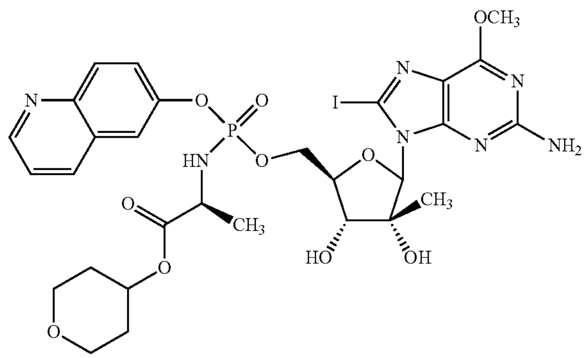 [SMILES: COc1nc(N)nc2c1nc(I)n2C1O[C@H](COP(=O)(N[C@@H](C)C(=O)OC2CCOCC2)Oc2ccc3ncccc3c2)[C@@H](O)[C@@]1(C)O] | | |
| 42 | 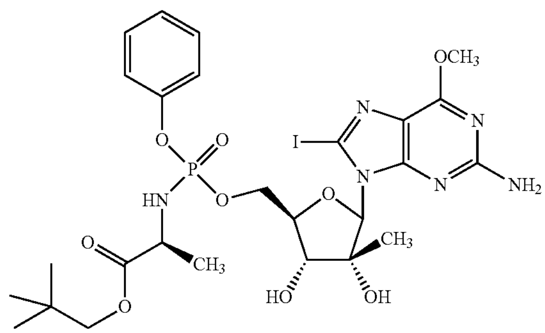 [SMILES: COc1nc(N)nc2c1nc(I)n2C1O[C@H](COP(=O)(N[C@@H](C)C(=O)OCC(C)(C)C)Oc2ccccc2)[C@@H](O)[C@@]1(C)O] | | |
| 43 | 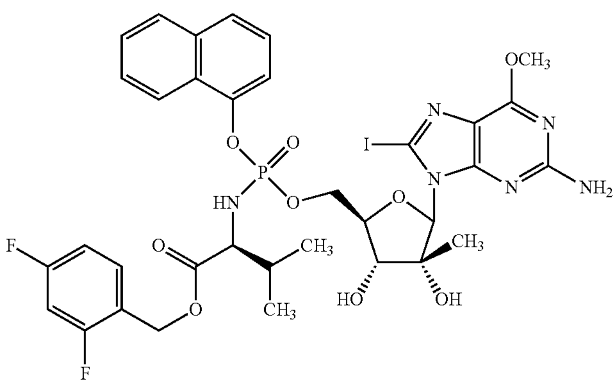 [SMILES: COc1nc(N)nc2c1nc(I)n2C1O[C@H](COP(=O)(N[C@H](C(=O)OCc2ccc(F)cc2F)C(C)C)Oc2cccc3ccccc23)[C@@H](O)[C@@]1(C)O] | | |
| 44 | 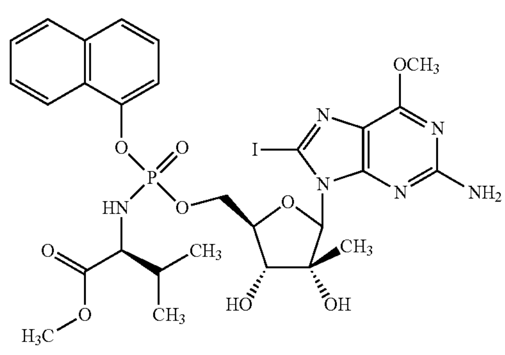 [SMILES: COC(=O)[C@@H](NP(=O)(OC[C@H]1OC(n2c(I)nc3c(OC)nc(N)nc32)[C@](C)(O)[C@@H]1O)Oc1cccc2ccccc12)C(C)C] | | |

TABLE 1-continued
| Example No. | Structure | IC$_{50}$ μM | CC$_{50}$ μM |
|---|---|---|---|
| 45 | 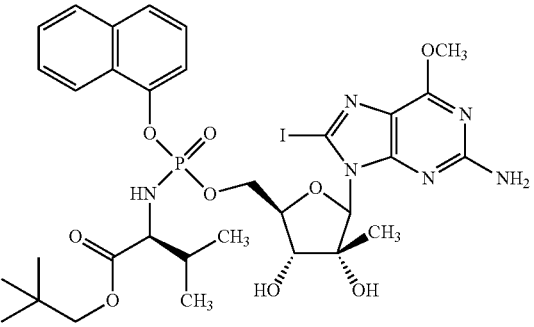 [SMILES: COc1nc(N)nc2c1nc(I)n2C1O[C@H](COP(=O)(N[C@H](C(=O)OCC(C)(C)C)C(C)C)Oc2cccc3ccccc23)[C@@H](O)[C@@]1(C)O] | | |
| 46 | 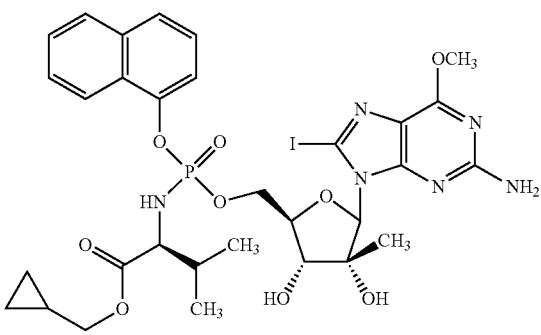 [SMILES: COc1nc(N)nc2c1nc(I)n2C1O[C@H](COP(=O)(N[C@H](C(=O)OCC2CC2)C(C)C)Oc2cccc3ccccc23)[C@@H](O)[C@@]1(C)O] | | |
| 47 | 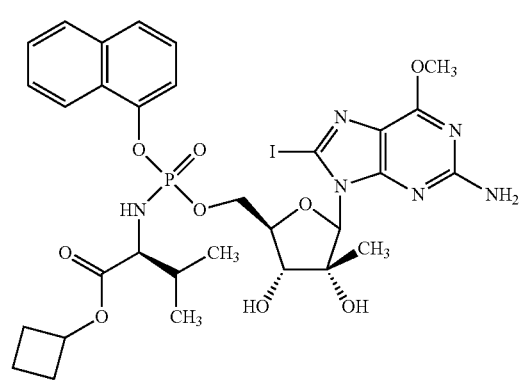 [SMILES: COc1nc(N)nc2c1nc(I)n2C1O[C@H](COP(=O)(N[C@H](C(=O)OC2CCC2)C(C)C)Oc2cccc3ccccc23)[C@@H](O)[C@@]1(C)O] | | |
| 48 | 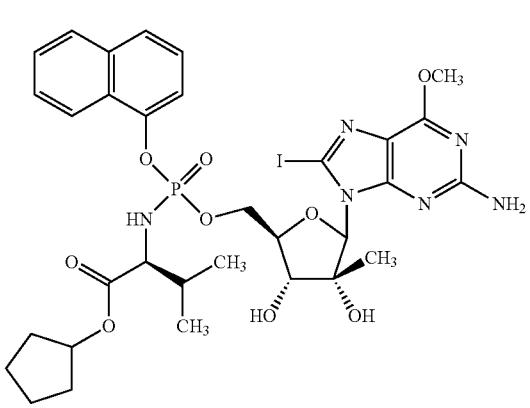 [SMILES: COc1nc(N)nc2c1nc(I)n2C1O[C@H](COP(=O)(N[C@H](C(=O)OC2CCCC2)C(C)C)Oc2cccc3ccccc23)[C@@H](O)[C@@]1(C)O] | | |

TABLE 1-continued
| Example No. | Structure | IC$_{50}$ μM | CC$_{50}$ μM |
|---|---|---|---|
| 49 | 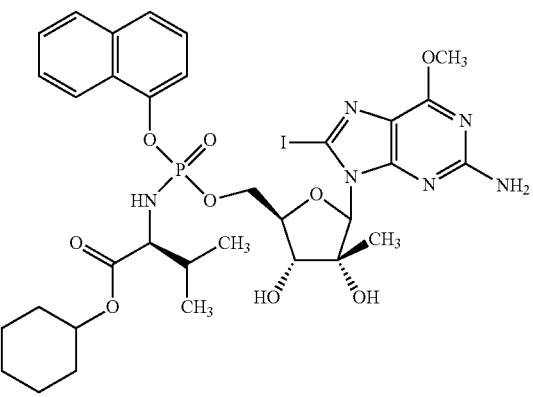 [SMILES: COc1nc(N)nc2c1nc(I)n2C1O[C@H](COP(=O)(N[C@H](C(=O)OC2CCCCC2)C(C)C)Oc2cccc3ccccc23)[C@@H](O)[C@@]1(C)O] | | |
| 50 | 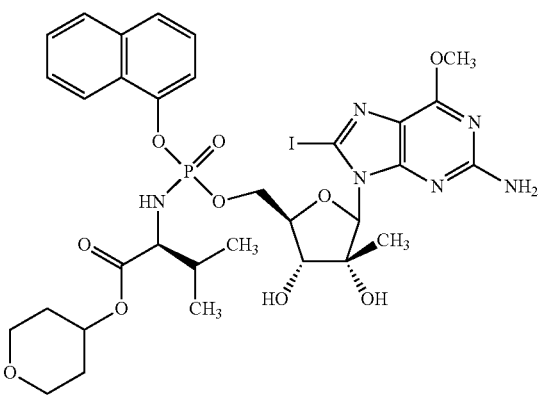 [SMILES: COc1nc(N)nc2c1nc(I)n2C1O[C@H](COP(=O)(N[C@H](C(=O)OC2CCOCC2)C(C)C)Oc2cccc3ccccc23)[C@@H](O)[C@@]1(C)O] | | |
| 51 | 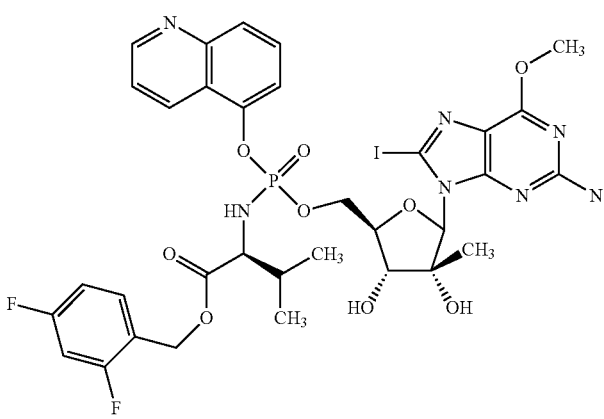 | | |
| 52 | 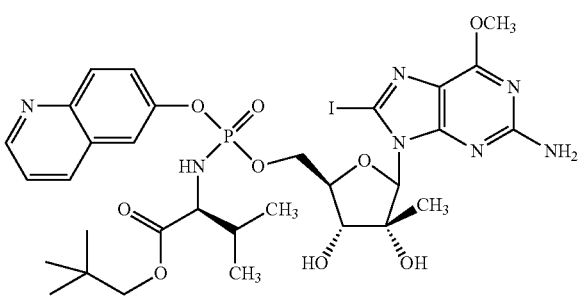 [SMILES: COc1nc(N)nc2c1nc(I)n2C1O[C@H](COP(=O)(N[C@H](C(=O)OCC(C)(C)C)C(C)C)Oc2ccc3ncccc3c2)[C@@H](O)[C@@]1(C)O] | | |

TABLE 1-continued

| Example No. | Structure | IC$_{50}$ μM | CC$_{50}$ μM |
|---|---|---|---|
| 53 | 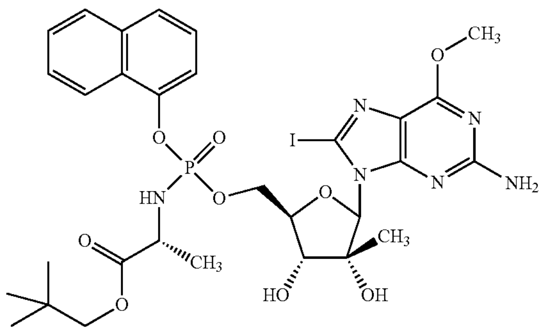 [SMILES: COc1nc(N)nc2c1nc(I)n2C1O[C@H](COP(=O)(N[C@H](C)C(=O)OCC(C)(C)C)Oc2cccc3ccccc23)[C@@H](O)[C@@]1(C)O] | | |
| 54 | 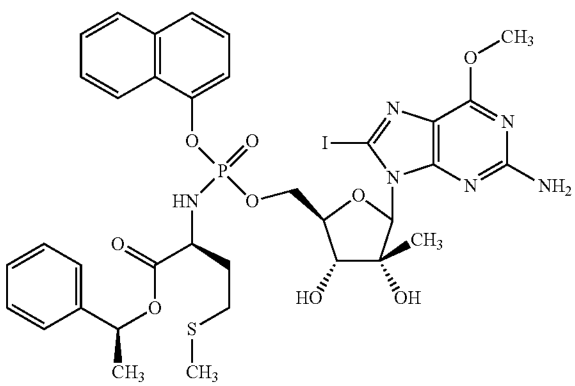 [SMILES: COc1nc(N)nc2c1nc(I)n2C1O[C@H](COP(=O)(N[C@@H](CCSC)C(=O)O[C@@H](C)c2ccccc2)Oc2cccc3ccccc23)[C@@H](O)[C@@]1(C)O] | | |
| 55 | 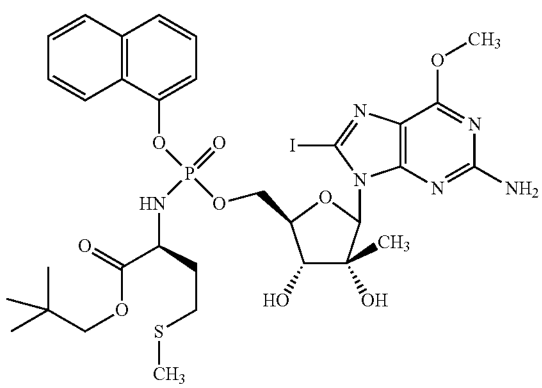 [SMILES: COc1nc(N)nc2c1nc(I)n2C1O[C@H](COP(=O)(N[C@@H](CCSC)C(=O)OCC(C)(C)C)Oc2cccc3ccccc23)[C@@H](O)[C@@]1(C)O] | | |
| 56 | 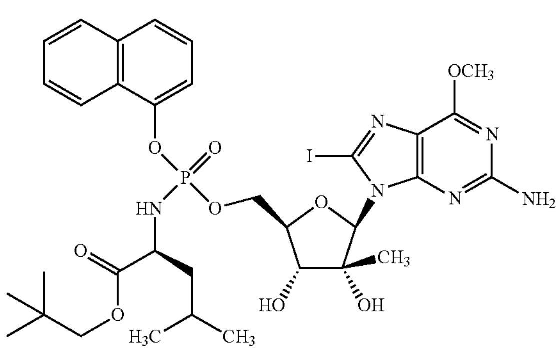 [SMILES: COc1nc(N)nc2c1nc(I)n2[C@@H]1O[C@H](COP(=O)(N[C@@H](CC(C)C)C(=O)OCC(C)(C)C)Oc2cccc3ccccc23)[C@@H](O)[C@@]1(C)O] | | |

TABLE 1-continued

| Example No. | Structure | IC$_{50}$ μM | CC$_{50}$ μM |
|---|---|---|---|
| 57 | 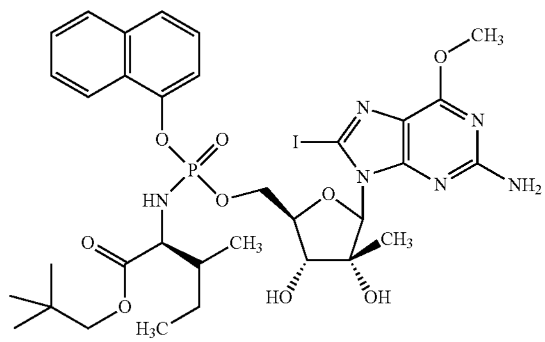 [SMILES: CCC(C)[C@H](NP(=O)(OC[C@H]1OC(n2c(I)nc3c(OC)nc(N)nc32)[C@](C)(O)[C@@H]1O)Oc1cccc2ccccc12)C(=O)OCC(C)(C)C] | | |
| 58 | 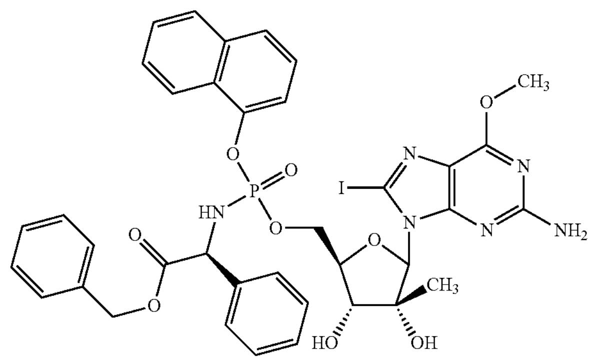 [SMILES: COc1nc(N)nc2c1nc(I)n2C1O[C@H](COP(=O)(N[C@H](C(=O)OCc2ccccc2)c2ccccc2)Oc2cccc3ccccc23)[C@@H](O)[C@@]1(C)O] | | |
| 59 | 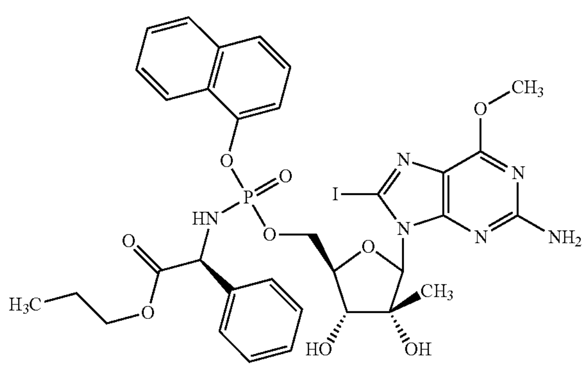 [SMILES: CCCOC(=O)[C@@H](NP(=O)(OC[C@H]1OC(n2c(I)nc3c(OC)nc(N)nc32)[C@](C)(O)[C@@H]1O)Oc1cccc2ccccc12)c1ccccc1] | | |
| 60 | 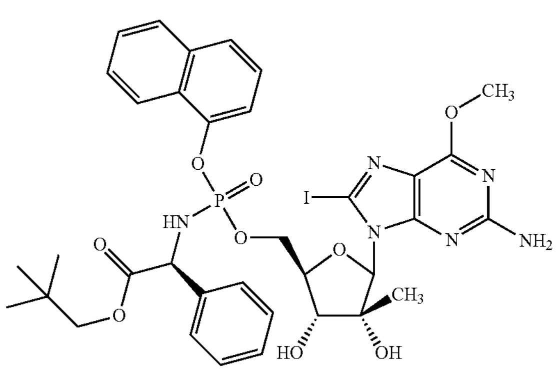 [SMILES: COc1nc(N)nc2c1nc(I)n2C1O[C@H](COP(=O)(N[C@H](C(=O)OCC(C)(C)C)c2ccccc2)Oc2cccc3ccccc23)[C@@H](O)[C@@]1(C)O] | | |

TABLE 1-continued

| Example No. | Structure | IC$_{50}$ μM | CC$_{50}$ μM |
|---|---|---|---|
| 61 | 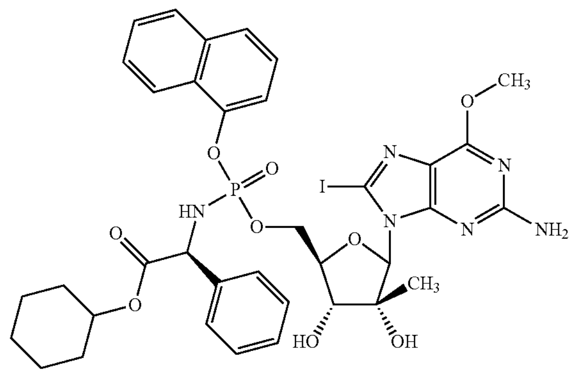 [SMILES: COc1nc(N)nc2c1nc(I)n2C1O[C@H](COP(=O)(N[C@H](C(=O)OC2CCCCC2)c2ccccc2)Oc2cccc3ccccc23)[C@@H](O)[C@@]1(C)O] | | |
| 62 | 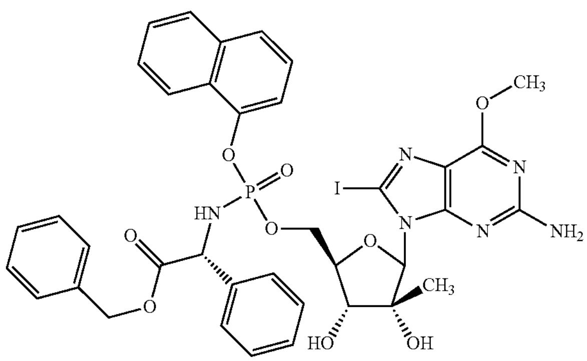 [SMILES: COc1nc(N)nc2c1nc(I)n2C1O[C@H](COP(=O)(N[C@@H](C(=O)OCc2ccccc2)c2ccccc2)Oc2cccc3ccccc23)[C@@H](O)[C@@]1(C)O] | | |
| 63 | 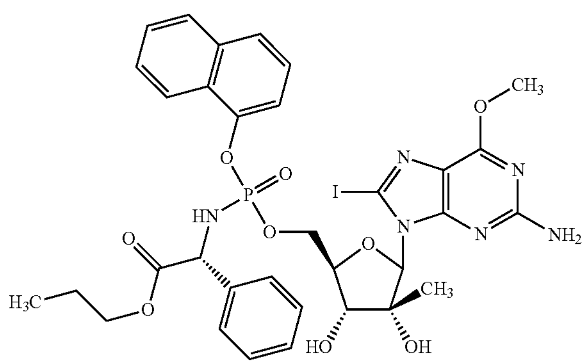 [SMILES: CCCOC(=O)[C@H](NP(=O)(OC[C@H]1OC(n2c(I)nc3c(OC)nc(N)nc32)[C@](C)(O)[C@@H]1O)Oc1cccc2ccccc12)c1ccccc1] | | |
| 64 | 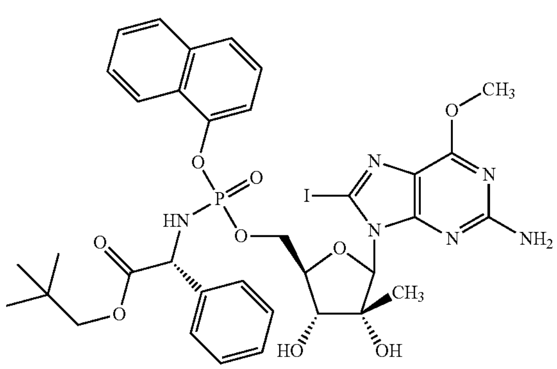 [SMILES: COc1nc(N)nc2c1nc(I)n2C1O[C@H](COP(=O)(N[C@@H](C(=O)OCC(C)(C)C)c2ccccc2)Oc2cccc3ccccc23)[C@@H](O)[C@@]1(C)O] | | |

TABLE 1-continued

| Example No. | Structure | IC$_{50}$ μM | CC$_{50}$ μM |
|---|---|---|---|
| 65 | 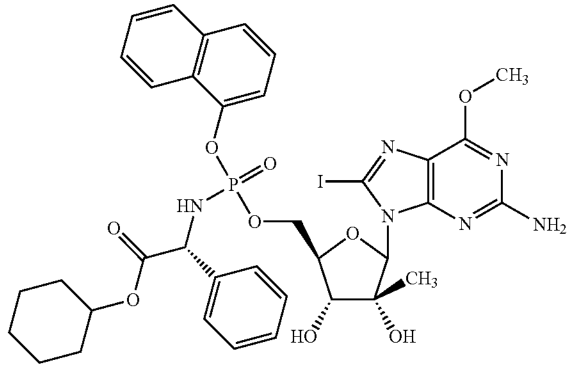 [SMILES: COc1nc(N)nc2c1nc(I)n2C1O[C@H](COP(=O)(N[C@@H](C(=O)OC2CCCCC2)c2ccccc2)Oc2cccc3ccccc23)[C@@H](O)[C@@]1(C)O] | | |
| 66 | 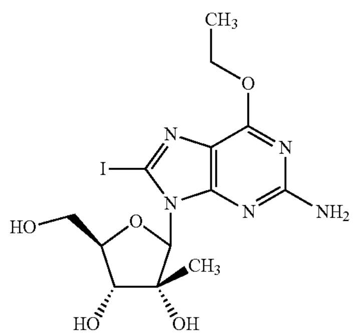 [SMILES: CCOc1nc(N)nc2c1nc(I)n2C1O[C@H](CO)[C@@H](O)[C@@]1(C)O] | | |
| 67 | 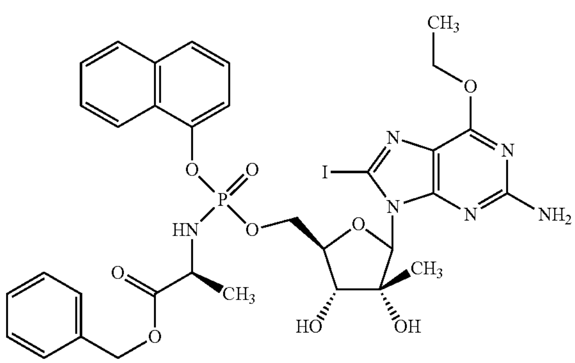 [SMILES: CCOc1nc(N)nc2c1nc(I)n2C1O[C@H](COP(=O)(N[C@@H](C)C(=O)OCc2ccccc2)Oc2cccc3ccccc23)[C@@H](O)[C@@]1(C)O] | | |
| 68 | 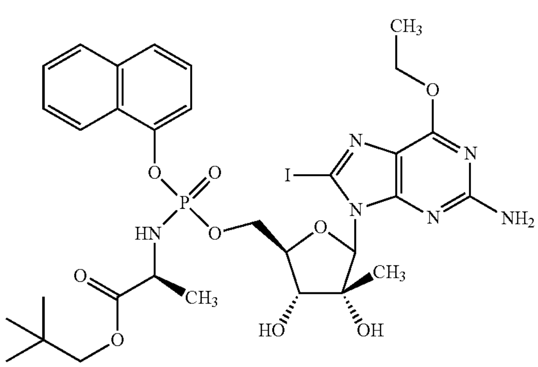 [SMILES: CCOc1nc(N)nc2c1nc(I)n2C1O[C@H](COP(=O)(N[C@@H](C)C(=O)OCC(C)(C)C)Oc2cccc3ccccc23)[C@@H](O)[C@@]1(C)O] | | |

TABLE 1-continued

| Example No. | Structure | IC$_{50}$ μM | CC$_{50}$ μM |
|---|---|---|---|
| 69 | 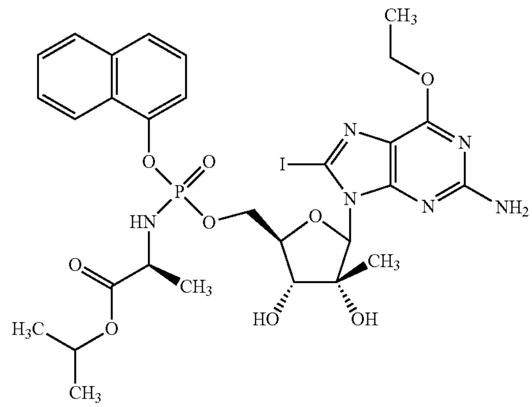 [SMILES: CCOc1nc(N)nc2c1nc(I)n2C1O[C@H](COP(=O)(N[C@@H](C)C(=O)OC(C)C)Oc2cccc3ccccc23)[C@@H](O)[C@@]1(C)O] | | |
| 70 | 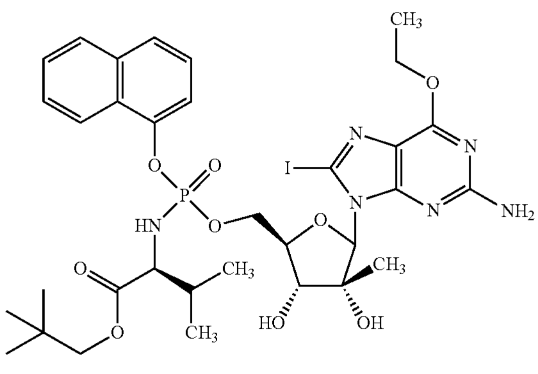 [SMILES: CCOc1nc(N)nc2c1nc(I)n2C1O[C@H](COP(=O)(N[C@H](C(=O)OCC(C)(C)C)C(C)C)Oc2cccc3ccccc23)[C@@H](O)[C@@]1(C)O] | | |
| 71 | 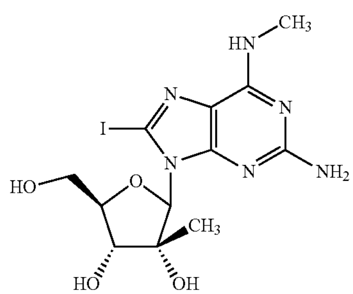 [SMILES: CNc1nc(N)nc2c1nc(I)n2C1O[C@H](CO)[C@@H](O)[C@@]1(C)O] | | |
| 72 | 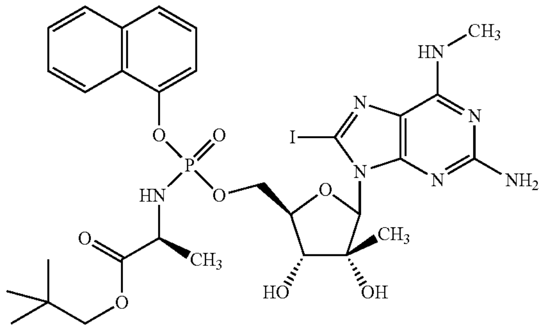 [SMILES: CNc1nc(N)nc2c1nc(I)n2C1O[C@H](COP(=O)(N[C@@H](C)C(=O)OCC(C)(C)C)Oc2cccc3ccccc23)[C@@H](O)[C@@]1(C)O] | | |

TABLE 1-continued

| Example No. | Structure | IC$_{50}$ μM | CC$_{50}$ μM |
|---|---|---|---|
| 73 | 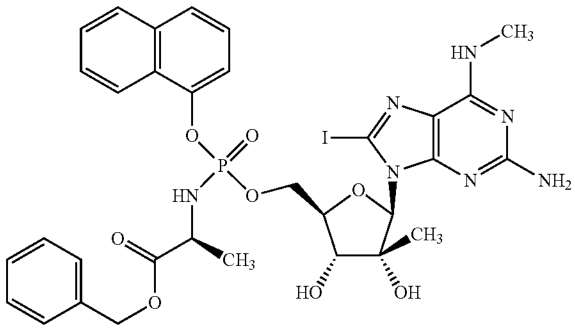 [SMILES: CNc1nc(N)nc2c1nc(I)n2[C@@H]1O[C@H](COP(=O)(N[C@@H](C)C(=O)OCc2ccccc2)Oc2cccc3ccccc23)[C@@H](O)[C@@]1(C)O] | | |
| 74 | 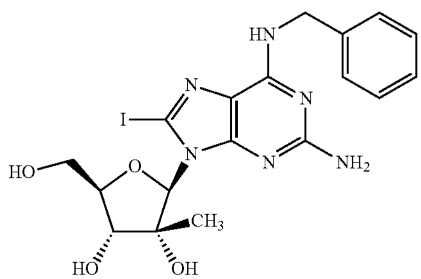 [SMILES: C[C@@]1(O)[C@H](O)[C@@H](CO)O[C@H]1n1c(I)nc2c(NCc3ccccc3)nc(N)nc21] | | |
| 75 | 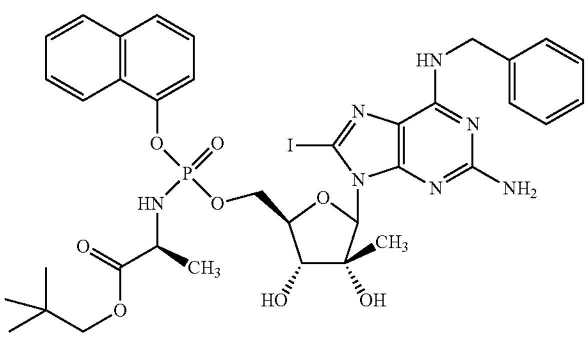 [SMILES: C[C@H](NP(=O)(OC[C@H]1OC(n2c(I)nc3c(NCc4ccccc4)nc(N)nc32)[C@](C)(O)[C@@H]1O)Oc1cccc2ccccc12)C(=O)OCC(C)(C)C] | | |
| 76 | 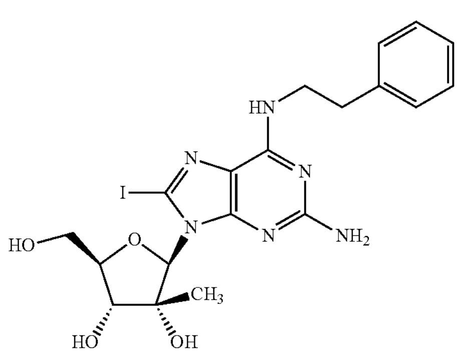 [SMILES: C[C@@]1(O)[C@H](O)[C@@H](CO)O[C@H]1n1c(I)nc2c(NCCc3ccccc3)nc(N)nc21] | | |

TABLE 1-continued

| Example No. | Structure | IC$_{50}$ μM | CC$_{50}$ μM |
|---|---|---|---|
| 77 | 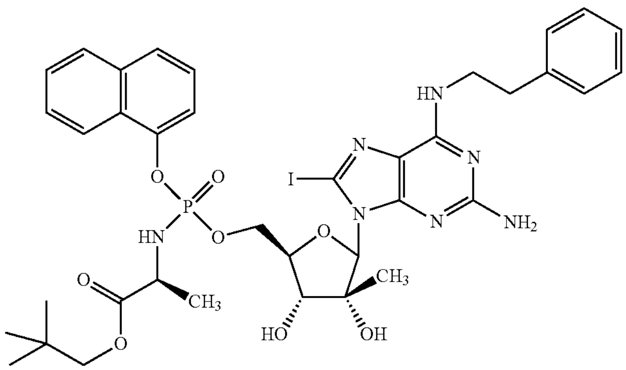 [SMILES: C[C@H](NP(=O)(OC[C@H]1OC(n2c(I)nc3c(NCCc4ccccc4)nc(N)nc32)[C@](C)(O)[C@@H]1O)Oc1cccc2ccccc12)C(=O)OCC(C)(C)C] | | |
| 78 | 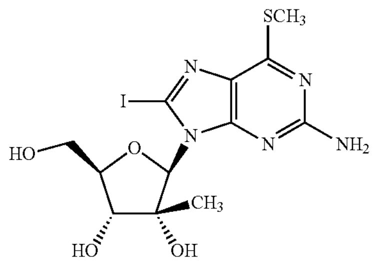 [SMILES: CSc1nc(N)nc2c1nc(I)n2[C@@H]1O[C@H](CO)[C@@H](O)[C@@]1(C)O] | | |
| 79 | 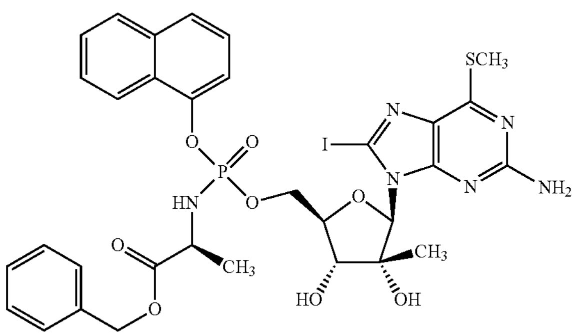 [SMILES: CSc1nc(N)nc2c1nc(I)n2[C@@H]1O[C@H](COP(=O)(N[C@@H](C)C(=O)OCc2ccccc2)Oc2cccc3ccccc23)[C@@H](O)[C@@]1(C)O] | | |
| 80 | 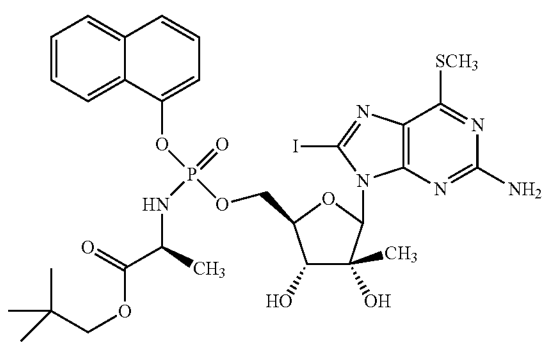 [SMILES: CSc1nc(N)nc2c1nc(I)n2C1O[C@H](COP(=O)(N[C@@H](C)C(=O)OCC(C)(C)C)Oc2cccc3ccccc23)[C@@H](O)[C@@]1(C)O] | | |
| 81 | 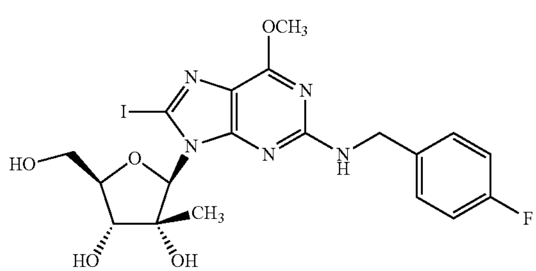 [SMILES: COc1nc(NCc2ccc(F)cc2)nc2c1nc(I)n2[C@@H]1O[C@H](CO)[C@@H](O)[C@@]1(C)O] | | |

TABLE 1-continued

| Example No. | Structure | IC$_{50}$ μM | CC$_{50}$ μM |
|---|---|---|---|
| 82 | 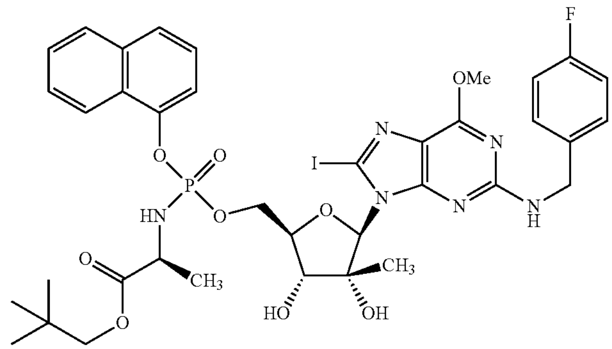 [SMILES: COc1nc(NCc2ccc(F)cc2)nc2c1nc(I)n2[C@@H]1O[C@H](COP(=O)(N[C@@H](C)C(=O)OCC(C)(C)C)Oc2cccc3ccccc23)[C@@H](O)[C@@]1(C)O] | | |
| 83 | 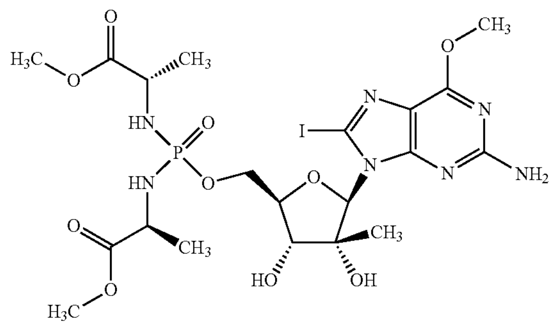 [SMILES: COC(=O)[C@H](C)NP(=O)(N[C@@H](C)C(=O)OC)OC[C@H]1O[C@@H](n2c(I)nc3c(OC)nc(N)nc32)[C@](C)(O)[C@@H]1O] | | |
| 84 | 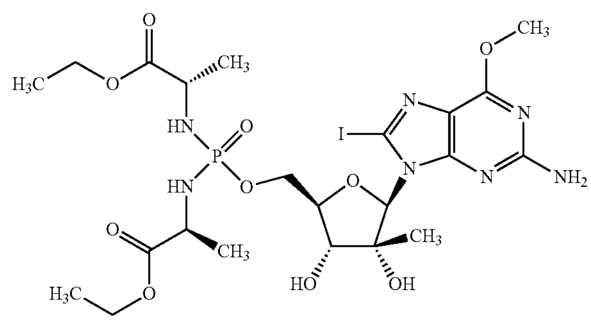 [SMILES: CCOC(=O)[C@H](C)NP(=O)(N[C@@H](C)C(=O)OCC)OC[C@H]1O[C@@H](n2c(I)nc3c(OC)nc(N)nc32)[C@](C)(O)[C@@H]1O] | | |
| 85 | 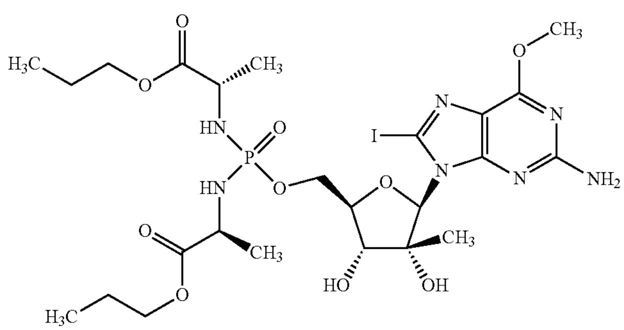 [SMILES: CCCOC(=O)[C@H](C)NP(=O)(N[C@@H](C)C(=O)OCCC)OC[C@H]1O[C@@H](n2c(I)nc3c(OC)nc(N)nc32)[C@](C)(O)[C@@H]1O] | | |

TABLE 1-continued

| Example No. | Structure | IC₅₀ μM | CC₅₀ μM |
|---|---|---|---|
| 86 | 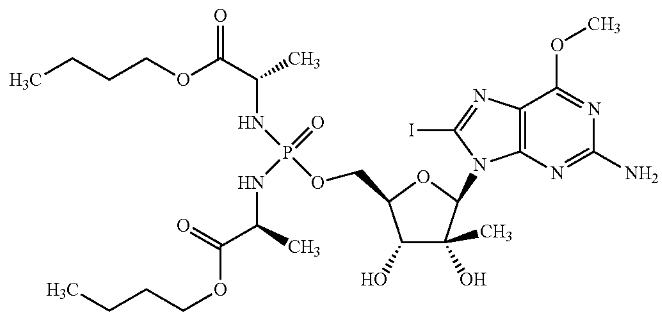 [SMILES: CCCCOC(=O)[C@H](C)NP(=O)(N[C@@H](C)C(=O)OCCCC)OC[C@H]1O[C@@H](n2c(I)nc3c(OC)nc(N)nc32)[C@](C)(O)[C@@H]1O] | | |
| 87 | 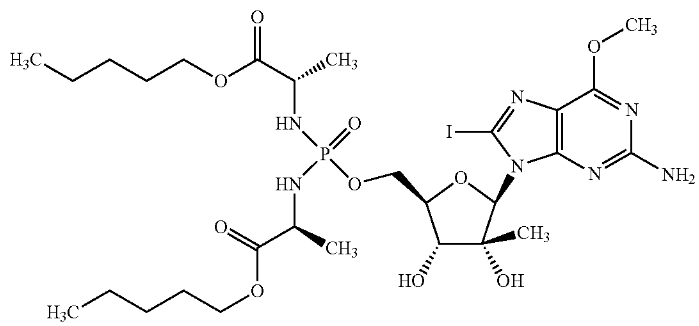 [SMILES: CCCCCOC(=O)[C@H](C)NP(=O)(N[C@@H](C)C(=O)OCCCCC)OC[C@H]1O[C@@H](n2c(I)nc3c(OC)nc(N)nc32)[C@](C)(O)[C@@H]1O] | | |
| 88 | 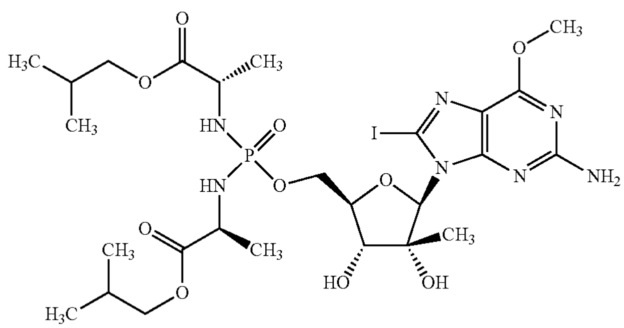 [SMILES: COc1nc(N)nc2c1nc(I)n2[C@@H]1O[C@H](COP(=O)(N[C@@H](C)C(=O)OCC(C)C)N[C@@H](C)C(=O)OCC(C)C)[C@@H](O)[C@@]1(C)O] | | |
| 89 | 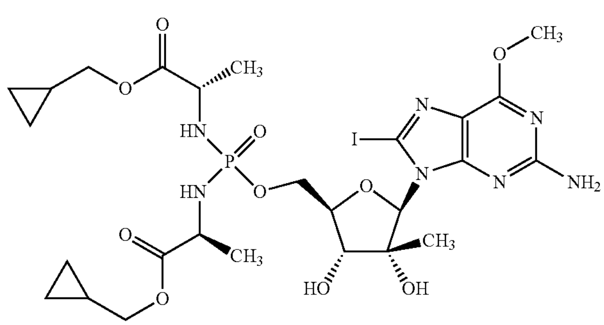 [SMILES: COc1nc(N)nc2c1nc(I)n2[C@@H]1O[C@H](COP(=O)(N[C@@H](C)C(=O)OCC2CC2)N[C@@H](C)C(=O)OCC2CC2)[C@@H](O)[C@@]1(C)O] | | |

TABLE 1-continued

| Example No. | Structure | IC$_{50}$ μM | CC$_{50}$ μM |
|---|---|---|---|
| 90 | 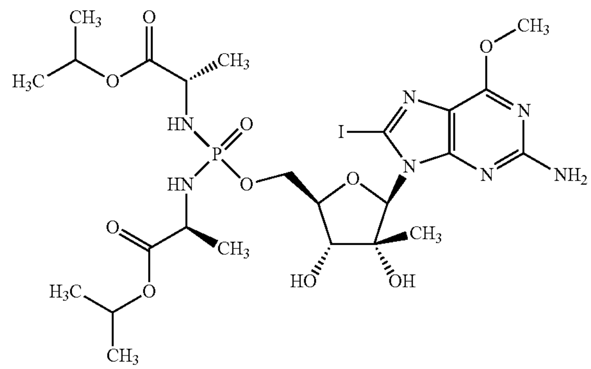 [SMILES: COc1nc(N)nc2c1nc(I)n2[C@@H]1O[C@H](COP(=O)(N[C@@H](C)C(=O)OC(C)C)N[C@@H](C)C(=O)OC(C)C)[C@@H](O)[C@@]1(C)O] | | |
| 91 | 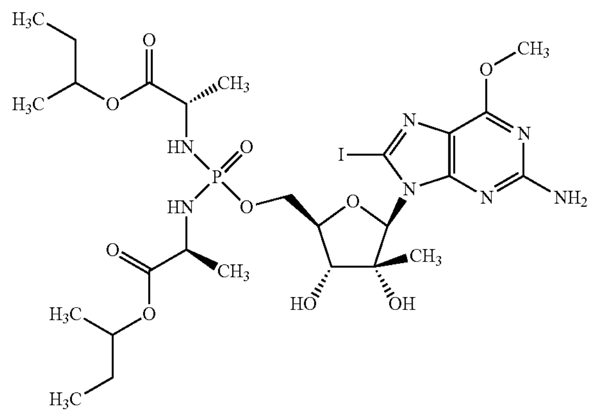 [SMILES: CCC(C)OC(=O)[C@H](C)NP(=O)(N[C@@H](C)C(=O)OC(C)CC)OC[C@H]1O[C@@H](n2c(I)nc3c(OC)nc(N)nc32)[C@](C)(O)[C@@H]1O] | | |
| 92 | 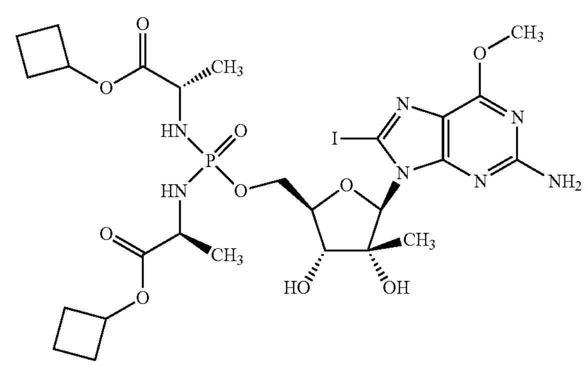 [SMILES: COc1nc(N)nc2c1nc(I)n2[C@@H]1O[C@H](COP(=O)(N[C@@H](C)C(=O)OC2CCC2)N[C@@H](C)C(=O)OC2CCC2)[C@@H](O)[C@@]1(C)O] | | |
| 93 | 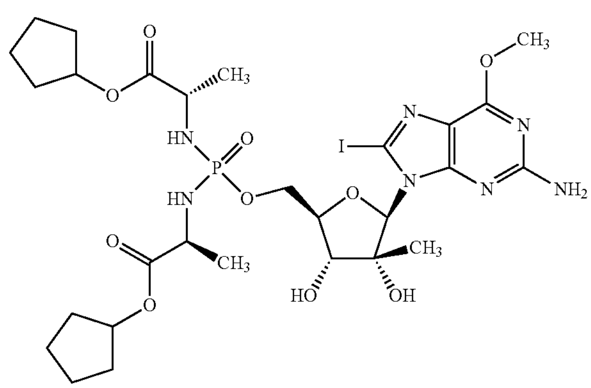 [SMILES: COc1nc(N)nc2c1nc(I)n2[C@@H]1O[C@H](COP(=O)(N[C@@H](C)C(=O)OC2CCCC2)N[C@@H](C)C(=O)OC2CCCC2)[C@@H](O)[C@@]1(C)O] | | |

TABLE 1-continued

| Example No. | Structure | IC$_{50}$ μM | CC$_{50}$ μM |
|---|---|---|---|
| 94 | 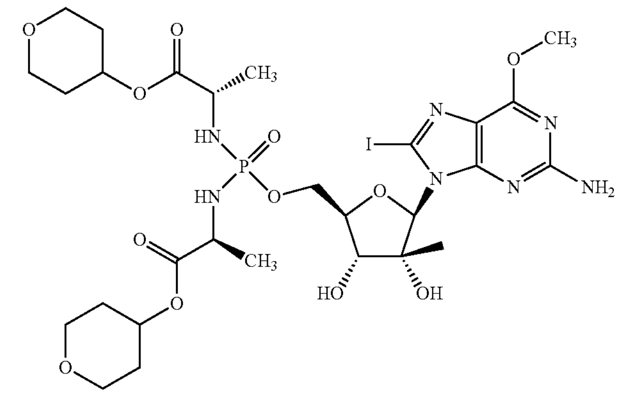 [SMILES: COc1nc(N)nc2c1nc(I)n2[C@@H]1O[C@H](COP(=O)(N[C@@H](C)C(=O)OC2CCOCC2)N[C@@H](C)C(=O)OC2CCOCC2)[C@@H](O)[C@@]1(C)O] | | |
| 95 | 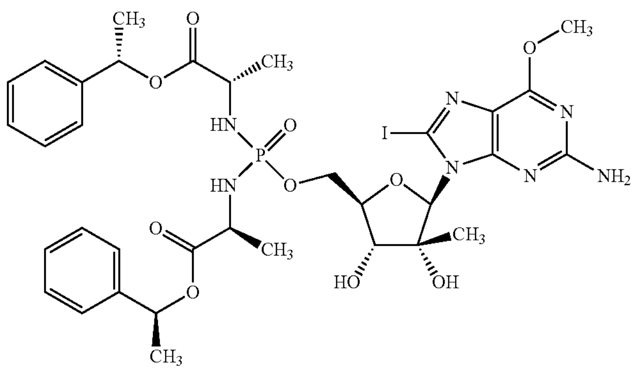 [SMILES: COc1nc(N)nc2c1nc(I)n2[C@@H]1O[C@H](COP(=O)(N[C@@H](C)C(=O)O[C@@H](C)c2ccccc2)N[C@@H](C)C(=O)O[C@@H](C)c2ccccc2)[C@@H](O)[C@@]1(C)O] | | |
| 96 | 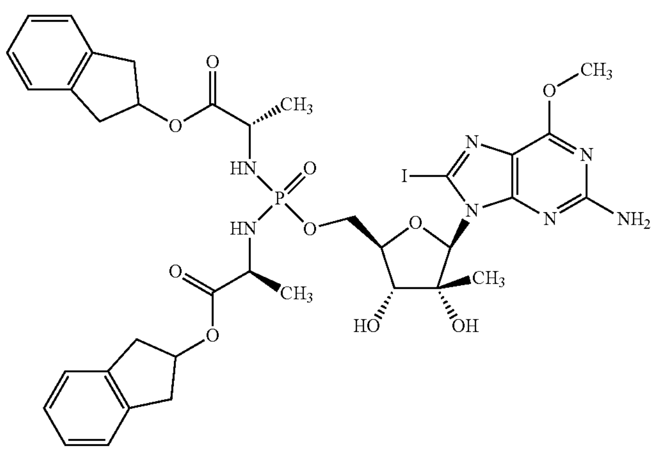 [SMILES: COc1nc(N)nc2c1nc(I)n2[C@@H]1O[C@H](COP(=O)(N[C@@H](C)C(=O)OC2Cc3ccccc3C2)N[C@@H](C)C(=O)OC2Cc3ccccc3C2)[C@@H](O)[C@@]1(C)O] | | |
| 97 | 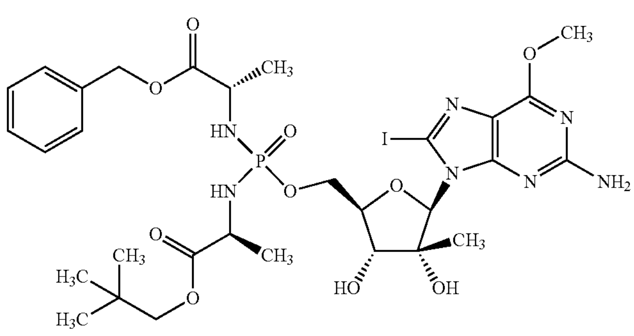 [SMILES: COc1nc(N)nc2c1nc(I)n2[C@@H]1O[C@H](COP(=O)(N[C@@H](C)C(=O)OCc2ccccc2)N[C@@H](C)C(=O)OCC(C)(C)C)[C@@H](O)[C@@]1(C)O] | | |

TABLE 1-continued

| Example No. | Structure | IC$_{50}$ μM | CC$_{50}$ μM |
|---|---|---|---|
| 98 | 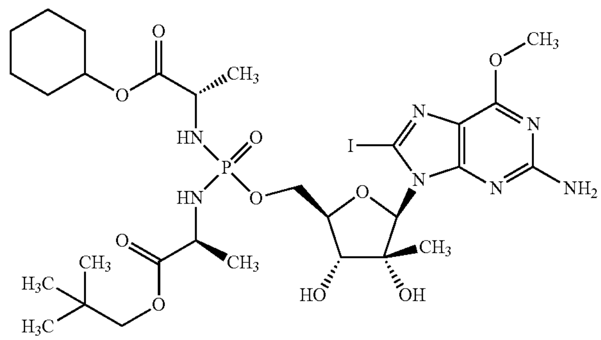 [SMILES: COc1nc(N)nc2c1nc(I)n2[C@@H]1O[C@H](COP(=O)(N[C@@H](C)C(=O)OCC(C)(C)C)N[C@@H](C)C(=O)OC2CCCCC2)[C@@H](O)[C@@]1(C)O] | | |
| 99 | 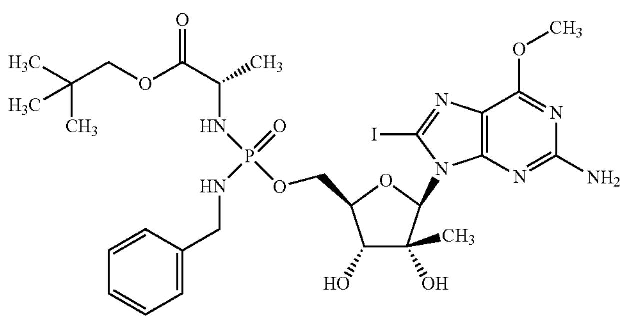 [SMILES: COc1nc(N)nc2c1nc(I)n2[C@@H]1O[C@H](COP(=O)(NCc2ccccc2)N[C@@H](C)C(=O)OCC(C)(C)C)[C@@H](O)[C@@]1(C)O] | | |
| 100 | 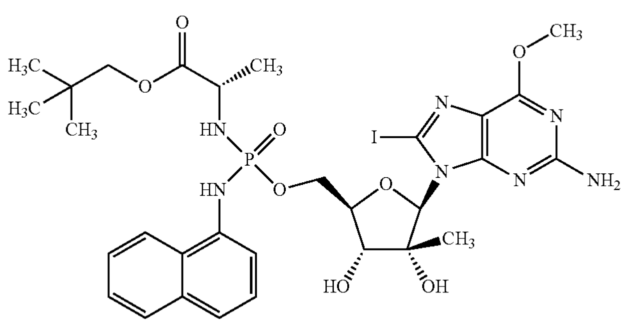 [SMILES: COc1nc(N)nc2c1nc(I)n2[C@@H]1O[C@H](COP(=O)(Nc2cccc3ccccc23)N[C@@H](C)C(=O)OCC(C)(C)C)[C@@H](O)[C@@]1(C)O] | | |
| 101 | 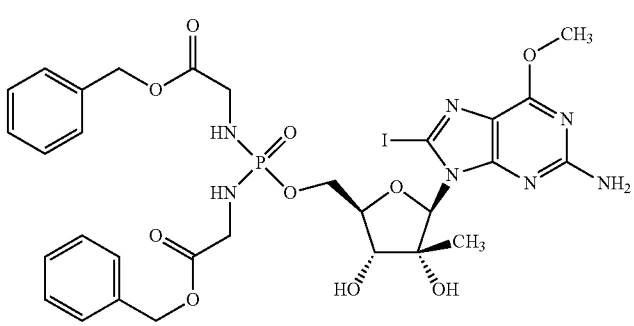 [SMILES: COc1nc(N)nc2c1nc(I)n2[C@@H]1O[C@H](COP(=O)(NCC(=O)OCc2ccccc2)NCC(=O)OCc2ccccc2)[C@@H](O)[C@@]1(C)O] | | |

TABLE 1-continued

| Example No. | Structure | IC$_{50}$ μM | CC$_{50}$ μM |
|---|---|---|---|
| 102 | 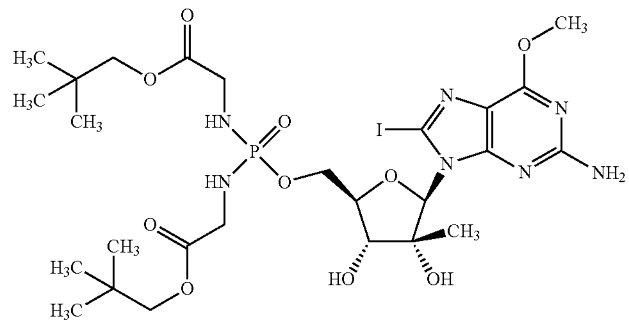 [SMILES: COc1nc(N)nc2c1nc(I)n2[C@@H]1O[C@H](COP(=O)(NCC(=O)OCC(C)(C)C)NCC(=O)OCC(C)(C)C)[C@@H](O)[C@@]1(C)O] | | |
| 103 | 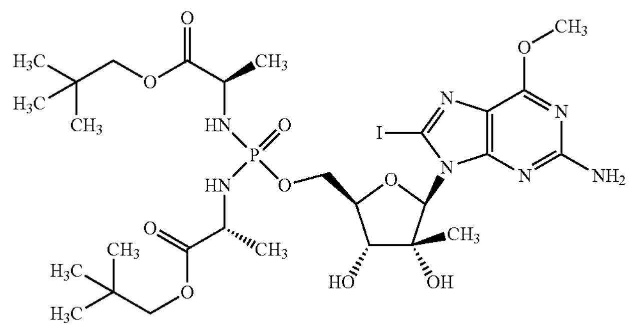 [SMILES: COc1nc(N)nc2c1nc(I)n2[C@@H]1O[C@H](COP(=O)(N[C@H](C)C(=O)OCC(C)(C)C)N[C@H](C)C(=O)OCC(C)(C)C)[C@@H](O)[C@@]1(C)O] | | |
| 104 | 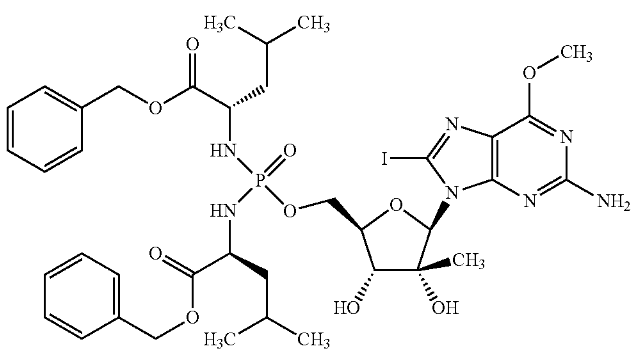 [SMILES: COc1nc(N)nc2c1nc(I)n2[C@@H]1O[C@H](COP(=O)(N[C@@H](CC(C)C)C(=O)OCc2ccccc2)N[C@@H](CC(C)C)C(=O)OCc2ccccc2)[C@@H](O)[C@@]1(C)O] | | |
| 105 | 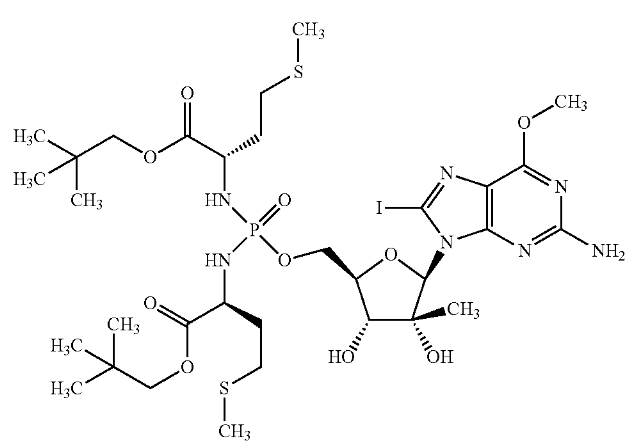 [SMILES: COc1nc(N)nc2c1nc(I)n2[C@@H]1O[C@H](COP(=O)(N[C@@H](CCSC)C(=O)OCC(C)(C)C)N[C@@H](CCSC)C(=O)OCC(C)(C)C)[C@@H](O)[C@@]1(C)O] | | |

TABLE 1-continued

| Example No. | Structure | IC$_{50}$ μM | CC$_{50}$ μM |
|---|---|---|---|
| 106 | 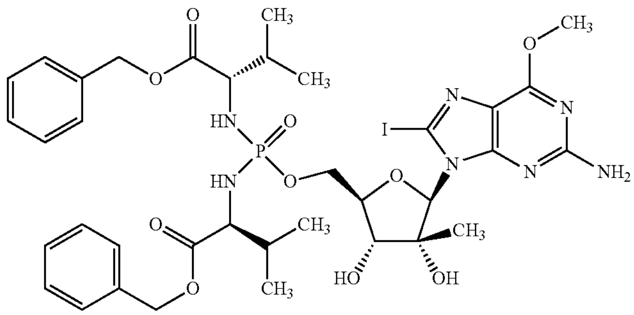 [SMILES: COc1nc(N)nc2c1nc(I)n2[C@@H]1O[C@H](COP(=O)(N[C@H](C(=O)OCc2ccccc2)C(C)C)N[C@H](C(=O)OCc2ccccc2)C(C)C)[C@@H](O)[C@@]1(C)O] | | |
| 107 | 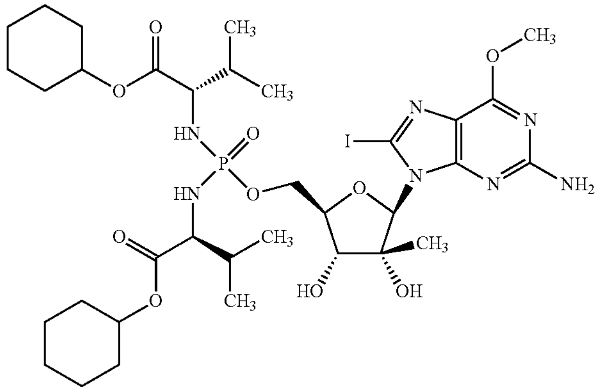 [SMILES: COc1nc(N)nc2c1nc(I)n2[C@@H]1O[C@H](COP(=O)(N[C@H](C(=O)OC2CCCCC2)C(C)C)N[C@H](C(=O)OC2CCCCC2)C(C)C)[C@@H](O)[C@@]1(C)O] | | |
| 108 | 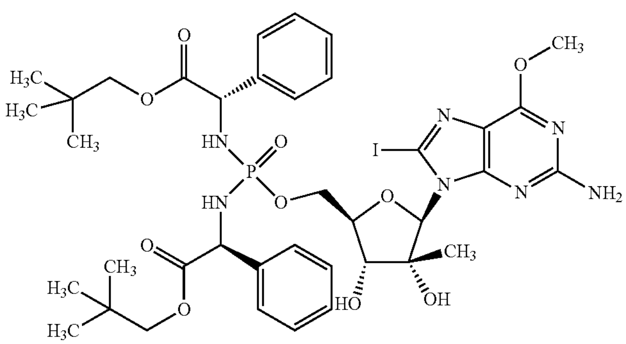 [SMILES: COc1nc(N)nc2c1nc(I)n2[C@@H]1O[C@H](COP(=O)(N[C@H](C(=O)OCC(C)(C)C)c2ccccc2)N[C@H](C(=O)OCC(C)(C)C)c2ccccc2)[C@@H](O)[C@@]1(C)O] | | |
| 109 | 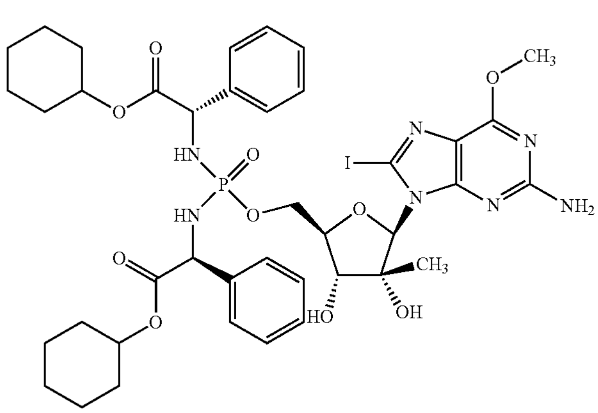 [SMILES: COc1nc(N)nc2c1nc(I)n2[C@@H]1O[C@H](COP(=O)(N[C@H](C(=O)OC2CCCCC2)c2ccccc2)N[C@H](C(=O)OC2CCCCC2)c2ccccc2)[C@@H](O)[C@@]1(C)O] | | |

TABLE 1-continued

| Example No. | Structure | IC$_{50}$ µM | CC$_{50}$ µM |
|---|---|---|---|
| 110 | 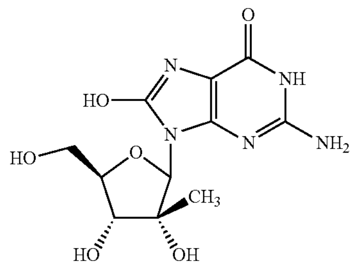 [SMILES: C[C@]1(O)C(n2c(O)nc3c(=O)[nH]c(N)nc32)O[C@H](CO)[C@H]1O] | | |

While the invention has been described with reference to particularly preferred embodiments and examples, those skilled in the art recognize that various modifications may be made to the invention without departing from the spirit and scope thereof.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

ABBREVIATIONS AND ACRONYMS

A number of abbreviations and acronyms are used herein, and a full description of these are provided as follows:
ACN acetonitrile
AIBN azobisisobutryonitrile
anhy anhydrous
Bn benzyl (phenylmethyl)
Boc benzyloxycarbonyl
BSA benzenesulfonic acid
Bu butyl
n-BuOH n-butanol
t-BuOH tert-butanol
t-BuOK potassium—tert-butoxide
tert-BuMgCl tert-butylmagnesium chloride
CDCl$_3$ deuterochloroform
CI-MS chemical ionization mass spectrometry
$^{13}$C NMR carbon-13 nuclear magnetic resonance spectroscopy
conc concentrated
d doublet (NMR)
dd doublet of doublets (NMR)
ddd double doublet of doublets (nmr
DBU diaza(1,3)bicyclo[5.4.0]undecane
DCC dicyclohexylcarbodiimide
DCM dichloromethane
DMAP 4-dimethylaminopyridine
DMF N,N-dimethylformamide
DMSO dimethyl sulfoxide
dt doublet of triplets (NMR)
EDCI 1-(3-dimethylamnopropyl)-3-ethylcarbodiimide hydrochloride
ee enantiomeric excess
EI-MS electron impact mass spectrometry
equiv equivalent(s)
ESI electrospray ionization
ES-MS electrospray mass spectrometry
Et$_3$N triethylamine
Et$_2$O ethyl ether
EtOAc ethyl acetate
EtOH ethanol
$^{19}$F NMR fluorine-19 nuclear magnetic resonance spectroscopy
g gram(s)
GC-MS gas chromatography-mass spectrometry
h hour
HCV hepatitis C virus
$^1$H NMR proton nuclear magnetic resonance spectroscopy
HPLC high performance liquid chromatography
HRMS high resolution mass spectrometry
IMPDH inosine 5' monophosphate dehydroxygenase
J NMR coupling constant
LC/MS liquid chromatography-mass spectrometry
LG leaving group
LHMDS Lithium hexamethyldisilazide
m multiplet (NMR)
MDI methylenediphenyldisocyanate
Me methyl
MeOH methanol
MeOH-d$_4$ methanol-d$_4$
mg milligram
MHz megahertz
mL milliliter
mmol millimole
mp melting point
MTBE methyl t-butyl ether
NaOMe sodium methoxide
NBS N-Bromo succinimide
NCS N-Chloro succinimide
NIS N-Iodo succinimide
NMI N-methylimidazole
NMO N-methylmorpholine-N-oxide
NMR nuclear magnetic resonance
$^{31}$P NMR phosphorous-31 nuclear magnetic resonance spectroscopy
ppm part per million
q quartet (NMR)
pTSA p-toluenesulfonic acid
RBV ribavirin
Red-Al® sodium bis(2-methoxyethoxy)aluminumhydride
R$_f$ retention factor (TLC)
rt room temperature
s singlet (NMR)
t triplet (NMR)
TBAF tetra-n-butylammonium fluoride
TBPPS tetra-n-butylphosphonium persulfate
TCFM trichlorofluoromethane
TEA triethylamine
TFA trifluoroacetic acid THF tetrahydrofuran
TMS tetramethylsilane
TMSCl trimethylsilyl chloride
TMSI trimethylsilyl iodide
TMSOTf trimethylsilyl trifluoromethanesulfonate
$t_R$ retention time
TLC thin layer chromatography
TOF ES+ time of flight electrospray (mass spectroscopy)
TOF AP+ time of flight advanced performance (mass spectroscopy)
UV ultraviolet
VCD Vibrational Circular Dichroism

What is claimed is:

1. A compound of formula (I) having the structure:

$$\text{(I)}$$

wherein
U and V are each independently selected from the group consisting of
  H
  OH
  Cl
  Br
  I
  $OR^1$
  $NH_2$
  $NHR^2$
  $NR^2R^2$
  SH
  and
  $SR^3$
  wherein
    $R^1$, $R^2$, and $R^3$ are independently $C_1$-$C_6$ alkyl or alkyl($C_1$-$C_3$)aryl;
W is independently selected from the group consisting of
  I
  OH
  $NH_2$
  SH
  $SR^4$
  $OR^5$
  $NHR^6$
  and
  $NR^6R^6$,
  wherein
    $R^4$, $R^5$ and $R^6$ are independently $C_1$-$C_6$ alkyl or alkyl($C_1$-$C_3$)aryl;
$X^1$ is OH or F;
$X^2$ is OH;
Y is hydrogen or $N_3$ (azido);
Z is selected from the group consisting of
  H
  —P(O)(OAr)$NHR^7$
  —P(O)(NHR$^7$)$_2$
  —P(O)(O$^-$)NHR$^7$
  —P(O)O$^-_2$ (monophosphate)
  and
  —PO$_2$—O—PO$_2$—O—PO$_3$ (triphosphate)
wherein
  $R^7$ is
    —C($R^8$)($R^9$)C(O)O$R^{10}$
    wherein
      $R^8$ and $R^9$ are independently
        hydrogen,
        alkyl,
        aryl($C_1$-$C_6$)alkyl,
        or
        phenyl,
      $R^{10}$ is $C_1$-$C_6$ alkyl
        aryl($C_1$-$C_6$)alkyl, (indanyl)      (4-pyranyl)

and
Ar is independently selected from the group consisting of
  phenyl
  1-naphthyl
  2-naphthyl and wherein the compound has a specific formula selected from the group consisting of the following:

125
-continued
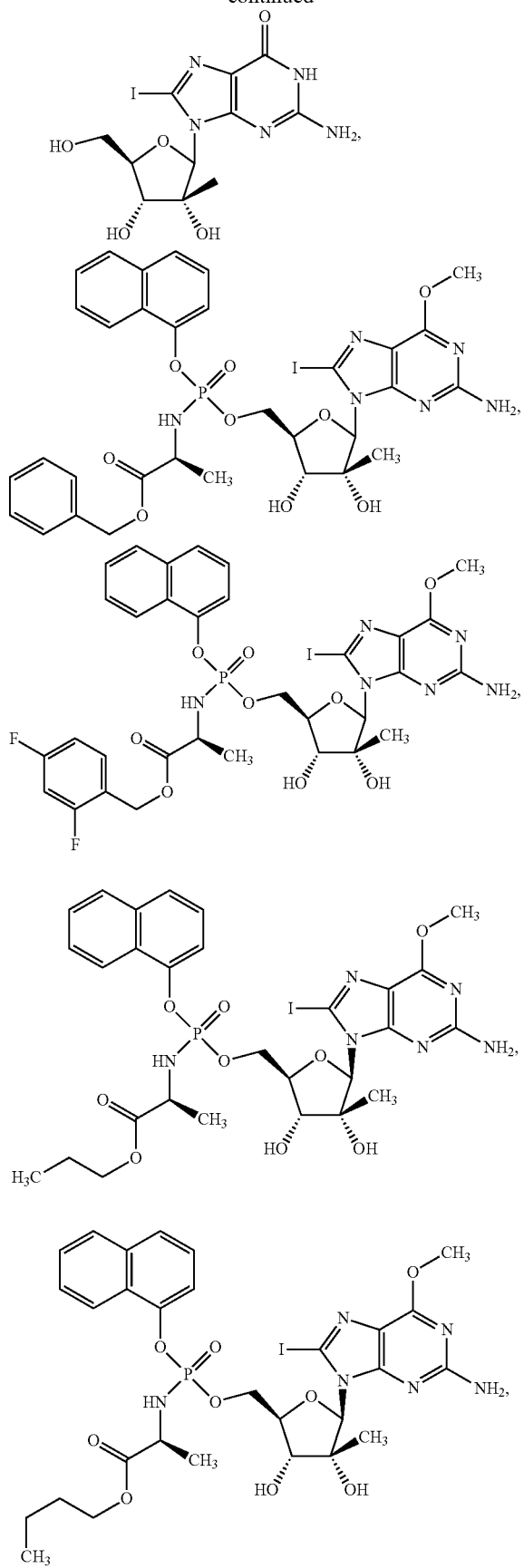
126
-continued
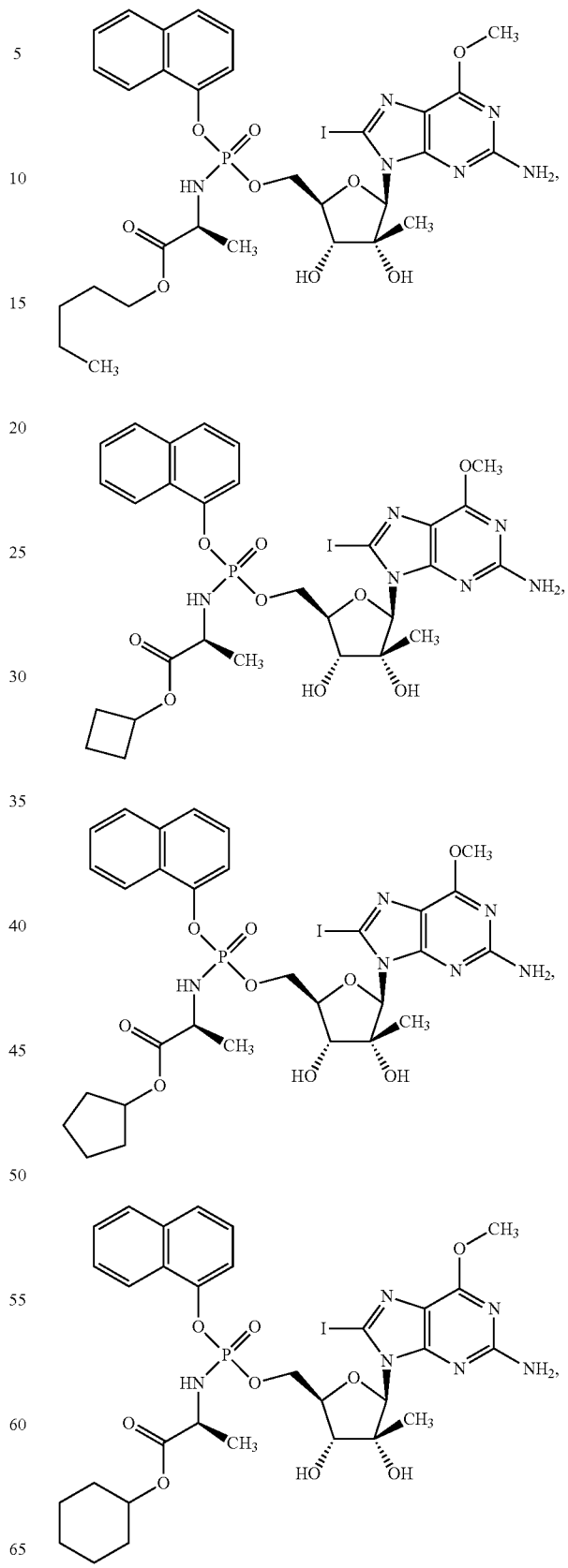

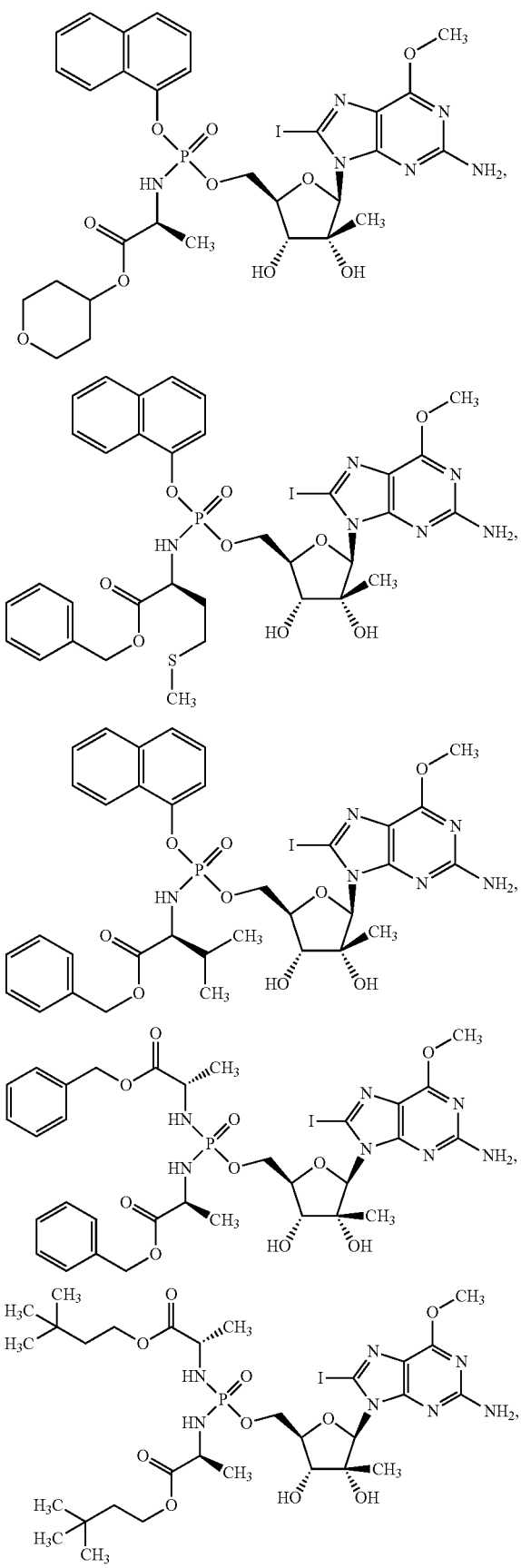
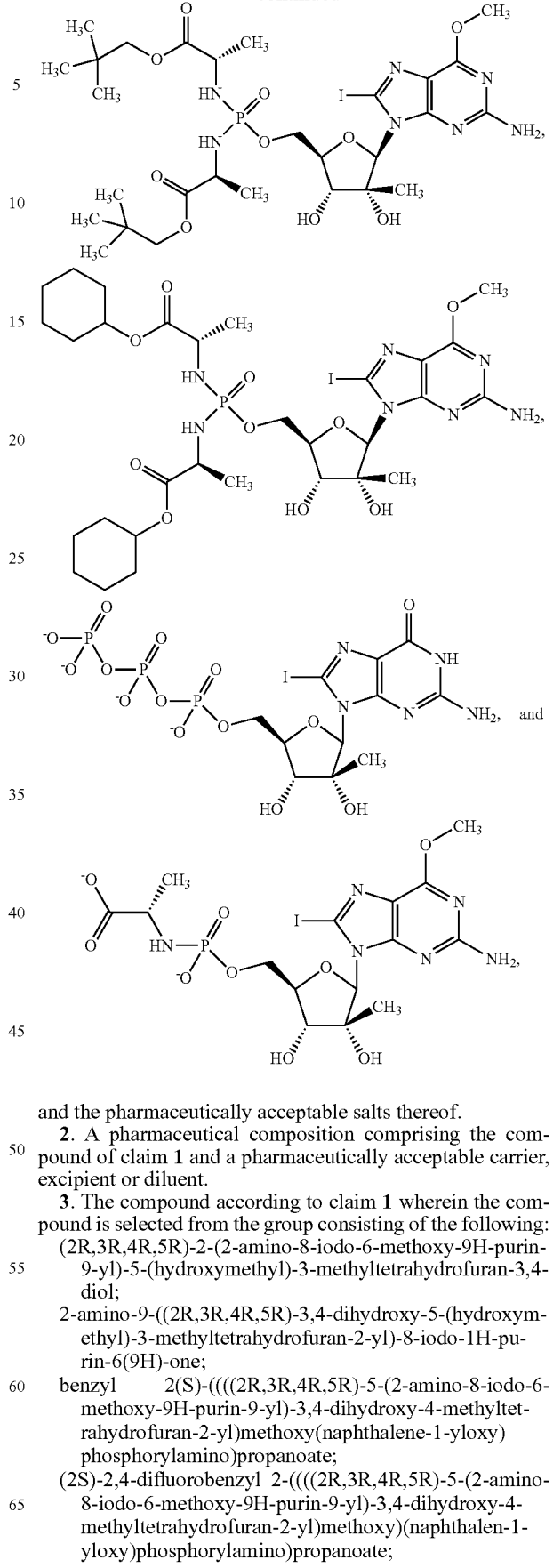

and the pharmaceutically acceptable salts thereof.

2. A pharmaceutical composition comprising the compound of claim 1 and a pharmaceutically acceptable carrier, excipient or diluent.

3. The compound according to claim 1 wherein the compound is selected from the group consisting of the following:

(2R,3R,4R,5R)-2-(2-amino-8-iodo-6-methoxy-9H-purin-9-yl)-5-(hydroxymethyl)-3-methyltetrahydrofuran-3,4-diol;

2-amino-9-((2R,3R,4R,5R)-3,4-dihydroxy-5-(hydroxymethyl)-3-methyltetrahydrofuran-2-yl)-8-iodo-1H-purin-6(9H)-one;

benzyl 2(S)-(((((2R,3R,4R,5R)-5-(2-amino-8-iodo-6-methoxy-9H-purin-9-yl)-3,4-dihydroxy-4-methyltetrahydrofuran-2-yl)methoxy(naphthalene-1-yloxy)phosphorylamino)propanoate;

(2S)-2,4-difluorobenzyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;

(2S)-propyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;
(2S)-butyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;
(2S)-pentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;
(2S)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;
(2S)-cyclobutyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;
(2S)-cyclopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;
(2S)-cyclohexyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;
(2S)-tetrahydro-2H-pyran-4-yl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;
(2S)-benzyl 2-((((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-4-(methylthio)butanoate;
(2S)-benzyl 2-((((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate;
(2S,2'S)-benzyl 2,2'-(((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;
(2S,2'S)-bis(3,3-dimethylbutyl) 2,2'-(((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;
(2S,2'S)-neopentyl 2,2'-(((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;
(2S,2'S)-dicyclohexyl 2,2'-(((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;
((2R,3R,4R,5R)-5-(2-amino-8-iodo-6-oxo-1H-purin-9(6H)-yl)-3,4-dihydroxy-4-methyltetrahydrofuran-2-yl)methyl phosphate;
((2R,3R,4R,5R)-5-(2-amino-8-iodo-6-oxo-1H-purin-9(6H)-yl)-3,4-dihydroxy-4-methyltetrahydrofuran-2-yl)methyl triphosphate;
(S)-2-(((((2R,3R,4R,5R)-5-(2-amino-8-iodo-6-methoxy-9H-purin-9-yl)-3,4-dihydroxy-4-methyltetrahydrofuran-2-yl)methoxy)oxidophosphorylamino)propanoate;
1(S)-phenylethyl 2(S)-(((((2R,3R,4R,5R)-5-(2-amino-8-iodo-6-methoxy-9H-purin-9-yl)-3,4-dihydroxy-4-methyltetrahydrofuran-2-yl)methoxy(naphthalene-1-yloxy)phosphorylamino)propanoate;
(2S)-2,3-dihydro-1H-inden-2-yl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;
(2S)-3,3-dimethylbutyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;
(2S)-isobutyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;
(S)—P 2,2-dimethylpropyl 2(S)-(((((2R,3R,4R,5R)-5-(2-amino-8-iodo-6-methoxy-9H-purin-9-yl)-3,4-dihydroxy-4-methyltetrahydrofuran-2-yl)methoxy(naphthalene-1-yloxy)phosphorylamino)propanoate;
(R)—P 2,2-dimethylpropyl 2(S)-(((((2R,3R,4R,5R)-5-(2-amino-8-iodo-6-methoxy-9H-purin-9-yl)-3,4-dihydroxy-4-methyltetrahydrofuran-2-yl)methoxy(naphthalene-1-yloxy)phosphorylamino)propanoate;
(2S)-isopropyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;
(2S)-2,4-difluorobenzyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(quinolin-5-yloxy)phosphorylamino)propanoate;
(2S)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(quinolin-5-yloxy)phosphorylamino)propanoate;
(2S)-tetrahydro-2H-pyran-4-yl 2-(((((2R,3R,4R,5R)-5-(2-amino-8-iodo-6-methoxy-9H-purin-9-yl)-3,4-dihydroxy-4-methyltetrahydrofuran-2-yl)methoxy)(quinolin-5-yloxy)phosphorylamino)propanoate;
(2S)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(quinolin-6-yloxy)phosphorylamino)propanoate;
(2S)-tetrahydro-2H-pyran-4-yl 2-(((((2R,3R,4R,5R)-5-(2-amino-8-iodo-6-methoxy-9H-purin-9-yl)-3,4-dihydroxy-4-methyltetrahydrofuran-2-yl)methoxy)(quinolin-6-yloxy)phosphorylamino)propanoate;
(2S)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(phenoxy)phosphorylamino)propanoate;
(2S)-2,4-difluorobenzyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate;
(2S)-methyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate;
(2S)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate;
(2S)-cyclopropylmethyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-cyclobutyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-cyclopentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-cyclohexyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-tetrahydro-2H-pyran-4-yl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-2,4 difluorobenzyl 2-((((2R,3R,4R)-5-(2-amino-8-iodo-6-methoxy-9H-purin-9-yl)-3,4-dihydroxy-4-methyltetrahydrofuran-2-yl)methoxy)(quinolin-5-yloxy)phosphorylamino)-3-methylbutanoate;

(2S)-neopentyl 2-((((2R,3R,4R)-5-(2-amino-8-iodo-6-methoxy-9H-purin-9-yl)-3,4-dihydroxy-4-methyltetrahydrofuran-2-yl)methoxy)(quinolin-6-yloxy)phosphorylamino)-3-methylbutanoate;

(2R)-neopentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)propanoate;

(2S)—((S)-1-phenylethyl) 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-4-(methylthio)butanoate;

(2S)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-4-(methylthio)butanoate;

(2S)-neopentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-4-methylpentanoate;

(2S,3R)-neopentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-3-methylpentanoate;

(2S)-benzyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-propyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-cyclohexyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2R)-benzyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2R)-propyl 2-((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2R)-neopentyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2R)-cyclohexyl 2-(((((2R,3R,4R,5R)-5-(2-amino-8-iodo-6-methoxy-9H-purin-9-yl)-3,4-dihydroxy-4-methyltetrahydrofuran-2-yl)methoxy)(naphthalen-1-yloxy)phosphorylamino)-2-phenylacetate;

(3R,4R,5R)-2-(2-amino-6-ethoxy-8-iodo-9H-purin-9-yl)-5-(hydroxymethyl)-3-methyltetrahydrofuran-3,4-diol;

benzyl 2(S)-((((2R,3R,4R,5R)-5-(2-amino-6-ethoxy-8-iodo-9H-purin-9-yl)-3,4-dihydroxy-4-methyltetrahydrofuran-2-yl)methoxy(naphthalene-1-yloxy)phosphorylamino)-3-methylbutanoate;

(2S)-neopentyl 2-((((2R,3R,4R)-5-(2-amino-6-ethoxy-8-iodo-9H-purin-9-yl)-3,4-dihydroxy-4-methyltetrahydrofuran-2-yl)methoxy)(naphthalen-1-yloxy)phosphorylamino)propanoate;

(2S)-isopropyl 2-((((2R,3R,4R)-5-(2-amino-6-ethoxy-8-iodo-9H-purin-9-yl)-3,4-dihydroxy-4-methyltetrahydrofuran-2-yl)methoxy)(naphthalen-1-yloxy)phosphorylamino)propanoate;

(2S)-neopentyl 2-((((2R,3R,4R)-5-(2-amino-6-ethoxy-8-iodo-9H-purin-9-yl)-3,4-dihydroxy-4-methyltetrahydrofuran-2-yl)methoxy)(naphthalen-1-yloxy)phosphorylamino)-3-methylbutanoate;

(2R,3R,4R,5R)-2-(2-amino-8-iodo-6-(methylamino)-9H-purin-9-yl)-5-(hydroxymethyl)-3-methyltetrahydrofuran-3,4-diol;

(2S)-neopentyl 2-((((2R,3R,4R,5R)-5-(2-amino-8-iodo-6-(methylamino)-9H-purin-9-yl)-3,4-dihydroxy-4-methyltetrahydrofuran-2-yl)methoxy)(naphthalen-1-yloxy)phosphorylamino)propanoate (2S)-benzyl 2-((((2R,3R,4R,5R)-5-(2-Amino-8-iodo-6-(methylamino)-9H-purin-9-yl)-3,4-dihydroxy-4-methyltetrahydrofuran-2-yl)methoxy)(naphthalen-1-yloxy)phosphorylamino)propanoate;

(2R,3R,4R,5R)-2-(2-amino-6-(benzylamino)-8-iodo-9H-purin-9-yl)-5-(hydroxymethyl)-3-methyltetrahydrofuran-3,4-diol;

(2S)-neopentyl 2-((((2R,3R,4R,5R)-5-(2-amino-6-(benzylamino)-8-iodo-9H-purin-9-yl)-3,4-dihydroxy-4-methyltetrahydrofuran-2-yl)methoxy)(naphthalen-1-yloxy)phosphorylamino)propanoate;

(2R,3R,4R,5R)-2-(2-amino-8-iodo-6-(phenethylamino)-9H-purin-9-yl)-5-(hydroxymethyl)-3-methyltetrahydrofuran-3,4-diol;

(2S)-neopentyl 2-((((2R,3R,4R,5R)-5-(2-amino-8-iodo-6-(phenethylamino)-9H-purin-9-yl)-3,4-dihydroxy-4-methyltetrahydrofuran-2-yl)methoxy)(naphthalen-1-yloxy)phosphorylamino)propanoate;

(2R,3R,4R,5R)-2-(2-amino-8-iodo-6-(methylthio)-9H-purin-9-yl)-5-(hydroxymethyl)-3-methyltetrahydrofuran-3,4-diol;

(2S)-benzyl 2-((((2R,3R,4R,5R)-5-(2-amino-8-iodo-6-(methylthio)-9H-purin-9-yl)-3,4-dihydroxy-4-methyltetrahydrofuran-2-yl)methoxy)(naphthalen-1-yloxy)phosphorylamino)propanoate;

(2S)-neopentyl 2-((((2R,3R,4R,5R)-5-(2-amino-8-iodo-6-(methylthio)-9H-purin-9-yl)-3,4-dihydroxy-4-methyltetrahydrofuran-2-yl)methoxy)(naphthalen-1-yloxy)phosphorylamino)propanoate;

(2R,3R,4R,5R)-2-(2-(4-fluorobenzylamino)-8-iodo-6-methoxy-9H-purin-9-yl)-5-(hydroxymethyl)-3-methyltetrahydrofuran-3,4-diol;

(2S)-neopentyl 2-((((2R,3R,4R,5R)-5-(2-(4-fluorobenzylamino)-8-iodo-6-methoxy-9H-purin-9-yl)-3,4-dihydroxy-4-methyltetrahydrofuran-2-yl)methoxy)(naphthalen-1-yloxy)phosphorylamino)propanoate;

(2S,2'S)-dimethyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;

(2S,2'S)-diethyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;

(2S,2'S)-dipropyl-((((2R,3S,4R,5R)-5-(2-amino-8-iodo-6-methoxy-9H-purin-9-yl)-3,4-dihydroxy-4-methyltetrahydrofuran-2-yl)methoxy)phosphoryl)-(2,2')-bis-amino-dipropanoate;

(2S,2'S)-dibutyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate (2S,2'S)-dipentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;

(2S,2'S)-diisobutyl-((((2R,3S,4R,5R)-5-(2-amino-8-iodo-6-methoxy-9H-purin-9-yl)-3,4-dihydroxy-4-methyltetrahydrofuran-2-yl)methoxy)phosphoryl)(2,2')-bis-amino-dipropanoate;

(2S,2'S)-bis (cyclopropylmethyl) 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;

(2S,2'S)-diisopropyl-((((2R,3S,4R,5R)-5-(2-amino-8-iodo-6-methoxy-9H-purin-9-yl)-3,4-dihydroxy-4-methyltetrahydrofuran-2-yl)methoxy)phosphoryl)-(2,2')-bis-amino-dipropanoate;

(2S,2'S)-sec-butyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;

(2S,2'S)-dicyclobutyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;

(2S,2'S)-dicyclopentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;

(2S,2'S)-bis (tetrahydro-2H-pyran-4-yl) 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;

(2S,2'S)—(S)-phenylethyl-((((2R,3S,4R,5R)-5-(2-amino-8-iodo-6-methoxy-9H-purin-9-yl)-3,4-dihydroxy-4-methyltetrahydrofuran-2-yl)methoxy)phosphoryl)-(2,2')-bis-amino-dipropanoate;

(2S,2'S)-bis(2,3-dihydro-1H-inden-2-yl) 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;

(2S)-benzyl 2-((((2R,3R,4R,5R)-5-(2-amino-8-iodo-6-methoxy-9H-purin-9-yl)-3,4-dihydroxy-4-methyltetrahydrofuran-2-yl)methoxy)((S)-1-(neopentyloxy)-1-oxopropan-2-ylamino)phosphorylamino)propanoate;

(2S)-cyclohexyl 2-((((2R,3R,4R,5R)-5-(2-amino-8-iodo-6-methoxy-9H-purin-9-yl)-3,4-dihydroxy-4-methyltetrahydrofuran-2-yl)methoxy)((S)-1-(neopentyloxy)-1-oxopropan-2-ylamino)phosphorylamino)propanoate;

(2S)-neopentyl 2-((((2R,3R,4R,5R)-5-(2-amino-8-iodo-6-methoxy-9H-purin-9-yl)-3,4-dihydroxy-4-methyltetrahydrofuran-2-yl)methoxy)(benzylamino)phosphorylamino)propanoate;

(2S)-neopentyl 2-((((2R,3R,4R)-5-(2-amino-8-iodo-6-methoxy-9H-purin-9-yl)-3,4-dihydroxy-4-methyltetrahydrofuran-2-yl)methoxy)(naphthalen-1-ylamino)phosphorylamino)propanoate;

benzyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)diacetate;

neopentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)diacetate;

(2R,2'R)-neopentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)dipropanoate;

(2S,2'S)-benzyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)bis(4-methylpentanoate);

(2R,2'R)-neopentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)bis(4-methylthiobutanoate;

(2S,2'S)-benzyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)bis(3-methyl butanoate);

(2S,2'S)-dicyclohexyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)bis(3-methylbutanoate);

(2S,2'S)-neopentyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)bis(2-phenylacetate); and (2S,2'S)-dicyclohexyl 2,2'-((((2R,3R,4R,5R)-5-(2-amino-8-iodo-6-methoxy-9H-purin-9-yl)-3,4-dihydroxy-4-methyltetrahydrofuran-2-yl)methoxy)phosphoryl)bis(azanediyl)bis(2-phenylacetate);

and the pharmaceutically acceptable salts thereof.

4. A method for treating a viral infection in a mammal infected by a virus in the Flaviviridae family of viruses comprising administering to a mammal in need thereof an effective amount of the compound of claim 1; and wherein said virus is hepatitis C virus.

5. A method for treating a hepatitis C viral infection in a mammal comprising administering to a mammal in need thereof an effective amount of the pharmaceutical composition of claim 2.

6. A composition comprising a compound of formula (I) having the structure:

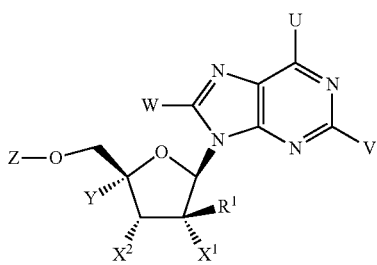 (I)

wherein
U and V are each independently selected from the group consisting of
H
OH
Cl
Br
I
OR¹
NH₂
NHR²
NR²R²
SH
and
SR³
wherein
R¹, R², and R³ are independently $C_1$-$C_6$ alkyl or alkyl($C_1$-$C_3$)aryl;
W is independently selected from the group consisting of
I
OH
NH₂
SH
SR⁴
OR⁵
NHR⁶
and
NR⁶R⁶,
wherein
R⁴, R⁵ and R⁶ are independently $C_1$-$C_6$ alkyl or alkyl($C_1$-$C_3$)aryl;
X¹ is OH or F;
X² is OH;
Y is hydrogen or N₃ (azido);
Z is selected from the group consisting of
H
—P(O)(OAr)NHR⁷
—P(O)(NHR⁷)₂
—P(O)(O⁻)NHR⁷
—P(O)O⁻₂ (monophosphate)
and
—PO₂—O—PO₂—O—PO₃ (triphosphate)
wherein
R⁷ is
—C(R⁸)(R⁹)C(O)OR¹⁰
wherein
R⁸ and R⁹ are independently
hydrogen,
alkyl,
aryl($C_1$-$C_6$)alkyl,
or
phenyl,
R¹⁰ is $C_1$-$C_6$ alkyl
aryl($C_1$-$C_6$)alkyl,

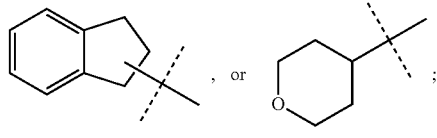

(indanyl)     (4-pyranyl)

and
Ar is independently selected from the group consisting of
phenyl
1-naphthyl
2-naphthyl

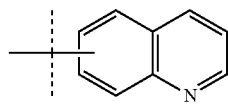

and

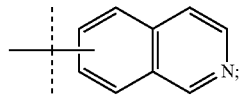

and the pharmaceutically acceptable salts thereof,
wherein the composition comprises a mixture of at least two different diastereomers around phosphorous in formula I.

7. The composition according to claim 6 wherein the mixture comprises at least two phosphorous diastereomers in any proportion from 1:99 to 99:1.

* * * * *